US009850477B2

(12) United States Patent
Perret et al.

(10) Patent No.: US 9,850,477 B2
(45) Date of Patent: *Dec. 26, 2017

(54) METHOD FOR PURIFYING ACTIVE GLA-DOMAIN COAGULATION PROTEINS

(71) Applicant: LABORATOIRE FRANCAIS DU FRACTIONNEMENT ET DES BIOTECHNOLOGIES, Les Ulis (FR)

(72) Inventors: Gerard Perret, Choisy le Roi (FR); Nicolas Bihoreau, Orsay (FR); Laurent Siret, Villieres sur Orge (FR)

(73) Assignee: Laboratoire Francais du Fractionnement et des Biotechnologies, Les Ulis (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/936,896

(22) Filed: Nov. 10, 2015

(65) Prior Publication Data
US 2016/0138001 A1    May 19, 2016

Related U.S. Application Data

(63) Continuation of application No. 13/392,989, filed as application No. PCT/FR2010/051629 on Jul. 30, 2010, now Pat. No. 9,212,365.

(30) Foreign Application Priority Data

Jul. 31, 2009 (FR) ...................................... 09 55413

(51) Int. Cl.
 C12N 15/11 (2006.01)
 C12N 9/64 (2006.01)
 C07K 14/745 (2006.01)
 C12N 15/115 (2010.01)

(52) U.S. Cl.
 CPC .......... *C12N 9/6432* (2013.01); *C07K 14/745* (2013.01); *C12N 9/644* (2013.01); *C12N 9/6437* (2013.01); *C12N 15/115* (2013.01); C12N 2310/16 (2013.01); C12N 2310/351 (2013.01); C12N 2330/31 (2013.01); *C12Y 304/21006* (2013.01); *C12Y 304/21021* (2013.01); *C12Y 304/21022* (2013.01)

(58) Field of Classification Search
 CPC .. C12N 14/115; C12N 9/6437; C12N 9/6443; C12N 9/6464; C12N 9/647
 See application file for complete search history.

(56) References Cited

U.S. PATENT DOCUMENTS

| 5,071,961 A | 12/1991 | Kraus et al. | |
| 9,359,610 B2* | 6/2016 | Perret | C07K 14/745 |
| 2003/0175703 A1 | 9/2003 | Sullenger et al. | |
| 2012/0040905 A1 | 2/2012 | Perret et al. | |
| 2012/0041056 A1 | 2/2012 | Perret et al. | |

FOREIGN PATENT DOCUMENTS

| EP | 0354354 | 2/1992 |
| WO | WO 01/64748 | 9/2001 |
| WO | WO 2007/035532 | 3/2007 |
| WO | WO 2010/094899 | 8/2010 |
| WO | WO 2010/094900 | 8/2010 |
| WO | WO 2010/094901 | 8/2010 |

OTHER PUBLICATIONS

Layzer et al., "Simultaneous Generation of Aptamers to Multiple Gamma-Carboxygutamic Acid Proteins from a Focused aptamer Library Using DeSELEX and Convergent Selection," Oligonucleotides, vol. 17, pp. 1-11, 2007.
Li et al., "Fabrication and characterization of RNA aptamer microarrays for the study of protein-aptamer interactions with SPR imaging," Nucleic Acids Research, vol. 34, No. 22, pp. 6416-6424. 2006.
Noma et al., "Screening of DNA aptamers against multiple proteins in tissue." Nucleic Acids Symposium Series, No. 49, pp. 357-358, 2005.
International Search Report dated Dec. 23, 2010, issued in application number PCT/FR2010/051629.
Office Action issued in U.S. Appl. No. 13/392,989 dated Aug. 6, 2013.
Office Action issued in U.S. Appl. No. 13/392,989 dated Dec. 9, 2013.
Office Action issued in U.S. Appl. No. 13/392,989 dated Mar. 9, 2014.
Office Action issued in U.S. Appl. No. 13/392,989 dated Aug. 1, 2014.
Office Action issued in U.S. Appl. No. 13/392,989 dated Mar. 4, 2015.
Notice of Allowance issued in U.S. Appl. No. 13/392,989 dated Aug. 11, 2015.
Kulbachinskiy, "Methods for Selection of Aptamer to Protein Targets," Biochemistry, vol. 72, No. 13, 2007, pp. 1505-1518.
Van Cott et al., "Affinity Purification of Biologically Active and Inactive Forms of Recombinant Human Protein C Produced in Porcine Mammary Gland," Journal of Molecular Recognition, vol. 9, 1996, pp. 407-414.
Clarke et al.; "Incomplete gamma carboxylation of human coagulation factor VII: differential effects on tissue factor binding and enzymatic activity"; British Journal of Haematology, 93(2):445-450 (1996).
Presnell, et al.; "The Vitamin K-dependent Carboxylase"; Thrombosis and Haemostasis, 87(6):937-46 (2002).

* cited by examiner

*Primary Examiner* — Karen Cochrane Carlson
(74) *Attorney, Agent, or Firm* — Potomac Law Group, PLLC; Rouget F. Henschel

(57) ABSTRACT

The invention relates to a method for purifying biologically active GLA-domain coagulation proteins, comprising the following steps: a) bringing a sample that contains one or more GLA-domain coagulation proteins and may contain biologically inactive molecules of GLA-domain protein(s), into contact with an affinity support on which nucleic aptamers that bind specifically to at least one biologically active GLA-domain coagulation protein are immobilized, in order to form complexes between (i) said nucleic aptamers and (ii) said GLA-domain coagulation protein(s), b) releasing the GLA-domain coagulation protein(s) from the complexes formed in step a), and c) recovering said biologically active GLA-domain coagulation protein(s) in a purified form.

13 Claims, 26 Drawing Sheets

US 9,850,477 B2

METHOD FOR PURIFYING ACTIVE GLA-DOMAIN COAGULATION PROTEINS

FIELD OF THE INVENTION

The present invention relates to the field of protein purification, and in particular to the field of the purification of GLA-domain coagulation proteins, and even more specifically active GLA-domain coagulation proteins.

PRIOR ART

Generally, GLA domain proteins form a family of proteins having a common structure, the GLA domain which consists of a region located toward the N-terminal end of these proteins and which comprises a plurality of glutamate residues which are in particular carboxylated to give carboxyglutamic acid or "GLA" residues. GLA-domain proteins generally comprise an N-terminal portion called a propeptide which is recognized by a vitamin K-dependent carboxylase. After carboxylation of the glutamate residues of the GLA domain, the propeptide is cleaved by proteolysis and the mature and active GLA-domain protein is released. Depending on the proteins under consideration, the GLA domain consists of approximately 45 amino acids comprising from 9 to 12 glutamate residues which are normally carboxylated to give Gla.

GLA-domain proteins consist of "vitamin K-dependent" proteins. GLA-domain proteins encompass coagulation factors, bone tissue proteins and conopeptides. GLA-domain coagulation factors encompass prothrombin (Factor II), Factor VII, Factor IX, Factor X, protein C and protein S. GLA-domain bone tissue proteins encompass osteocalcin and matrix Gla protein. GLA-domain conopeptides encompass conantokin G and conantokin T. GLA-domain proteins also encompass other proteins, such as protein Z, Gas6, PRGP1 and PRGP2. GLA-domain proteins are presented in particular in the article by Furie et al. (1999, Blood, Vol. 93: 1798-1808).

Vitamin K-dependent GLA-domain coagulation proteins consist of proteins of therapeutic interest. Among said proteins, Factor II, Factor VII, Factor IX and Factor X represent proteins of very great therapeutic interest which are administered for the prevention and treatment of numerous homeostasis disorders. Human GLA-domain coagulation proteins can be purified from natural human fluids, generally from human blood plasma. Moreover, numerous studies have been undertaken in order to develop methods for producing and purifying recombinant human GLA-domain coagulation proteins. Mention may be made, for example, of recombinant human Factor VII, which is already sold as a medicament.

It is understood that obtaining purified preparations in which the coagulation factor(s) of interest is (are) in a biologically active form is of very great importance, since they are substances which are used as active ingredients of medicaments.

Mention may in particular be made of the obtaining of purified preparations of GLA-domain coagulation factors produced in the form of recombinant proteins, in vitro by means of genetically transformed cells or in vivo by means of transgenic animals, for which it is essential to select the biologically active forms of these recombinant factors which are produced in artificial systems or in systems that are heterologous to humans.

For obtaining GLA-domain proteins purified from biological fluids in which these proteins are produced naturally or else in the form of recombinant proteins, suitable purification methods are already known in the prior art. These methods generally comprise a succession of selective separation steps based on steps of protein precipitation and of passage over chromatography supports, followed by sequential-elution steps, deep-filtration steps, ultrafiltration, or else concentration steps. The methods for purifying GLA-domain coagulation proteins that are used today for producing medicaments do not comprise an affinity chromatography step. One reason for such a technical choice lies in the drawbacks created by the detachment of a part of the ligand molecules grafted onto the affinity support, which are found associated with the purified therapeutic protein in the volume of the chromatography eluate. By way of illustration, mention may be made of the product Mononine®, which is a pharmaceutical composition based on purified human Factor IX, which is obtained by means of a method using an immunoaffinity support on which mouse anti-FIX monoclonal antibodies are immobilized. However, the monograph of the Mononine® product specifies the presence of traces of murine anti-human FIX monoclonal antibodies in the final product, which is able to cause immunogenicity problems in treated patients since they become immunized against the "leachables" (murine antibodies and antibody fragments). The monograph of the Mononine® product specifies contraindications for patients allergic to murine proteins.

It is known in the prior art that partial or total integrity of the GLA domain of GLA-domain coagulation proteins, including prothrombin, Factor VII, Factor IX, Factor X, protein C and protein S, is important for maintaining their biological activity.

There therefore exists a need in the prior art for improved or alternative methods for purifying active GLA-domain coagulation proteins. This encompasses a need for alternative or improved methods for obtaining compositions comprising a single purified active protein, such as, for example, Factor VII or Factor IX, and also alternative or improved methods for obtaining compositions comprising a combination of active GLA-domain proteins, for example compositions comprising a combination of active Factor II, active Factor VII, active Factor IX and active Factor X. This encompasses a need for alternative or improved methods for purifying nonrecombinant active GLA-domain proteins or recombinant active GLA-domain proteins.

SUMMARY OF THE INVENTION

The present invention relates to a method for purifying biologically active GLA-domain coagulation proteins, comprising the following steps:
   a) bringing a sample which contains one or more GLA-domain coagulation proteins, and which may contain biologically inactive molecules of GLA-domain protein(s), into contact with an affinity support on which nucleic aptamers which bind specifically to at least one biologically active GLA-domain coagulation protein are immobilized, in order to form complexes between (i) said nucleic aptamers and (ii) said active GLA-domain coagulation protein(s),
   b) releasing the active GLA-domain coagulation protein(s) from the complexes formed in step a), and
   c) recovering said biologically active GLA-domain coagulation protein(s) in a purified form.

In the above methods, said aptamers are preferentially deoxyribonucleic aptamers.

In the above methods, said GLA-domain coagulation protein may be a vitamin K-dependent coagulation factor, for example chosen from Factor II, Factor VII, Factor IX, Factor X, protein C and protein S.

In certain embodiments of these methods, said nucleic aptamers consist of aptamers of sequence SEQ ID NO. 4.

DESCRIPTION OF THE FIGURES

FIG. 3A represents the entire SDS-PAGE gel after staining. FIG. 3B is a detailed portion of the gel of FIG. 3A. Lanes "St" and "S": reference proteins of known molecular weight; lanes 1, 2 and 4: proteins contained in the elution fraction after chromatography on an MEP HyperCel® support then purification on an affinity support on which nucleic aptamers specific for GLA-domain proteins are grafted, following distinct assays; lane 3: purified fraction of human plasma Factor IX (25 ng of Factor IX loaded on the SDS-PAGE gel); lane 3': purified fraction of human plasma Factor IX (550 ng of Factor IX loaded on the SDS-PAGE gel). The apparent molecular weights of certain protein bands are indicated in FIGS. 3A and 3B.

(5): 50 mM Tris buffer containing 10 mM CaCl$_2$, 4 mM MgCl$_2$, 3M NaCl, pH 7.5 and (6) 50 mM Tris buffer containing 10 mM EDTA. Along the x-axis: the time, expressed in seconds; along the y-axis, resonance signal, expressed in arbitrary resonance units.

Figure 24:
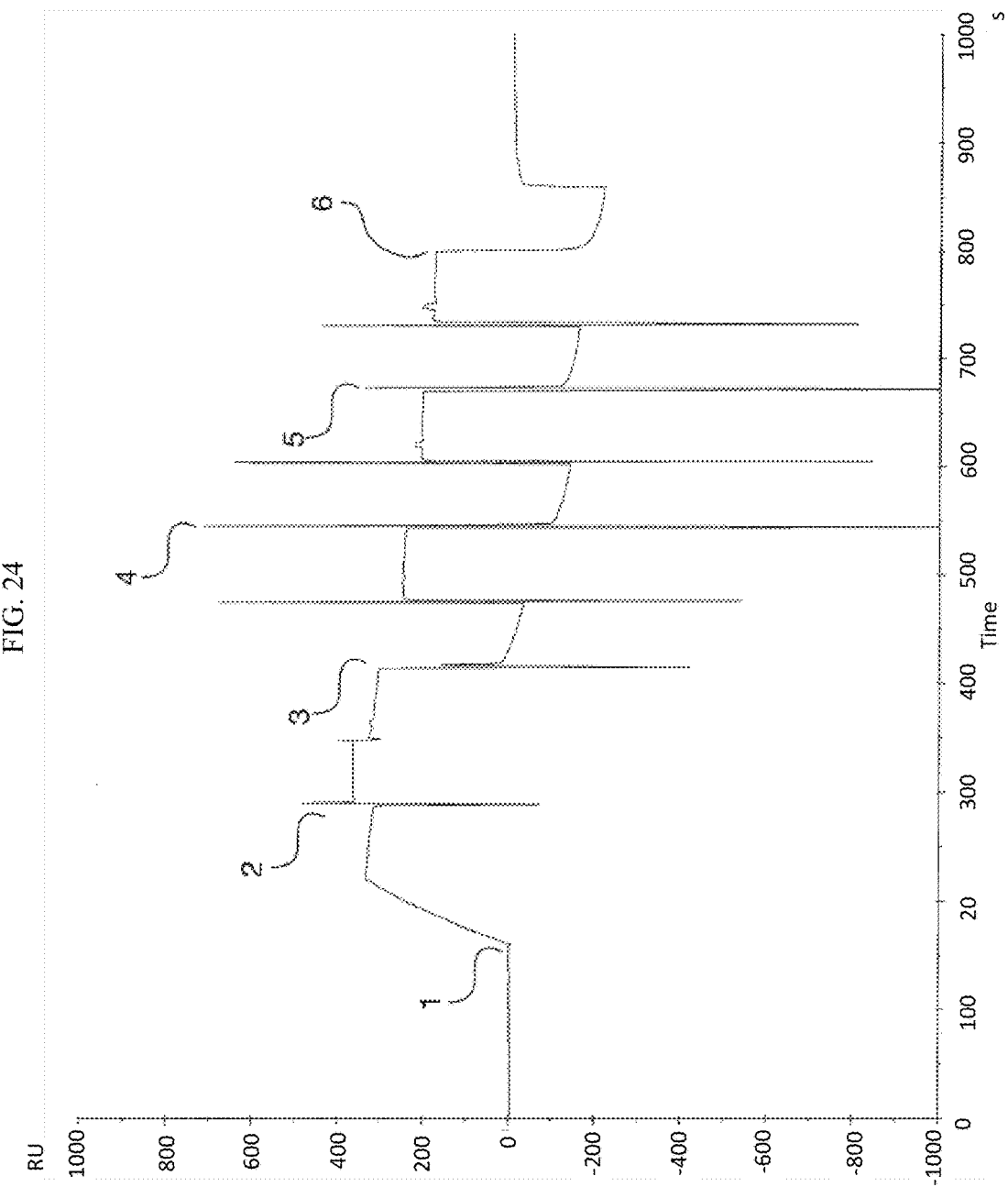

FIG. 24 shows the curves of binding of the Mapt-2 aptamer which is immobilized on a support, to human plasma Factor VII, in an assay according to the surface plasmon resonance technique. The curves correspond to the resistance of the binding of plasma FVII to Mapt-2 when various washing buffers are used: (1): injection of FVII; (2): 10% ethanol buffer, (3): 50 mM Tris buffer containing 10 mM CaCl$_2$, 4 mM MgCl$_2$, 1M NaCl, pH 7.5, (4): 50 mM Tris buffer containing 10 mM CaCl$_2$, 4 mM MgCl$_2$, 2M NaCl, pH 7.5; (5): 50 mM Tris buffer containing 10 mM CaCl$_2$, 4 mM MgCl$_2$, 3M NaCl, pH 7.5; and (6): 50 mM Tris buffer containing 10 mM EDTA. Along the x-axis: the time, expressed in seconds; along the y-axis, resonance signal, expressed in arbitrary resonance units.

Figure 25:
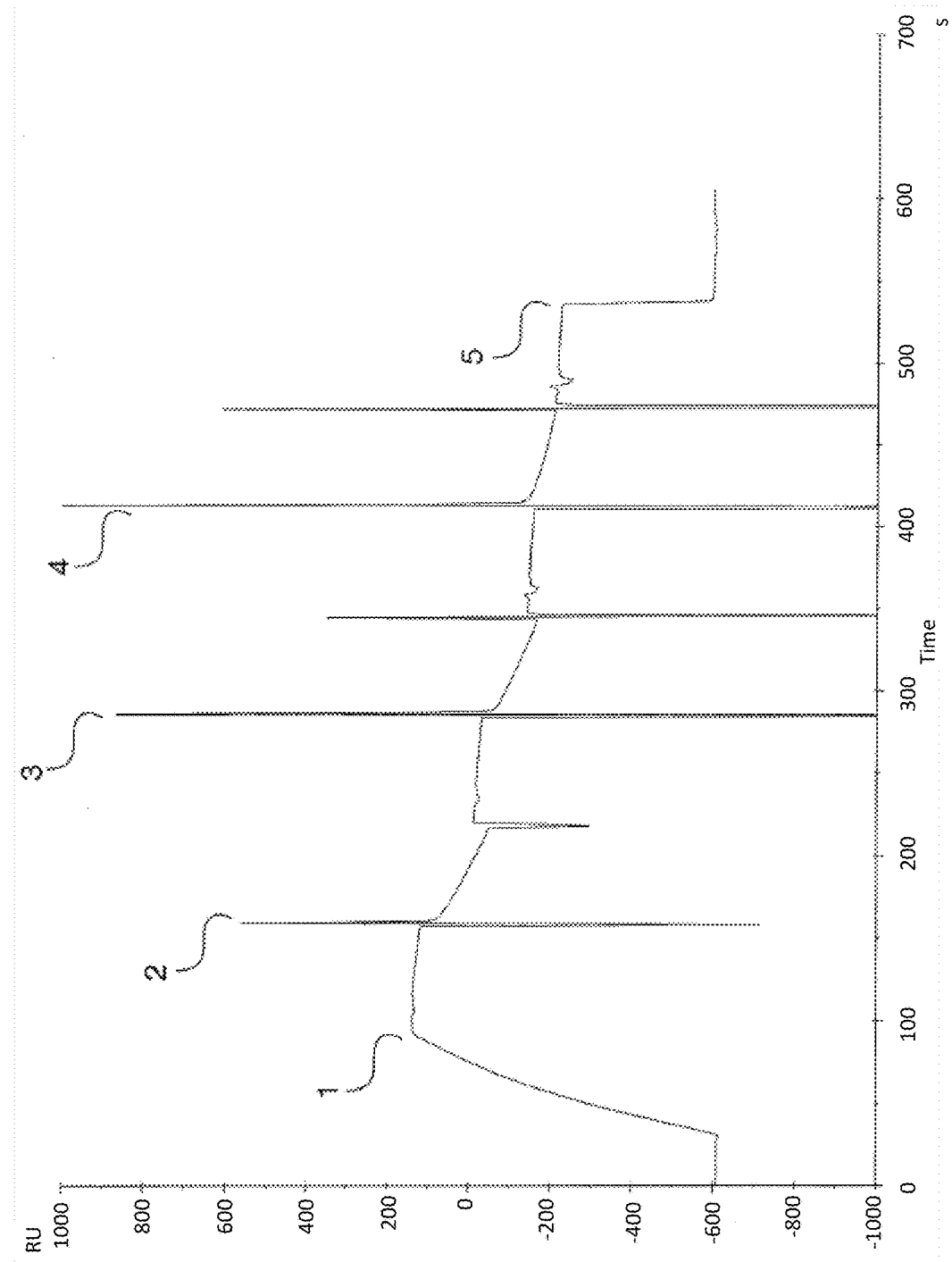

FIG. 25 shows the curves of binding of the Mapt-1 aptamer which is immobilized on a support, to recombinant human Factor VII, in an assay according to the surface plasmon resonance technique. The curves correspond to the resistance of the binding of recombinant FIX to Mapt-1 when various washing buffers are used: (1): injection of recombinant FVII; (2): 50 mM Tris buffer containing 10 mM CaCl$_2$, 4 mM MgCl$_2$, 1M NaCl, pH 7.5, (3): 50 mM Tris buffer containing 10 mM CaCl$_2$, 4 mM MgCl$_2$, 2M NaCl, pH 7.5; (4): 50 mM Tris buffer containing 10 mM CaCl$_2$, 4 mM MgCl$_2$, 3M NaCl, pH 7.5 and (5): 50 mM Tris buffer containing 10 mM EDTA. Along the x-axis: the time, expressed in seconds; along the y-axis, resonance signal, expressed in arbitrary resonance units.

Figure 26:
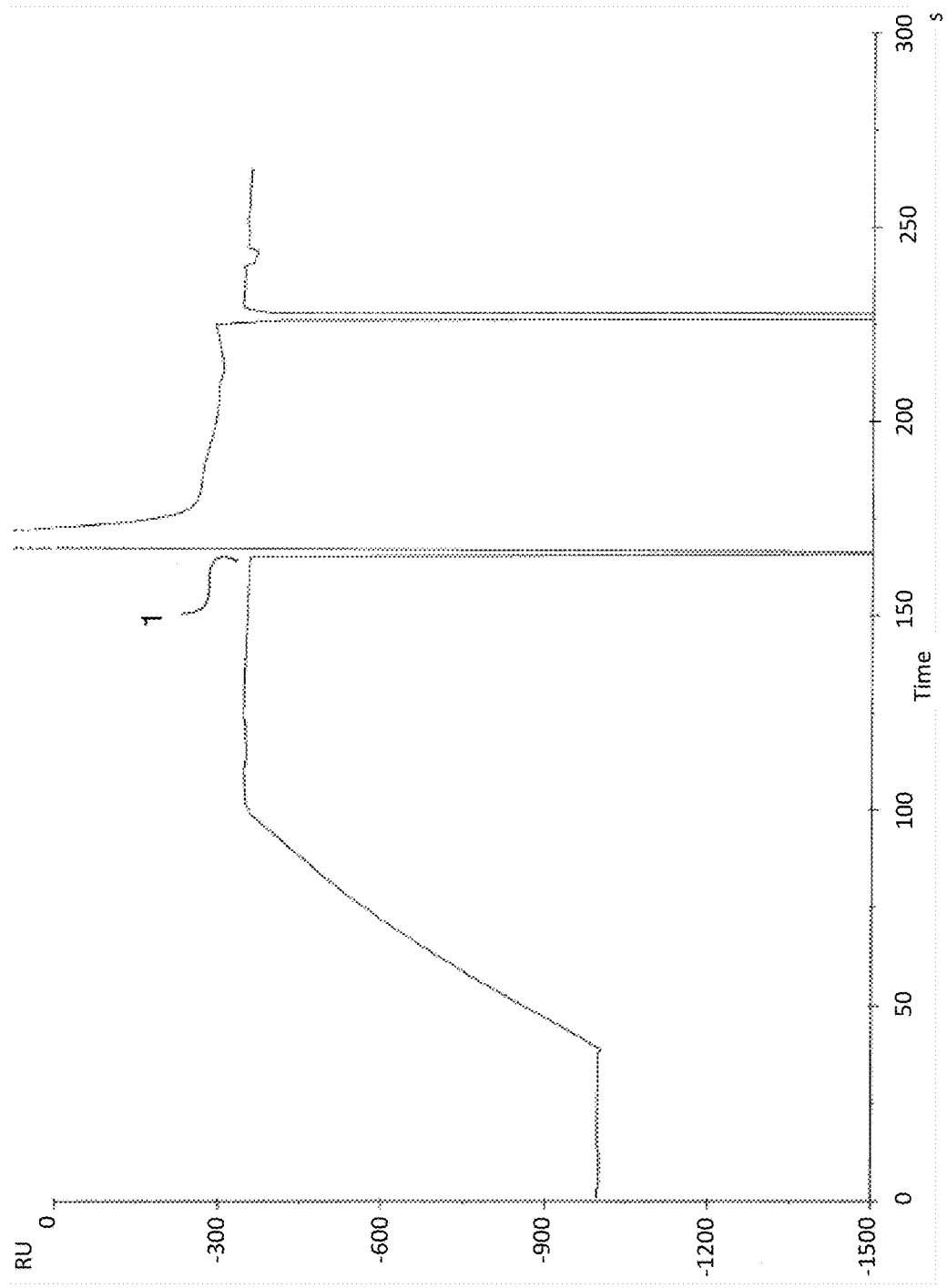

FIG. 26 shows the curves of binding of the Mapt-2 aptamer which is immobilized on a support, to recombinant human Factor IX, in an assay according to the surface plasmon resonance technique. The curves correspond to the resistance of the binding of recombinant FIX to Mapt-1 when the following washing buffer is used: 50 mM Tris, 10 mM CaCl$_2$, 50% propylene glycol, at pH 7.5. Along the x-axis: the time, expressed in seconds; along the y-axis, resonance signal, expressed in arbitrary resonance units. (1): injection of 50% propylene glycol in buffer 5.

DETAILED DESCRIPTION OF THE INVENTION

The applicant endeavors to design novel methods for purifying active GLA-domain coagulation proteins, i.e. novel methods suitable for obtaining purified and active GLA-domain coagulation protein(s) from a starting sample comprising a GLA-domain coagulation protein or a plurality of GLA-domain coagulation proteins. In other words, the applicant has sought to develop enrichment or purification methods which are selective (i) for a given active GLA-domain coagulation protein, or (ii) for a plurality of active GLA-domain coagulation proteins.

In order to develop these purification methods, the applicant has isolated and characterized novel ligands which have the ability to bind specifically to an active GLA-domain protein or to a plurality of active GLA-domain coagulation proteins.

These novel ligands do not detectably bind to a inactive GLA-domain coagulation protein.

Furthermore, these novel ligands can be immobilized on the surface of a solid support in order to prepare supports for affinity purification of GLA-domain coagulation proteins, said affinity purification supports having a reduced risk, or even a zero risk, of releasing the ligands and therefore of contaminating the purified final product with said ligands, or with fragments or products resulting from the degradation of said ligands.

These novel ligands, the characteristics of which are detailed later in the present description, consist of nucleic acids, also called "nucleic aptamers", which bind to active GLA-domain coagulation proteins. In certain embodiments, said aptamers are specific for a predetermined active GLA-domain coagulation protein. In other embodiments, said aptamers are not specific for a particular active GLA-domain coagulation protein and can bind to a plurality of active GLA-domain coagulation proteins.

The present invention provides methods for purifying active GLA-domain coagulation proteins, in which advantage is taken of the binding properties of these novel ligands of the nucleic acid type.

The applicant has also endeavored to develop methods for obtaining nucleic aptamers which bind specifically to active GLA-domain proteins, with the objective of using said nucleic aptamers in methods for purifying said active proteins.

According to the invention, nucleic aptamers which bind specifically to active GLA-domain coagulation proteins have been obtained. More specifically, the applicant has obtained and characterized nucleic aptamers which bind exclusively to just one or to a plurality of active GLA-domain coagulation protein (s), i.e. to proteins having a GLA domain of which the glutamate residues characteristic of the GLA domain have been at least partially gamma-carboxylated and of which the partial gamma-carboxylation of the GLA domain is sufficient for said GLA-domain coagulation proteins to be active.

In certain embodiments, a nucleic aptamer of the invention, which is specific for a predetermined GLA-domain coagulation protein, is capable of binding selectively to an active form of said GLA-domain coagulation protein, and does not bind to an inactive form of said GLA-domain protein.

In other embodiments, a nucleic aptamer of the invention, which is specific for active GLA-domain proteins, is capable of binding without distinction to a variety of proteins having a conserved common characteristic which is the GLA domain, the gamma-carboxylation level of which enables these proteins to be active, and does not bind to the inactive forms of said GLA-domain coagulation proteins.

It has in particular been shown in the examples that an aptamer specific for GLA-domain coagulation proteins is capable of binding to a plurality of active proteins, such as Factor IX, Factor VII and Factor X.

The results presented in the examples show that the anti-GLA aptamers of the invention, such as, for example, the Mapt-2-CS aptamer of sequence SEQ ID NO. 37 or the Mapt-2.2.-CS aptamer of sequence SEQ ID NO. 38, bind exclusively to the active forms of GLA-domain coagulation proteins, in particular bind exclusively to the active forms of human Factor VII. For example, these anti-GLA aptamers do not bind to the Des-Gla forms of human Factor VII, which consist of nonfunctional forms comprising modifications or an absence of the GLA domain.

Nucleic aptamers which specifically and individually recognize GLA-domain proteins such as Factor II, Factor VII, Factor IX or Factor X are already known in the prior art, including aptamers which bind thrombin (Zhao et al. 2008, Anal Chem, Vol 80(19): 7586-7593), aptamers which bind Factor IX/IXa (Subash et al., 2006, Thromb Haemost, Vol.

95: 767-771; Howard et al., 2007, Atherioscl Thromb Vasc Biol, Vol. 27: 722-727; PCT application No. WO 2002/096926; U.S. Pat. No. 7,312,325), aptamers which bind Factor X/Xa (PCT application No. WO 2002/096926; U.S. Pat. No. 7,312,325) or else aptamers which bind to human Factor VII/VIIa (Rusconi et al., 2000, Thromb Haemost, Vol. 84(5): 841-848; Layzer et al., 2007, Spring, Vol. 17: 1-11).

It is specified that none of the aptamers above is described for its use for purifying the target protein to which it binds. Furthermore, the aptamers above bind exclusively to a single GLA-domain protein, without crossing with another GLA-domain protein, thereby making it possible to imagine that the known aptamers do not bind to the GLA domain of GLA-domain coagulation proteins, and are consequently not capable of binding selectively to the GLA domain of an active GLA-domain protein.

Such a type of aptamer, specific for a given GLA-domain protein, and which does not have the ability to bind to another protein, including to another GLA-domain protein, is, for example, described by Layzer et al. (2007, Oligonucleotides, Vol. 17: 1-11).

However, to the applicant's knowledge, a nucleic aptamer, the binding specificity of which is the GLA domain of proteins, and which has the ability to bind selectively to one or more active GLA-domain coagulation proteins, has never been described in the prior art.

Furthermore, to the applicant's knowledge, a nucleic aptamer, the binding specificity of which is the GLA domain of proteins, and which has the ability to bind to a plurality of distinct active GLA-domain coagulation proteins, has also not been described in the prior art.

The availability of nucleic aptamers which bind specifically to active GLA-domain coagulation proteins has made it possible to develop methods for purifying these proteins, in particular with the objective of obtaining a purified final product that can be used as an active ingredient of a medicament. Depending on the type of specificity of the nucleic aptamer which is used, said purification methods allow (i) either the selective purification of a predetermined active GLA-domain coagulation protein, (ii) or the selective purification of the active forms of a plurality of GLA-domain coagulation proteins.

The present invention relates to a method for purifying at least one biologically active GLA-domain coagulation protein, comprising the following steps:
 a) bringing a sample which contains one or more GLA-domain coagulation proteins into contact with an affinity support on which nucleic aptamers which bind specifically to biologically active GLA-domain coagulation proteins are immobilized, in order to form complexes between (i) said nucleic aptamers and (ii) said active GLA-domain coagulation protein(s),
 b) releasing the biologically active GLA-domain coagulation protein(s) from the complexes formed in step a), and
 c) recovering said biologically active GLA-domain coagulation protein(s) in a purified form.

The present invention also relates to a method for purifying biologically active GLA-domain coagulation proteins, comprising the following steps:
 a) bringing a sample which contains one or more GLA-domain coagulation proteins into contact with an affinity support on which nucleic aptamers which bind specifically to a plurality of biologically active GLA-domain coagulation proteins are immobilized, in order to form complexes between (i) said nucleic aptamers and (ii) said GLA-domain coagulation protein(s),
 b) releasing the biologically active GLA-domain coagulation protein(s) from the complexes formed in step a), and
 c) recovering said biologically active GLA-domain coagulation protein(s) in a purified form.

The term "GLA-domain coagulation protein" encompasses any coagulation protein comprising a region, denoted GLA domain, comprising a plurality of glutamate residues which are gamma-carboxylated during protein synthesis. The GLA-domain coagulation proteins encompass coagulation proteins which have a GLA domain toward the N-terminal end, said GLA domain generally being located downstream, i.e. on the C-terminal side, of a propeptide which is naturally hydrolyzed during synthesis. The GLA-domain coagulation proteins encompass coagulation proteins in which the GLA domain consists of a region of approximately 45 amino acids comprising from 9 to 12 glutamate residues, at least a part of which are normally carboxylated to give GLA residues during the protein synthesis process in cells. The GLA-domain coagulation factors, which consist of vitamin K-dependent proteins, encompass prothrombin (Factor II), Factor VII, Factor IX, Factor X, protein C and protein S. The GLA-domain coagulation proteins encompass nonrecombinant proteins originating from natural sources, such as blood plasma, and also recombinant proteins which can be produced in vitro by cells transfected or transformed with a DNA encoding said coagulation protein or which can be produced in vivo by animals into which a trans gene encoding said coagulation protein has been introduced. The GLA-domain coagulation proteins produced by transgenic animals may also be called "utransgenic proteins" in the present description.

Methods for determining the activity of GLA-domain coagulation proteins are described in detail later in the present description.

An "active" or "biologically active" GLA-domain coagulant protein encompasses GLA-domain coagulation proteins which have at least half the level of anticoagulant or amidolytic activity that is determined for a corresponding reference protein of which respectively the anticoagulant activity or the amidolytic activity is judged to be optimum. An active GLA-domain coagulation protein encompasses GLA-domain coagulation proteins which have at least 0.5, 0.55, 0.6, 0.65, 0.7, 0.75, 0.8, 0.85, 0.9, 0.95, 0.96, 0.97, 0.98, 0.99 or 1 times the level of anticoagulant or amidolytic activity that is determined for a corresponding reference protein of which respectively the anticoagulant activity or the amidolytic activity is judged to be optimum. An active GLA-domain protein also encompasses GLA-domain proteins, which can also be denoted "superactive" GLA proteins, which have a level of anticoagulant or amidolytic activity greater than the reference protein or composition, i.e. which have a level of anticoagulant or amidolytic activity greater than 1.

Active Factor II (prothrombin) encompasses Factors II which have at least half the level of anticoagulant or amidolytic activity that is determined for the corresponding reference Factor II of which respectively the anticoagulant activity or the amidolytic activity is judged to be optimum.

Active Factor VII encompasses Factors VII which have at least half the level of anticoagulant or amidolytic activity that is determined for the corresponding reference Factor VII of which respectively the anticoagulant activity or the amidolytic activity is judged to be optimum.

Active Factor IX encompasses Factors IX which have at least half the level of anticoagulant or amidolytic activity that is determined for the corresponding reference Factor IX of which respectively the anticoagulant activity or the amidolytic activity is judged to be optimum.

Active Factor X encompasses Factors X which have at least half the level of anticoagulant or amidolytic activity that is determined for the corresponding reference Factor X of which respectively the anticoagulant activity or the amidolytic activity is judged to be optimum.

Active protein C encompasses proteins C which have at least half the level of anticoagulant or amidolytic activity that is determined for the corresponding reference protein C of which respectively the anticoagulant activity or the amidolytic activity is judged to be optimum.

Active protein S encompasses proteins S which have at least half the level of anticoagulant or amidolytic activity that is determined for the corresponding reference protein S of which respectively the anticoagulant activity or the amidolytic activity is judged to be optimum.

In the light of the aforementioned, those skilled in the art understand that an "active" or "biologically active" GLA-domain coagulation protein should not be confused with GLA-domain coagulation proteins which are "activated". GLA-domain coagulation proteins are "activated" as a result of a proteolysis reaction which cleaves a peptide, the resulting protein then exerting its own biological activity. The "activated" coagulation factors are generally denoted with an additional "a". By way of illustration, the Factor VII/"activated" Factor VII pair can be denoted as the FVII/FVIIa pair. However, for the purpose of the invention, there are both "biologically active" forms and "biologically inactive" forms of an "activated" coagulation factor, owing to the fact that there are forms of an "activated" GLA-domain coagulation factor which are "biologically inactive", for example owing to an incorrect gamma-carboxylation of their GLA domain.

Thus, for the purpose of the invention, a "biologically active" GLA-domain coagulation protein encompasses both (i) the "activated" form of said GLA-domain coagulation protein, which directly exerts its own biological activity, and (ii) the nonactivated form of said protein, which nonactivated form of said protein results, after activation, in a form of said protein which exerts its own biological activity.

The term "corresponding protein" or "corresponding factor" is intended to mean preferentially the protein or the factor of the same mammal, for example human being.

The active GLA-domain coagulation proteins, also called biologically active GLA-domain coagulation proteins, encompass the proteins of this type in which all of the glutamate residues of the GLA domain are gamma-carboxylated.

In certain cases, the active GLA-domain coagulation proteins encompass the proteins of this type in which at least one glutamate residue of the GLA domain is not gamma-carboxylated, but which is nevertheless biologically active for the purpose of the invention.

According to the invention, the term "nucleic aptamer" is intended to mean a single-stranded nucleic acid which binds specifically to one or more active GLA-domain coagulation proteins, which may also be denoted in the present description as "anti-GLA aptamer". The aptamers of the invention therefore encompass those for which it is possible to detect complexes with a single active GLA-domain coagulation protein or with a variety of given active GLA-domain coagulation proteins, after a prior step of bringing the respectively nucleic and protein partners into contact. Preferentially, a "nucleic aptamer" according to the invention has the ability to bind to a plurality of active GLA-domain proteins.

The detection of complexes formed between an anti-GLA aptamer according to the invention and an active GLA-domain coagulation protein can be easily carried out by those skilled in the art, for example by implementing a surface plasmon resonance detection technique, including the Biacore® technique, as is illustrated in the examples. Those skilled in the art can also easily detect the formation of complexes between an anti-GLA aptamer according to the invention and an active GLA-domain coagulation protein by conventional techniques of the ELISA type, as is known by those skilled in the art.

It has been shown in the examples that an anti-GLA aptamer according to the invention is capable of binding selectively to the active forms of GLA-domain coagulation proteins, such as Factor IX. It has also been shown according to the invention that an anti-GLA aptamer is capable of binding respectively to a plurality of distinct active GLA-domain coagulation proteins, and in particular to a plurality of active human GLA-domain coagulation proteins. It has in particular been shown that a given anti-GLA aptamer according to the invention is capable of binding respectively to active Factor VII, to active Factor IX and to active Factor X.

In certain embodiments, the purification method above is characterized in that said GLA-domain coagulation protein is a vitamin K-dependent coagulation factor.

In certain embodiments, the purification method above is characterized in that said GLA-domain coagulation protein is chosen from Factor II, Factor VII, Factor IX, Factor X, protein C and protein S.

In certain embodiments, the purification method above is suitable for selectively purifying a single active GLA-domain coagulation protein chosen from Factor II, Factor VII, Factor IX, Factor X, protein C and protein S.

In certain embodiments, the purification method above is suitable for simultaneously purifying at least two active GLA-domain coagulation proteins chosen from Factor II, Factor VII, Factor IX, Factor X, protein C and protein S.

In certain embodiments, the purification method above is suitable for simultaneously purifying at least three active GLA-domain coagulation proteins chosen from Factor II, Factor VII, Factor IX, Factor X, protein C and protein S.

In certain embodiments, the purification method above is suitable for simultaneously purifying active Factor II, active Factor VII, active Factor IX and active Factor X.

In certain embodiments, the purification method above is suitable for purifying active Factor IX.

It has thus been shown in the examples that an anti-GLA aptamer according to the invention is capable of distinguishing active GLA-domain coagulation proteins from inactive GLA-domain coagulation proteins. In particular, it has been shown in the examples that an anti-GLA aptamer according to the invention is capable of distinguishing GLA-domain coagulation proteins of which the GLA domain is correctly gamma-carboxylated from GLA-domain coagulation proteins of which the GLA domain is incorrectly gamma-carboxylated.

According to the invention, a correctly gamma-carboxylated GLA domain encompasses a GLA domain of which all the characteristic glutamate residues are gamma-carboxylated and also a GLA domain of which only a part of the characteristic glutamate residues are gamma-carboxylated, but of which the partial gamma-carboxylation does not lead to the GLA-domain coagulation protein under consideration not being biologically active, for the purpose of the invention.

By way of illustration, for a GLA-domain coagulation protein such as Factor IX, the protein is biologically active when all of the characteristic glutamate residues of its GLA domain are gamma-carboxylated, and also when at least 7 glutamate residues of the GLA domain are gamma-carboxylated, among the 12 characteristic glutamate residues contained in its GLA domain. Thus, for Factor IX, the active proteins encompass the Factors IX in which 7, 8, 9, 10, 11 and 12 glutamate residues of the GLA domain have been gamma-carboxylated.

With regard to Factor IX, an anti-GLA nucleic aptamer according to the invention encompasses the aptamers which bind to Factors IX in which 7, 8, 9, 10, 11 and 12 glutamate residues of the GLA domain have been gamma-carboxylated and which do not bind to Factors IX in which less than 7 glutamate residues of the GLA domain have been gamma-carboxylated. As an example of such an aptamer, mention may be made of the aptamer of sequence SEQ ID NO. 4.

These properties of an anti-GLA aptamer of the invention, of distinguishing between active GLA-domain coagulation proteins and inactive GLA-domain coagulation proteins, can be used in methods for purifying active GLA-domain coagulation proteins, in order to obtain a final product which is greatly enriched in active form(s) of the GLA-domain coagulation protein(s) of interest. Examples of implementation of methods for purifying active forms of active GLA-domain coagulation proteins, in particular active forms of Factor IX, are illustrated in the examples. These advantageous distinction properties of the anti-GLA aptamers of the invention make it possible, for example, to obtain purified preparations of active recombinant human Factor IX from the milk of a mammal transgenic for human Factor IX, when said milk comprises both active forms and inactive forms of recombinant human Factor IX, in particular forms of recombinant human Factor IX of which the GLA domain is correctly gamma-carboxylated and forms of recombinant human Factor IX of which the GLA domain is incorrectly gamma-carboxylated.

The present invention also relates to a method for purifying biologically active GLA-domain coagulation proteins, comprising the following steps:
a) bringing a sample which contains one or more GLA-domain coagulation proteins, and which may contain biologically inactive molecules of GLA-domain coagulation protein(s), into contact with an affinity support on which nucleic aptamers which bind specifically to a biologically active GLA-domain coagulation protein or to a plurality of biologically active GLA-domain coagulation proteins are immobilized, in order to form complexes between (i) said nucleic aptamers and (ii) said active GLA-domain coagulation protein(s),
b) releasing the active GLA-domain coagulation protein(s) from the complexes formed in step a), and
c) recovering said biologically active GLA-domain coagulation protein(s) in a purified form.

In certain embodiments of the method above, said nucleic aptamers consist of deoxyribonucleic aptamers.

In certain embodiments, the purification method above is characterized in that said GLA-domain coagulation protein is a vitamin K-dependent coagulation factor.

In certain embodiments, the purification method above is characterized in that said GLA-domain coagulation protein is chosen from Factor II, Factor VII, Factor IX, Factor X, protein C and protein S.

In certain embodiments, the purification method above is suitable for selectively purifying a single active GLA-domain coagulation protein chosen from Factor II, Factor VII, Factor IX, Factor X, protein C and protein S.

In certain embodiments, the purification method above is suitable for simultaneously purifying at least two active GLA-domain coagulation proteins chosen from Factor II, Factor VII, Factor IX, Factor X, protein C and protein S.

In certain embodiments, the purification method above is suitable for simultaneously purifying at least three active GLA-domain coagulation proteins chosen from Factor II, Factor VII, Factor IX, Factor X, protein C and protein S.

In certain embodiments, the purification method above is suitable for simultaneously purifying active Factor II, active Factor VII, active Factor IX and active Factor X.

In certain embodiments, the purification method above is suitable for purifying active Factor IX.

As has already been mentioned previously, an "active" form of a GLA-domain coagulation protein consists of a form for which the GLA domain is correctly gamma-carboxylated, i.e. a form of the GLA-domain coagulation protein which is recognized by an anti-GLA aptamer according to the invention.

An anti-GLA aptamer can be obtained by means of methods which have been specially developed for the needs of the invention, and which are detailed later in the present description.

The simultaneous purification of more than one GLA-domain coagulation protein depends in particular on the type of starting sample that is used to carry out the purification method. In particular, the number and the identity of the GLA-domain coagulation proteins which are obtained in purified form at the end of the method are logically limited by the number and the identity of the GLA-domain coagulation proteins which are initially present in the starting sample.

For the purpose of the invention, the "purification" of an active GLA-domain coagulation protein means an enrichment in the active form(s) of said GLA-domain coagulation protein, i.e. the obtaining of a "purified" composition having a concentration of the active GLA-domain protein that is detectably greater than the initial concentration of said active GLA-domain coagulation protein in the starting sample which is subjected to the purification step. An active GLA-domain coagulation protein "in purified form" encompasses compositions comprising an active GLA-domain coagulation protein of which the concentration is detectably greater than its concentration in the starting composition before carrying out the purification step. Thus, an active GLA-domain coagulation protein of the invention encompasses a composition in which said active GLA-domain coagulation protein is purified to homogeneity, but is in no way restricted to this particular purified form. In particular, when the sample before purification comprises more than one GLA-domain coagulation protein, the purified active proteins cannot by definition be purified to homogeneity, simply because at least two active GLA-domain coagulation proteins coexist in the composition after purification.

Generally, the anti-GLA aptamers can consist of DNA (deoxyribonucleic acid) or RNA (ribonucleic acid) molecules and have an ability to bind to an active GLA-domain protein, which is greater than the ability to bind to an inactive GLA-domain coagulation protein.

An anti-GLA aptamer can be obtained by means of methods which have been specially developed for the needs of the invention, and which are detailed later in the present description.

In certain embodiments, the anti-GLA aptamers according to the invention have various common structural characteristics, including a sequence comprising, from the 5' end to the 3' end, successively (i) an invariable specific nucleotide sequence of approximately 20 nucleotides in length (for example 18 nucleotides in length), followed by (ii) a variable nucleotide sequence of approximately 40 to 50 nucleotides in length (for example 44 nucleotides in length), followed by (iii) an invariable specific nucleotide sequence of approximately 20 nucleotides in length (for example 18 nucleotides in length). It is specified that the variable nucleotide sequences (ii) can have a very strong nucleotide sequence identity with respect to one another.

Some of the methods for selecting anti-GLA aptamers which are specified in the present description are of the type which makes it possible to obtain a family of anti-GLA aptamers, capable of selectively recognizing a predetermined active GLA-domain coagulation protein, in particular a predetermined human active GLA-domain coagulation protein.

Some of the other methods for selecting anti-GLA aptamers which are specified in the present description are of the type which makes it possible to obtain a family of anti-GLA aptamers, capable of selectively recognizing a plurality of active GLA-domain coagulation proteins, in particular a plurality of human active GLA-domain coagulation proteins.

From a structural point of view, the family of nucleic acids, or nucleic aptamers, which bind specifically to the active GLA-domain coagulation proteins of the invention comprises at least 15 consecutive nucleotides of a polynucleotide having at least 40% nucleotide identity with the nucleic acid of formula (I) below:

5'-[SEQ ID NO.1]x-[SEQ ID NO.X]-[SEQ ID NO.2]y-3'     (I), in which:
"SEQ ID NO. X" consists of a nucleic acid of sequence SEQ ID NO. 3,
"X" is an integer equal to 0 or 1, and
"Y" is an integer equal to 0 or 1.

In certain embodiments, the acid of sequence SEQ ID NO. X has a length of 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nucleotides.

In other embodiments, the nucleic acid of sequence SEQ ID NO. X has a length of 43, 44, 45, 46, 47, 48 or 49 nucleotides.

In certain other preferred embodiments, the nucleic acid of sequence SEQ ID NO. X has a length of 43, 44 or 45 nucleotides.

As already mentioned previously, the nucleic acid of formula (I) is at least 15 nucleotides in length.

In certain embodiments, the nucleic acid of formula (I) is at least 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80 or 81 nucleotides in length, thereby encompassing nucleic acids having exactly each of the lengths specified.

When the integer "x" is equal to 0 and the integer "y" is equal to 1, the nucleic aptamers of the invention encompass nucleic acids comprising at least 15 consecutive nucleotides of a polynucleotide having at least 40% nucleotide identity with the nucleic acid of formula (I-1) below:

5'-[SEQ ID NO.X]-[SEQ ID NO.2]-3'     (I-1)

When the integer "x" is equal to 1 and the integer "y" is equal to 0, the nucleic aptamers of the invention encompass nucleic acids comprising at least 15 consecutive nucleotides of a polynucleotide having at least 40% nucleotide identity with the nucleic acid of formula (I-2) below:

5'-[SEQ ID NO.1]-[SEQ ID NO.X]-3'     (I-2)

When the integer "x" is equal to 0 and the integer "y" is equal to 0, the nucleic aptamers of the invention encompass nucleic acids comprising at least 15 consecutive nucleotides of a polynucleotide having at least 40% nucleotide identity with the nucleic acid of formula (I-3) below:

5'-[SEQ ID NO.X]-3'     (I-3)

The nucleic aptamers above therefore encompass nucleic acids comprising at least 15 consecutive nucleotides of a polynucleotide having at least 40% nucleotide identity with a nucleic acid of sequence SEQ ID NO. 3.

Generally, a first polynucleotide having at least 40% nucleotide identity with a second polynucleotide or nucleic acid has at least 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 100% nucleotide identity with said second polynucleotide or nucleic acid.

In certain embodiments of a nucleic acid of the invention comprising the sequence SEQ ID NO. X, said sequence SEQ ID NO. X is chosen from the group consisting of nucleic acids having at least 15 consecutive nucleotides of a sequence having at least 40% nucleotide identity with a sequence chosen from the sequences SEQ ID NOS. 3, 6 to 35, 37 and 38.

In certain embodiments of a nucleic acid of the invention comprising the sequence SEQ ID NO. X, said sequence SEQ ID NO. X is chosen from the group consisting of nucleic acids having at least 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 100% nucleotide identity with a sequence chosen from the sequences SEQ ID NOS. 3, 6 to 35, 37 and 38.

In certain embodiments of a nucleic aptamer of the invention, said aptamer is chosen from nucleic acids comprising a sequence of at least 15 consecutive nucleotides of a sequence having at least 40% nucleotide identity with a sequence chosen from the sequences SEQ ID NOS. 3, 4 and 6 to 39.

In certain embodiments of a nucleic aptamer of the invention, said aptamer is chosen from nucleic acids comprising a sequence of at least 15 consecutive nucleotides of a sequence chosen from the sequences SEQ ID NOS. 3, 4 and 6 to 39.

In certain embodiments of a nucleic aptamer of the invention, said aptamer is chosen from nucleic acids comprising a sequence having at least 40% nucleotide identity with a sequence chosen from the sequences SEQ ID NOS. 3, 4 and 6 to 39.

In certain embodiments of a nucleic aptamer of the invention, said aptamer is chosen from nucleic acids comprising a sequence chosen from the sequences SEQ ID NOS. 3, 4 and 6 to 39.

In certain embodiments of a nucleic aptamer of the invention, said aptamer is chosen from nucleic acids consisting of a sequence chosen from the sequences SEQ ID NOS. 3, 4 and 6 to 39.

It results from the aforementioned that the present invention encompasses a family of single-stranded nucleic acids having at least 15 consecutive nucleotides of the series of formula (I) defined above.

For the purpose of the present invention, the "percentage identity" between two nucleic acid sequences is determined by comparing the two optimally aligned sequences, through a comparison window.

The part of the nucleotide sequence in the comparison window can thus comprise additions or deletions (for example gaps) compared with the reference sequence (which does not comprise these additions or these deletions) so as to obtain an optimum alignment between the two sequences.

The percentage identity is calculated by determining the number of positions at which an identical nucleic base is observed for the two sequences compared, then by dividing the number of positions at which there is identity between the two nucleic bases by the total number of positions in the comparison window, and then by multiplying the result by one hundred in order to obtain the percentage nucleotide identity of the two sequences with respect to one another.

The optimum alignment of the sequences for the comparison can be carried out by computer using known algorithms.

Entirely preferably, the percentage sequence identity is determined using the CLUSTAL W software (version 1.82), the parameters being fixed as follows: (1) CPU MODE=ClustalW mp; (2) ALIGNMENT="full"; (3) OUTPUT FORMAT="aln w/numbers"; (4) OUTPUT ORDER="aligned"; (5) COLOR ALIGNMENT="no"; (6) KTUP (word size)="default"; (7) WINDOW LENGTH="default"; (8) SCORE TYPE="percent"; (9) TOPDIAG="default"; (10) PAIRGAP="default"; (11) PHYLOGENETIC TREE/TREE TYPE="none"; (12) MATRIX="default"; (13) GAP OPEN="default"; (14) END GAPS="default"; (15) GAP EXTENSION="default"; (16) GAP DISTANCES="default"; (17) TREE TYPE="cladogram" and (18) TREE GRAPH DISTANCES="hide".

In certain preferred embodiments of an anti-GLA nucleic aptamer of the invention, said nucleic aptamer comprises at least 15 consecutive nucleotides of a polynucleotide having at least 80% nucleotide identity with the nucleic acid of formula (I), thereby encompassing the aptamers comprising 15 consecutive nucleotides of a polynucleotide having at least 81%, 82%, 83%, 84%, 85%, 86%, 87%, 88%, 89%, 90%, 91%, 92%, 93%, 94%, 95%, 96%, 97%, 98% or 100% nucleotide identity with said nucleic acid of formula (I).

The nucleic aptamers according to the invention encompass the nucleic aptamer of sequence SEQ ID NO. 4. It is recalled that the aptamer of sequence SEQ ID NO. 4 consists of an aptamer of formula (I) in which the sequence SEQ ID NO. X consists of the sequence SEQ ID NO. 3. It is also recalled that an aptamer of sequence SEQ ID NO. 3 consists of an aptamer of formula (I-3) in which the sequences SEQ ID NO. 1 and SEQ ID NO. 2 are absent.

The applicant has shown that the aptamer of sequence SEQ ID NO. 3 has an ability to selectively bind to active GLA-domain coagulation proteins that is substantially identical to that of the aptamer of sequence SEQ ID NO. 4. These results show the essential nature of the presence of the nucleic acid of sequence SEQ ID NO. 3 in the specific binding properties of the aptamer of sequence SEQ ID NO. 4. Generally, these results show the essential nature of the nucleic acid of sequence SEQ ID NO. X in an aptamer of formula (I), the nucleic acid of sequence SEQ ID NO. X conferring on the aptamer of formula (I) the ability to bind selectively to the active GLA-domain coagulation proteins.

The nucleic aptamers of the invention therefore also encompass the aptamer of sequence SEQ ID NO. 3.

It has also been shown in the examples that a great variety of aptamers, including the aptamers of sequences SEQ ID NOS. 6 to 35, have an ability to bind selectively to active GLA-domain coagulation proteins, where appropriate with distinct affinity levels. By way of illustration, among the aptamers of sequences SEQ ID NOS. 6 to 35, the aptamer which has the greatest ability to bind to human Factor IX is the aptamer of sequence SEQ ID NO. 35, which can also be denoted "Mapt-1.2.-CS".

Aptamers having an ability to bind to active GLA-domain coagulation proteins that is even greater than the Mapt-1.2.-CS aptamer above have also been identified in the examples. An example of such an aptamer is the aptamer of sequence SEQ ID NO. 36, which can also be denoted "Mapt-1.2.-CSO".

The Mapt-1.2.-CSO aptamer of sequence SEQ ID NO. 36 is an aptamer comprising at least 15 consecutive nucleotides of a polynucleotide having at least 40% nucleotide identity with the nucleic acid of 62 nucleotides in length, of formula (I) below:

5'-[SEQ ID NO.1]-[SEQ ID NO.35]-3', and consisting of the nucleic acid which goes from the nucleotide in position 10 to the nucleotide in position 49 of said nucleic acid of formula (I).

It has also been shown in the examples that each of the nucleic acids of sequences SEQ ID NOS. 37 to 39 has the ability to bind to active GLA-domain coagulation proteins. The aptamer of sequence SEQ ID NO. 39 can also be denoted "Mapt-2". The aptamer of sequence SEQ ID NO. 37 can also be denoted "Mapt-2-CS". The aptamer of sequence SEQ ID NO. 38 can also be denoted "Mapt-2.2.-CS". It is specified that the sequence of the Mapt-2-CS aptamer is included in the sequence of the Mapt-2 aptamer: it is the "core sequence" SEQ ID NO. X of the Mapt-2 aptamer.

It has been shown in the examples that the anti-GLA aptamers of the invention can be successfully used for producing affinity chromatography supports, that are of use for separating active GLA-domain coagulation proteins from inactive GLA-domain coagulation proteins.

To prepare affinity chromatography supports in particular, the anti-GLA nucleic aptamers of the invention are preferentially included in a chemical structure, also called "compound" in the present description, which comprises in particular a spacer means and, where appropriate, a means for immobilization on a solid support.

In certain embodiments, the nucleic aptamer is included in the structure of a compound of formula (II) below:

[IMM]$_x$-[SPAC]$_y$-[APT]   (II), in which:

[IMM] signifies a compound for immobilization on a support,
[SPAC] signifies a spacer chain,
[APT] signifies an anti-GLA aptamer as defined in the present description,
x is an integer equal to 0 or 1, and
y is an integer equal to 0 or 1.

In certain embodiments of the compound of formula (II), [APT] consists of a deoxyribonucleic acid of which the sequence is chosen from the sequences SEQ ID NOS. 3, 4 and 6 to 39.

The "spacer chain" denoted [SPAC] in the compound of formula (II) can be of any known type. The function of said spacer chain is to physically distance the nucleic acid from the surface of the solid support on which said compound can be immobilized and to allow a relative mobility of the nucleic acid relative to the surface of the solid support on which it may be immobilized. The spacer chain limits or prevents steric hindrances, due to too great a proximity between the solid support and the nucleic acid, from impairing the binding events between said nucleic acid and coagulation protein molecules that may be brought into contact therewith.

In the compound of formula (II), the spacer chain is preferentially linked to the 5' end or to the 3' end of the nucleic acid aptamer.

Advantageously, the spacer chain is linked both to one end of the aptamer and to the solid support. This construction with a spacer has the advantage of not directly mobilizing the aptamer on the solid support. Preferably, the spacer chain is a nonspecific oligonucleotide or polyethylene glycol (PEG) or another hydrophilic hydrocarbon-based chain. When the spacer chain consists of a nonspecific oligonucleotide, said oligonucleotide advantageously comprises at least 5 nucleotides in length, preferably between 5 and 15 nucleotides in length.

In the embodiments of a compound of formula (II) in which the spacer chain consists of a polyethylene glycol, said spacer chain encompasses a polyethylene glycol of PEG (C18) type, sold, for example, by the company Sigma Aldrich.

As is illustrated in the examples, the purification of active GLA-domain coagulation proteins is carried out both with compounds of formula (II) comprising a spacer chain [SPAC] and with compounds of formula (II) which do not have a spacer chain [SPAC].

In order to immobilize the aptamer on the spacer chain, the nucleic acid may be chemically modified with various chemical groups, such as groups which make it possible to covalently immobilize said nucleic acid, for instance thiols, amines or any other group capable of reacting with chemical groups present on the solid support.

In the compound of formula (II), the compound [IMM] consists of a compound chosen from (i) a compound capable of forming one or more covalent bond(s) with the solid support material and (ii) a compound capable of binding specifically on the solid support by means of weak noncovalent bonds, including hydrogen bonds, electrostatic forces or Van der Waals forces.

In certain cases, the compound [IMM], because it consists of a chain of atoms linked to one another via covalent bonds, can behave as a spacer chain. However, by definition, a compound [IMM] can never signify a [SPAC] chain in a compound of formula (II) according to the invention. In other words, in a compound of formula (II), the [SPAC] chain, when it is present, cannot be directly linked to the chromatography support, whether via covalent bonds or weak noncovalent bonds.

The first type of compound [IMM] encompasses bifunctional coupling agents, such as glutaraldehyde, SIAB or else SMCC.

The SIAB compound, described by G. T. Hermanson (1996, Bioconjugate techniques, San Diego: Academic Press, pp 239-242), is the compound of formula (A) below:

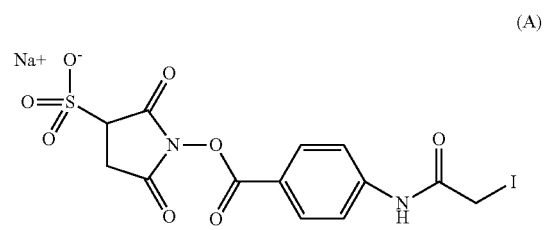 [SMILES: [Na+] ; O=C(CI)Nc1ccc(C(=O)ON2C(=O)CC(S(=O)(=O)[O-])C2=O)cc1]

(A)

The SIAB compound comprises two reactive groups, respectively an iodoacetate group and a sulfo-NHS ester group, these groups reacting respectively with amino and sulfhydryl groups.

The SMCC compound, which is described by M. K. Samoszuk et al. (1989, Antibody, Immunoconjugates Radiopharm., 2(1):37-46), is the compound of formula (B) below:

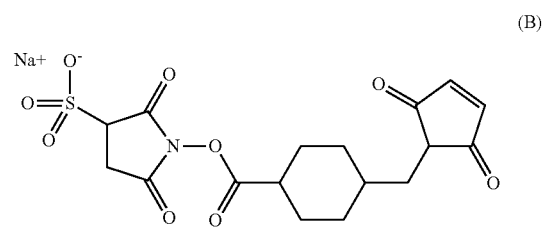 [SMILES: [Na+] ; O=C(ON1C(=O)CC(S(=O)(=O)[O-])C1=O)C1CCC(CC2C(=O)C=CC2=O)CC1]

(B)

The SMCC compound comprises two reactive groups, respectively a sulfo-NHS ester group and a maleimide group, which react respectively with an amino group and a sulfhydryl group.

The second type of compound [IMM] encompasses biotin, which is capable of binding in a specifically noncovalent manner to avidin or streptavidin molecules present on the solid support.

Once immobilized on the solid support via the spacer, the anti-GLA aptamer is advantageously modified at its free end (end not linked to the spacer) by virtue of, and without being limited thereto, a chemically modified nucleotide (such as 2'-O-methyl- or 2'-fluoro-pyrimidine, 2'-ribopurine, phosphoramidite), an inverted nucleotide or a chemical group (PEG, polycations, cholesterol). These modifications make it possible to protect the anti-GLA aptamer against enzymatic degradations.

The solid support may be an affinity chromatography column composed of a gel derived from agarose or cellulose or a synthetic gel such as an acrylamide, methacrylate or polystyrene derivative, a chip such as a chip suitable for surface plasmon resonance, a membrane such as a polyamide, polyacrylonitrile or polyester membrane, or a magnetic or paramagnetic bead.

The present invention also relates to a complex between:
  (i) a nucleic aptamer chosen from a nucleic acid of formula (I), and a compound of formula (II), and
  (ii) an active GLA-domain coagulation protein, including a coagulation protein of which the GLA domain is correctly gamma-carboxylated.

A subject of the present invention is also a support for immobilizing an active GLA-domain coagulation protein, including a coagulation protein with a correctly gamma-carboxylated GLA domain, characterized in that it comprises a solid support material on which a plurality of molecules each consisting of, or each comprising, a nucleic aptamer are grafted, said molecules being chosen from (a) a nucleic acid of formula (I), and (b) a compound of formula (II).

The support above can be used practically in all the applications for which it is sought to immobilize an active GLA-domain coagulation protein, including a human active GLA-domain coagulation protein, which encompasses applications for the purposes of purifying said active GLA-domain coagulation protein and applications for the purposes of detecting said active GLA-domain coagulation protein.

The preparation of supports on which nucleic aptamers of the invention which bind specifically to an active GLA-domain coagulation protein are immobilized, is widely illustrated in the examples, in which the aptamers of the invention are used in particular as capture agents, that can be used for purifying or for detecting an active GLA-domain coagulation protein, including a human active GLA-domain coagulation protein, in samples.

The present invention therefore also relates to a method for immobilizing an active GLA-domain coagulation protein on a support, comprising a step during which a sample comprising at least one GLA-domain protein is brought into contact with a solid support on which a substance chosen from a nucleic acid of formula (I), and a compound of formula (II), has been previously immobilized. Said method may comprise, depending on the technical objectives pursued, an additional step of recovering the immobilized active GLA-domain coagulation protein molecule(s), complexed with the nucleic acid molecules of formula (I). The additional step of recovering the active GLA-domain coagulation protein, or the active GLA-domain coagulation proteins, preferentially consists of a step of bringing the complexes of active GLA-domain coagulation protein(s) with the nucleic acids of formula (I) into contact with a metal-cation-chelating agent, such as EDTA.

For carrying out affinity chromatography protein purification methods using solid supports on which the aptamers of interest are immobilized, those skilled in the art may refer to the work described by Romig et al. (1999, J Chromatogr B Biomed Sci Apl, Vol. 731(2): 275-284).

In addition, the production of an affinity support comprising a nucleic aptamer of the invention and the carrying out of a method for purifying active human Factor IX with said affinity support are illustrated in the examples.

Generally, the solid supports on which the aptamers of the invention can be immobilized encompass any type of support having the structure and the composition commonly found for filter supports, of silicon support for chips, membranes, etc. The solid supports encompass in particular resins, resins for affinity chromatography columns, polymer beads, magnetic beads, etc. The solid supports also encompass in particular glass-based or metal-based materials, such as steel, gold, silver, aluminum, copper, silicon, glass or ceramic. The solid supports also encompass in particular polymer materials, such as a polyethylene, a polypropylene, a polyamide, a polyvinylidene fluoride, and combinations thereof.

The solid support may be coated with a material that facilitates the attachment, the binding, the formation of complexes, the immobilization or the interaction with the aptamers.

In certain embodiments, the solid support is a glass slide of which the surface is coated with a layer of gold, with a layer having undergone a treatment by carboxymethylation, with a layer of dextran, of collagen, of avidin, of streptavidin, etc.

In this way, the aptamers according to the invention can be immobilized on the solid support by means of an attachment coating, for instance described above, or by chemical reaction with the creation of covalent bonds, or by association via noncovalent bonds, such as hydrogen bonds, electrostatic forces, Van der Waals forces, etc.

The examples describe embodiments of solid supports on which the aptamers of the invention are immobilized via noncovalent bonds.

In the examples, solid supports consisting of a glass slide coated with a layer of streptavidin molecules, and aptamers of the invention conjugated to a biotin molecule, which are immobilized on the support by noncovalent biotin/streptavidin association, are in particular described.

In the examples, solid supports consisting of a polystyrene material coated with a layer of streptavidin molecules, and aptamers of the invention conjugated to a biotin molecule, which are immobilized on the support by noncovalent biotin/streptavidin association, are also described.

In certain embodiments, the aptamers of the invention can be immobilized on a solid support suitable for affinity chromatography, electrochromatography and capillary electrophoresis, as described, for example, by Ravelet et al. (2006, J Chromatogr A, Vol. 117(1): 1-10), Connor et al. (2006, J Chromatogr A, Vol. 111(2): 115-119), Cho et al. (2004, Electrophoresis, Vol. 25 (21-22): 3730-3739) or else Zhao et al. (2008, Anal Chem, Vol. 80(10): 3915-3920).

An aptamer of formula (I) which is at least 15 nucleotides in length and which binds specifically to GLA-domain proteins, or a compound of formula (II), can also be advantageously used as an agent for capturing active GLA-domain protein(s) in detection or diagnostic methods and devices.

According to yet another aspect, the present invention also relates to a method for detecting the presence of one or more active GLA-domain coagulation protein(s) in a sample, comprising the following steps:
a) bringing (i) a nucleic acid of formula (I), or a compound of formula (II) or a solid support on which a plurality of molecules of said nucleic acid or of said compound are immobilized, into contact with (ii) said sample; and
b) detecting the formation of complexes between (i) said nucleic acid of formula (I), or said compound of formula (II) or said support, and (ii) the active GLA-domain coagulation protein(s).

The examples of the present patent application provide various embodiments of methods for detecting active human FIX/FIXa with aptamers of the invention immobilized beforehand on a solid support.

For carrying out a detection method according to the invention, the solid support used may be a solid support chosen from the solid supports previously described in relation to the method for purifying active GLA-domain coagulation proteins.

For carrying out a method or preparing a device for detecting active GLA-domain coagulation proteins, those skilled in the art may refer in particular to the techniques described in European patent application No. EP 1 972 693, PCT application No. WO 2008/038696, PCT application No. WO 2008/025830, or else PCT application No. WO 2007/0322359.

In certain embodiments, step b) of detecting the formation of complexes between (i) said nucleic acid or said solid support and (ii) the active GLA-domain coagulation protein(s) can be carried out by measuring the surface plasmon resonance signal, as is described in the examples.

In certain other embodiments, step b) of detecting the formation of complexes between (i) said nucleic acid or said solid support and (ii) the active GLA-domain coagulation protein(s) can be carried out by bringing said complexes optionally formed into contact with a ligand specific for a GLA-domain coagulation protein, said ligand being detectable. The examples describe these embodiments in which use is made, as detectable ligand of a GLA-domain coagulation protein, of anti-GLA-domain coagulation protein monoclonal or polyclonal antibodies labeled with an enzyme, in the case in point horseradish peroxidase, as is conventionally used in tests of ELISA type. As antibodies specific for GLA-domain coagulation proteins, it is possible to use, depending on the objectives that are pursued, (i) either antibodies directed specifically against a predetermined GLA-domain coagulation protein, for example anti-human FII, anti-human FVII, anti-human FIX, anti-human FX, anti-human protein C or anti-human protein S antibodies, (ii) or antibodies directed against a GLA domain, which are capable of recognizing a plurality of GLA-domain proteins, as described, for example, in U.S. Pat. No. 7,439,025.

Surprisingly, it is shown according to the invention that it is possible to produce an affinity support as defined in the present description by using, as anti-GLA nucleic aptamers, DNA aptamers that are nevertheless considered in the prior art to be nucleic acid ligands which are difficult to use and the specificity of which for the target protein is less than the specificity of the RNA molecule of the corresponding sequence. In particular, it is accepted in the prior art that DNA ligands have less flexibility than the corresponding RNA and that, consequently, are less capable than RNA ligands of undergoing conformational changes. It is recalled that, when a nucleic aptamer binds to the target protein, a conformational change takes place. It has also been described that the faster the conformational change of the nucleic aptamer, the higher the affinity of said nucleic aptamer for the target protein (Michaud et al., 2003, Anal Chem, Vol. 76: 1015-1020); Brumbt et al., 2005, Anal Chem, Vol. 77: 1993-1998).

Thus, in certain embodiments of an affinity support according to the invention, the anti-GLA aptamers consist of DNA aptamers.

Consequently, in certain embodiments of an affinity support according to the invention, said immobilized nucleic aptamers, where appropriate included in the structure of a compound of formula (I), consist of deoxyribonucleic acids.

In certain other embodiments of an affinity support according to the invention, a first part of said nucleic acids consists of deoxyribonucleic acids and the remaining part consists of ribonucleic acids.

Another advantage of the nucleic aptamers concerns the ease with which they are produced, compared with the difficulties in synthesizing RNA aptamers, and also their cost price, which is significantly lower than the cost price of an RNA aptamer.

These specific embodiments are illustrated in the examples.

A subject of the present invention is also an affinity chromatography device for purifying an active GLA-domain coagulation protein, or for purifying a plurality of active GLA-domain coagulation proteins, comprising a container in which a suitable amount of an affinity support as defined in the present description is placed.

Varied forms of containers for chromatography supports are known in the prior art and are encompassed by the meaning of the term "container" above. The important characteristics of such a container encompass the presence of a means of feeding the affinity chromatography device with a starting sample and a means for the liquid to leave after it has been brought into contact with the affinity support.

A subject of the present invention is also a method for immobilizing an active GLA-domain coagulation protein on a support, comprising a step during which a sample containing said coagulation protein is brought into contact with an affinity support as defined above.

The starting samples from which one or more active GLA-domain coagulation proteins are purified with an affinity support according to the invention encompass any type of liquid solution in which said active GLA-domain coagulation protein(s) is (are) in suspension or is (are) solubilized. Specific embodiments of such samples, in particular in relation to the purification method described hereinafter, will be defined subsequently in the present description.

In certain preferred embodiments, said sample contains a human active GLA-domain coagulation protein. Advantageously, in these embodiments, the sample containing an active GLA-domain coagulation protein of interest consists of a liquid sample which contains said protein of interest, including a liquid sample comprising said active GLA-domain coagulation protein and which is capable of also containing (i) inactive molecules of said GLA-domain coagulation protein and/or (ii) molecules of the homologous GLA-domain coagulation protein of a nonhuman mammal. In certain embodiments of the purification method above, said sample consists of a biological solution, such as a body fluid, a cell, ground cell material, a tissue, ground tissue material, an organ or a whole organism.

It has been shown in the examples that an anti-GLA aptamer according to the invention makes it possible to purify a recombinant human Factor IX produced in the milk of a pig transgenic for said human Factor IX, owing to the fact that said anti-GLA aptamer binds selectively to the active human Factor IX and (i) does not bind to the inactive human Factor IX and (ii) does not bind to the pig Factor IX, whether said pig Factor IX is active or whether said pig Factor IX is inactive.

In certain embodiments of the purification method above, said sample consists of a liquid biological solution originating from an animal, such as blood, a blood derivative, mammalian milk or a mammalian milk derivative. Said sample may consist of plasma, plasma cryoprecipitate, clarified milk or derivatives thereof.

In particularly preferred embodiments of the purification method above, said sample originates from an animal transgenic for the human GLA-domain coagulation protein of interest. Advantageously, the solution is milk from a mammal or a derivative of milk from a mammal transgenic for said human protein of interest. For the purpose of the invention, the transgenic animals encompass (i) nonhuman mammals such as cows, goats, rabbits, pigs, monkeys, rats or mice, (ii) birds, or else (iii) insects such as mosquitoes, flies or silkworms. In certain preferred embodiments, the animal transgenic for the human protein of interest is a nonhuman transgenic mammal, entirely preferably a doe rabbit transgenic for said human protein of interest. Advantageously, the transgenic mammal produces said recombinant human protein of interest in its mammary glands, owing to the insertion into its genome of an expression cassette comprising a nucleic acid encoding said protein of interest which is placed under the control of a specific promoter allowing the expression of the transgenic protein in the milk of said transgenic mammal.

A method for producing said human GLA-domain protein in the milk of a transgenic animal can comprise the following steps: a DNA molecule comprising a gene encoding the protein of interest, said gene being under the control of a promoter of a protein naturally secreted in milk (such as the casein promoter, the beta-casein promoter, the lactalbumin promoter, the beta-lactoglobulin promoter or the WAP promoter), is integrated into an embryo of a nonhuman mammal. The embryo is then placed in a female mammal of the same species. Once the mammal resulting from the embryo has developed sufficiently, lactation is induced in the mammal, and then the milk is collected. The milk then contains the recombinant human protein of interest.

An example of a method for preparing protein in the milk of a female of a mammal other than a human being is given in document EP 0 527 063, the teaching of which can be reproduced for producing the protein of the invention. A plasmid containing the WAP (Whey Acidic Protein) promoter is produced by introducing a sequence comprising the promoter of the WAP gene, this plasmid being produced in such a way as to be able to receive a foreign gene placed under the control of the WAP promoter. The plasmid containing the promoter and the gene encoding the protein of the invention are used to obtain transgenic doe rabbits, by microinjection into the male pronucleus of doe rabbit embryos. The embryos are then transferred into the oviduct of hormonally prepared females. The presence of the transgenes is revealed by the Southern technique, using the DNA extracted from the young transgenic rabbits obtained. The concentrations in the milk of the animals are evaluated by means of specific radioimmunological tests.

Other documents describe methods for preparing proteins in the milk of a female of a mammal other than a human being. Mention may be made, without being limited thereto, of the documents U.S. Pat. No. 7,045,676 (transgenic mouse) and EP 1 739 170 (production of von Willebrand factor in a transgenic mammal).

The purification method of the invention is also perfectly suitable for obtaining an active GLA-domain coagulation protein purified from a sample of human blood plasma, or from a fraction of human blood plasma, for example the cryoprecipitated fraction of human blood plasma.

In certain embodiments of the purification method above, the target active GLA-domain coagulation protein is human.

In certain embodiments of the purification method above, the sample comprises at least one nonhuman active GLA-domain coagulation protein.

In certain embodiments of the purification method above, said human active GLA-domain coagulation protein is homologous to said nonhuman GLA-domain protein.

In certain embodiments of the purification method above, said human active GLA-domain coagulation protein is the homologue of said nonhuman GLA-domain protein.

In certain embodiments of the purification method above, the starting sample may consist of the crude material, which is either the sample of human blood plasma, or a fraction thereof, or the body fluid of a nonhuman mammal transgenic for the GLA-domain protein of interest, and which contains said GLA-domain protein of interest to be purified. The body fluids of a transgenic nonhuman mammal encompass the milk or a fraction of the milk, for example a defatted fraction of the milk or else a fraction depleted of casein micelles.

However, the embodiment above is not the preferred embodiment of the purification method of the invention, in particular owing to the risk of clogging of the affinity support by the numerous proteins present in the crude starting sample.

In preferred embodiments, said starting sample consists of a liquid solution containing the active GLA-domain coagulation protein of interest in suspension in said solution, said liquid solution consisting of an intermediate product generated during a method for multistep purification of an active GLA-domain coagulation protein.

By way of illustration, for a method for purifying an active GLA-domain coagulation protein from a body fluid of a nonhuman mammal transgenic for said protein, the starting sample may consist of an eluate from a hydrophobic interaction chromatography step, such as a chromatography step in which a chromatographic support of the MEP HyperCel® type is used. This particular embodiment of a purification method according to the invention is illustrated in the examples.

In the same way, for a method for purifying the active GLA-domain coagulation protein of interest from human plasma, the starting sample may consist of a filtrate from a deep-filtration step carried out on the cryoprecipitated fraction of a human plasma sample.

Generally, the conditions for using the affinity support in order to carry out the purification method of the invention are very similar to the conventional conditions for using a conventional chromatography support, for example of the immunoaffinity support type on which ligand antibodies are immobilized. Those skilled in the art may, for example, refer to the handbook by Bailon et al. (Pascal Bailon, George K. Ehrlich, Wen-Jian Fung and Wolfgang Berthold, An Overview of Affinity Chromatography, Humana Press, 2000).

However, as will be detailed in the description that follows, the conditions of elution step c) of the method of the invention are very advantageous for the purification of an active GLA-domain coagulation protein.

In step a), an appropriate volume of the sample to be purified is brought into contact with the affinity support. Complexes are formed between (i) the anti-GLA aptamers immobilized on said affinity support and (ii) the active GLA-domain coagulation protein of interest contained in the sample to be purified.

It has been shown in the examples that the conditions for binding of the anti-GLA aptamers to the active GLA-domain coagulation proteins are promoted in the presence of calcium, for example in the form of calcium chloride.

Thus, in certain embodiments of step a), a buffer solution comprising a final concentration of $CaCl_2$ of at least 1 mM is used, which encompasses at least 2 mM, 3 mM, 4 mM, 5 mM, 6 mM, 7 mM, 8 mM, 9 mM, 10 mM, 11 mM, 12 mM, 13 mM, 14 mM and 15 mM. In step a), a buffer solution comprising a final concentration of $CaCl_2$ of at most 50 mM is advantageously used.

It has also been shown in the examples that the conditions for binding of the anti-GLA aptamers to the active GLA-domain coagulation proteins are promoted in the absence of magnesium chloride.

Thus, in certain embodiments of step a), a buffer solution which does not comprise magnesium chloride is used.

By way of illustration, it has been shown in the examples that, for a chromatography support on which an anti-GLA aptamer according to the invention is immobilized, the affinity of said support for a GLA-domain coagulation protein is increased practically by a factor of ten when a buffer solution devoid of magnesium chloride is used in step a), in the case in point a buffer solution of 50 mM Tris-HCl and CaCl$_2$ at pH 7.5, in comparison with a buffer solution that is identical but comprises magnesium chloride.

In preferred embodiments of the method, at the end of step a) and prior to step b) described in detail later, one or more steps of washing the affinity support are carried out so as to remove the substances which are not specifically retained, for example the substances simply adsorbed onto said support. A conventional washing buffer well known to those skilled in the art can be used.

However, in certain embodiments of the washing step(s), a washing buffer comprising NaCl, and/or ethylene glycol, and/or propylene glycol, and/or ethanol, can be used.

It has been shown in the examples that the use of a washing solution comprising NaCl does not lead to any modification in the specific binding of the GLA-domain coagulation proteins to the immobilized anti-GLA aptamers. It has been shown in particular that a final NaCl concentration of 3M does not disrupt said specific binding.

Thus, in certain embodiments of the washing step(s) prior to step b), a washing solution having a final NaCl concentration of at least 0.5M, which includes at least 1M, 1.5M, 2M, 2.5M and 3M, is used. The final NaCl concentration is advantageously at most 4M.

The results of the examples thus show that the ability of the anti-GLA aptamers of the invention to bind to the GLA-domain coagulation proteins is not modified when the complexes formed between the immobilized aptamers and the GLA-domain protein(s) are subjected to an environment of high ionic strength, this being an entirely unexpected result. It is in fact recalled that it is common to resort to a buffer of high ionic strength as a buffer for eluting substances complexed beforehand to immobilized ligands of an affinity support, including an affinity support comprising immobilized aptamers.

The results of the examples thus show that the anti-GLA aptamers according to the invention have specific and unexpected characteristics with regard to the absence of effect of a high ionic strength on their ability to bind to an active GLA-domain coagulation protein.

Without wishing to be bound by any theory, the applicant thinks that these unexpected properties of the anti-GLA aptamers of the invention are a consequence of the ability of said anti-GLA aptamers to bind specifically to the GLA domain which is common to active GLA-domain coagulation proteins. In particular, the applicant thinks that the anti-GLA aptamers of the invention bind to the target proteins by means of divalent noncovalent bridges which can be generated only at the level of the GLA domain, and that the creation of said divalent bridges prevents the subsequent binding of the ions originating from the NaCl on the GLA domain.

It has also been shown in the examples that the use of a washing solution comprising ethylene glycol does not lead to any modification in the specific binding of the active GLA-domain coagulation proteins to the immobilized anti-GLA aptamers. It has been shown in particular that a final ethylene glycol concentration of 1.5M does not disrupt said specific binding.

Thus, in certain embodiments of the washing step(s) prior to step b), a washing solution having a final ethylene glycol concentration of at least 0.5M, which includes at least 1M and 1.5M, is used.

It has also been shown in the examples that the use of a washing solution comprising propylene glycol does not lead to any modification in the specific binding of the GLA-domain coagulation proteins to the immobilized anti-GLA aptamers. It has been shown in particular that a final propylene glycol concentration of 50% (v/v) does not disrupt said specific binding.

Thus, in certain embodiments of the washing step(s) prior to step b), a washing solution having a final propylene glycol concentration of at least 10% (v/v), which includes at least 15%, 20%, 25%, 30%, 35%, 40%, 45% and 50%, is used.

It has also been shown in the examples that the use of a washing solution comprising ethanol does not lead to any modification in the specific binding of the active GLA-domain coagulation proteins to the immobilized anti-GLA aptamers. It has been shown in particular that a final ethanol concentration of 10% (v/v) does not disrupt said specific binding.

Thus, in certain embodiments of the washing step(s) prior to step b), a washing solution having a final ethanol concentration of at least 1% (v/v), which includes at least 1.5%, 2.0%, 2.5%, 3.0%, 3.5%, 4.0%, 4.5%, 5.0%, 5.5%, 6.0%, 6.5%, 7.0%, 7.5%, 8.0%, 9.0%, 9.5% and 10.0%, is used.

It has been shown that such a washing buffer leads to drastic conditions for removing the substances that are not specifically retained on the aptamers, while at the same time preserving the specific binding of the molecules of the active GLA-domain coagulation protein(s) to the aptamers immobilized on the affinity support. It is recalled that such a technical advantage linked to the exclusive or virtually exclusive removal of the substances not specifically bound to the ligands immobilized on the affinity support cannot be easily realized with an affinity support on which antibodies are immobilized.

Step b) consists of a step of eluting the molecules of the active GLA-domain coagulation protein of interest having formed complexes with the anti-GLA nucleic aptamers during step a).

As is illustrated in the examples, a specific advantage of the purification method above is the possibility of carrying out the elution step by bringing the complexes formed between (i) the anti-GLA nucleic aptamers immobilized on said affinity support and (ii) said active GLA-domain coagulation protein into contact with a divalent-ion-chelating agent, such as EDTA.

This technical advantage, which is made possible by virtue of the characteristics of the affinity support of the invention, makes it possible to elute the active GLA-domain coagulation protein without requiring any recourse to the use of drastic elution conditions, that may denature, at least partially, the active GLA-domain coagulation protein of interest. Said drastic conditions which are avoided encompass the use of an acidic pH for the elution step, which is commonly performed for the methods for purifying proteins on affinity supports that are known, and most particularly on affinity supports comprising immobilized antibodies.

Thus, in certain embodiments of the purification method above, step b) is carried out by bringing the affinity support into contact with an elution buffer containing a divalent-ion-chelating agent, preferably EDTA.

By way of illustration, the elution buffer may contain a final EDTA concentration of at least 1 mM and of at most 100 mM.

The expression "at least 1 mM" encompasses at least 2, 3, 4, 5, 6, 7, 8, 9 or 10 mM.

The expression "at most 100 mM" encompasses at most 29, 28, 27, 26, 25, 24, 23, 22, 21, 20, 19, 18, 17, 16, 15, 14, 13, 12 or 11 mM.

In step c), the active GLA-domain protein of interest is purified by collecting the eluate liquid obtained at the end of step b).

At the end of step c), a purified liquid composition of the coagulation protein of interest is obtained. Said purified liquid composition can then be treated appropriately, according to any known technique for conditioning and storing proteins, including by direct bottling or bottling after dilution with a suitable solution, or else by freeze-drying, preferentially under sterile and apyrogenic conditions, and then storage under appropriate conditions, at ambient temperature, at −4° C. or else at a low temperature, depending on the type of conditioning selected.

As has already been mentioned previously in the present description, the affinity support of the invention can, with the successive cycles of use for purifying an active GLA-domain coagulation protein of interest, experience a reduction in its absorption capacity, for example owing to the fact that elution step c) does not make it possible to systematically release all of the molecules of coagulation protein, thereby reducing the number of free aptamer sites for the subsequent purification cycles.

As for all known chromatography supports, it is therefore necessary, at appropriate moments, to carry out a step of regenerating the affinity support, in order to release all of the molecules of active GLA-domain coagulation protein from said support, and to remove any substance that may be bound to the solid material of the affinity support, generally by nonspecific binding.

Thus, in certain embodiments, the purification method of the invention comprises an additional step d) of regenerating the affinity support by bringing said affinity support into contact with a regenerating solution.

Varied buffers for regenerating chromatography supports, in particular affinity chromatography supports, are well known to those skilled in the art, and can be used in step d) of the method. Those skilled in the art may refer, for example, to the handbook by Mohr et al. (Affinity Chromatography: Practical and Theoretical Aspects, Peter Mohr, Klaus Pommerening, Edition: illustrated, CRC Press, 1985).

By way of illustration, step d) of regenerating the affinity support can be carried out by bringing said support into contact with a buffer solution of 20 mM Tris, 5% polyethylene glycol and 1M NaCl, for example at pH 7.5, as is illustrated in the examples.

The purification method above makes it possible to obtain an active GLA-domain coagulation protein at a very high degree of purity, optionally at a degree of purity greater than 99.95% by weight, relative to the total weight of the proteins contained in the purified final product.

Another advantage of the purification method above, in particular in the embodiments in which the starting sample consists of a sample comprising the human active GLA-domain coagulation protein of interest in recombinant form as a mixture with proteins naturally produced by the non-human transgenic mammal, is that the final composition comprising the recombinant human protein of interest at a high degree of purity is substantially free of proteins originating from said transgenic mammal, and in particular substantially free of proteins of said mammal which are homologues of said recombinant human active GLA-domain coagulation protein.

The present invention also relates to a nucleic aptamer which binds specifically to biologically active GLA-domain proteins, of which the ability to bind to a target GLA-domain protein is not modified by an environment of high ionic strength.

The invention relates in particular to a nucleic aptamer which binds specifically to biologically active GLA-domain proteins, of which the ability to bind to a target biologically active GLA-domain protein is not modified by an environment of high ionic strength having a final NaCl concentration of at least 0.5M.

The biologically active GLA-domain proteins encompass biologically active GLA-domain coagulation proteins.

Said "environment" at high ionic strength encompasses a buffer solution at high ionic strength.

An environment of high ionic strength includes an environment having a final NaCl concentration of at least 1M, 1.5M, 2M, 2.5M and 3M. The final NaCl concentration is advantageously at most 4M.

The expression "is not modified" means that the binding between the target GLA-domain protein and the nucleic aptamer which binds specifically to biologically active GLA-domain proteins withstands an environment of high ionic strength. For example, at least 80% of the target biologically active GLA-domain proteins remain bound to the nucleic aptamer which binds specifically to biologically active GLA-domain proteins in an environment at high ionic strength, preferably 85%, 90%, 95%, 96%, 97%, 98%. In particular, this means that a washing step in an environment of high ionic strength does not result in the elution of more than 20% of the biologically active GLA-domain proteins bound to the nucleic aptamer which binds specifically to biologically active GLA-domain proteins, preferably of more than 10%, 5%, 4%, 3%, 2%, 10.

In one particular embodiment, the nucleic aptamer according to the invention also has the ability to bind to a target biologically active GLA-domain protein without being modified by a hydrophobic environment, such as a 10% ethanol or 50% propylene glycol solution.

These properties can advantageously be used for very efficiently washing an affinity support on which a nucleic aptamer according to the invention is immobilized, thereby making it possible to obtain better removal of the contaminants nonspecifically bound to the column. The improvement in the washing efficiency makes it possible to increase the purity of the biologically active GLA-domain proteins that it is sought to purify.

As has been described previously in the present description and is also illustrated in the examples, the complexes formed between the nucleic aptamers of the invention and the target biologically active GLA-domain proteins can be dissociated by bringing said complexes into contact with a solution comprising a divalent-ion-chelating agent, for example EDTA. Thus, according to another of their characteristics, the nucleic aptamers of the invention consist of nucleic aptamers which allow the formation of complexes with target GLA-domain proteins, it being possible for said complexes to be dissociated, with release of the target biologically active GLA-domain proteins, by bringing said complexes into contact with a medium comprising a divalent-ion-chelating agent, for example EDTA.

As already specified previously, a complex between a nucleic aptamer of the invention and a target biologically active GLA-domain protein can be dissociated by bringing said complex into contact with a medium, including a buffer solution, comprising a final EDTA concentration of at least 1 mM and of at most 100 mM.

As is illustrated in the examples, advantage is taken of the ability of certain embodiments of the anti-GLA aptamers of the invention to bind to a diversity of active GLA-domain coagulation proteins, for example to a diversity of human active GLA-domain coagulation proteins, for simultaneously purifying a plurality of active GLA-domain coagulation proteins that may be contained in the starting sample, using a single affinity chromatography support. For example, use may be made of the process for purifying a GLA-domain protein above for simultaneously purifying several GLA-domain coagulation factors contained in the starting sample, for example for simultaneously purifying the Factors VII, IX and X contained in a cryoprecipitated fraction of human blood plasma.

A subject of the present invention is also a purified composition of a recombinant human active GLA-domain coagulation protein comprising at least 99.9% by weight of said recombinant human active GLA-domain protein and which is substantially free of nonhuman proteins.

The present invention also relates to a purified composition of a recombinant human active GLA-domain coagulation protein comprising at least 99.9% by weight of said recombinant human GLA-domain protein and at most 0.1% by weight of nonhuman proteins, the percentages by weight being expressed relative to the total weight of proteins of said purified composition.

In the purified composition above, "at least 99.9%" encompasses at least 99.91%, 99.92%, 99.93%, 99.94%, 99.95%, 99.96%, 99.97%, 99.98% and 99.99%.

In the purified composition above, "at most 0.1%" encompasses at most 0.09%, 0.08%, 0.07%, 0.06%, 0.05%, 0.04%, 0.03%, 0.02% and 0.01%.

The present invention also relates to a purified composition as defined above, that can be used as a medicament.

The invention also relates to a pharmaceutical composition comprising a purified composition of a recombinant human active GLA-domain coagulation protein as defined above, in combination with one or more pharmaceutically acceptable excipients.

The invention also relates to a purified composition as defined above, for treating coagulation disorders.

The invention also relates to the use of a purified composition as defined above, for producing a medicament for treating coagulation disorders.

Methods for Obtaining Anti-GLA Aptamers

Generally, an anti-GLA aptamer according to the invention can be obtained according to a method based on the general principles of the technique known as SELEX (Systematic Evolution of Ligands by Exponential Enrichment), which was initially described in particular in PCT application No. WO 1991/019813. The SELEX method for selecting aptamers consists in bringing a protein into contact with a combinatorial library of nucleic acids, DNA or RNA (in general $10^{15}$ molecules); the nucleic acids which do not bind to the target are removed, the nucleic acids which bind to the target are isolated and amplified by PCR. The method is repeated until the solution is sufficiently enriched with the nucleic acids having good affinity for the protein of interest (Tuerk and Gold, "Systematic evolution of ligands by exponential enrichment: RNA ligands to bacteriophage T4 DNA polymerase" (1990) Science, 249(4968): 505-10 and Ellington and Szostak, "In vitro selection of RNA molecules that bind specific ligands", (1990) Nature August 30; 346(6287): 818-22). Other SELEX method examples are given in documents EP 0 786 469, EP 668 931, EP 1 695 978 and EP 1 493 825, the teachings of which can be reproduced in carrying out the method for selecting a nucleic aptamer used according to the invention. Certain variants of the SELEX method comprise steps of counterselection of aptamers previously selected by binding to the target protein of interest. The counterselection step(s) can consist of a step in which a collection of aptamers, which has previously been selected with the target protein of interest, is brought into contact with non-target molecules, so as to remove, from the starting collection of aptamers, those which bind to the non-target molecules. The implementation of such a counterselection step, in a method for obtaining nucleic aptamers, is capable of increasing the specificity or the affinity of the aptamers selected at the end of the method.

A first method for obtaining an anti-GLA aptamer can consist of a method comprising the following steps:

a) providing a mixture of nucleic acids, also called "collection" of nucleic acids having distinct sequences, b) bringing the mixture of nucleic acids provided in step a), or the mixture of nucleic acids obtained at the end of step d) when step b) is repeated, into contact with a first target active GLA-domain coagulation protein, under conditions which allow the formation of complexes between nucleic acids of said mixture and said first target GLA-domain coagulation protein, c) carrying out a separation between (i) the nucleic acid(s) having formed complexes with said first target active GLA-domain coagulation protein and (ii) the nucleic acids not having formed complexes with said first target active GLA-domain coagulation protein, d) amplifying the nucleic acids having formed complexes with said first target active GLA-domain coagulation protein, so as to obtain a mixture or a collection of nucleic acids which bind to said first target active GLA-domain coagulation protein, e) repeating steps b) to d) a sufficient number of times to obtain a collection of nucleic acids having the desired ability to bind to said first target active GLA-domain coagulation protein, f) bringing the mixture of nucleic acids provided in step e), or the mixture of nucleic acids obtained at the end of step h) when step f) is repeated, into contact with a second target active GLA-domain coagulation protein, under conditions which allow the formation of complexes between nucleic acids of said mixture and said second target active GLA-domain coagulation protein, g) carrying out a separation between (i) the nucleic acid(s) having formed complexes with said second target active GLA-domain coagulation protein and (ii) the nucleic acids not having formed complexes with said second target active GLA-domain coagulation protein, h) amplifying the nucleic acids having formed complexes with said second target active GLA-domain coagulation protein, so as to obtain a mixture or a collection of nucleic acids which bind to said second target active GLA-domain coagulation protein, i) repeating steps f) to h) a sufficient number of times to obtain a collection of nucleic acids having the desired ability to bind to said second target active GLA-domain coagulation protein, said nucleic acids having the ability to bind both to said first target active GLA-domain coagulation protein and to the second target active GLA-domain coagulation protein, j) optionally, repeating steps f) to i) with one or more other distinct target active GLA-domain coagulation proteins, so as to obtain, at the end of the method, a mixture or a collection of nucleic acids termed "anti-GLA aptamers" having the ability to bind to the active GLA-domain coagulation proteins.

The nucleic aptamers which are obtained at the end of step j) of the method above are capable of binding selectively to active GLA-domain coagulation proteins and do not bind to the other proteins, and in particular do not bind to the inactive GLA-domain coagulation proteins.

Generally, the detailed protocols for implementing the steps of the method above can be found by those skilled in the art in the numerous publications relating to the SELEX technique, including in the references previously cited in the present description.

In certain embodiments of the method for obtaining anti-GLA aptamers above, from 2 to 6 target active GLA-domain coagulation proteins are successively used for selecting anti-GLA aptamers, i.e. nucleic aptamers specific for active GLA-domain coagulation proteins, but not specific for a given active GLA-domain coagulation protein. In practice, it has been shown that the successive use, in the method above, of 2 distinct target active GLA-domain coagulation proteins makes it possible to obtain anti-GLA aptamers.

For implementing the method for obtaining anti-GLA aptamers above, the target active GLA-domain coagulation proteins can be chosen from the group consisting of Factor II, Factor VII, Factor IX, Factor X, protein C and protein S. The order in which the target proteins is used is not an essential characteristic of the method above.

According to an alternative, the anti-GLA nucleic aptamers can be obtained according to a second method comprising the following steps:
- a) providing a mixture of nucleic acids, also called "collection" of nucleic acids having distinct sequences,
- b) bringing the mixture of nucleic acids provided in step a), or the mixture of nucleic acids obtained at the end of step d) when step b) is repeated, into contact with the GLA domain of a first target active GLA-domain coagulation protein, under conditions which allow the formation of complexes between nucleic acids of said mixture and the GLA domain of said first target active GLA-domain coagulation protein,
- c) carrying out a separation between (i) the nucleic acid(s) having formed complexes with the GLA domain of said first target active GLA-domain coagulation protein and (ii) the nucleic acids not having formed complexes with the GLA domain of said first target active GLA-domain coagulation protein,
- d) amplifying the nucleic acids having formed complexes with the GLA domain of said first target active GLA-domain coagulation protein, so as to obtain a mixture or a collection of nucleic acids which bind to the GLA domain of said first target active GLA-domain coagulation protein,
- e) repeating steps b) to d) a sufficient number of times to obtain a collection of nucleic acids having the desired ability to bind to the GLA domain of said first target active GLA-domain coagulation protein,
- f) bringing the mixture of nucleic acids provided in step e), or the mixture of nucleic acids obtained at the end of step h) when step f) is repeated, into contact with the GLA domain of a second target active GLA-domain coagulation protein, under conditions which allow the formation of complexes between nucleic acids of said mixture and the GLA domain of said second target active GLA-domain coagulation protein,
- g) carrying out a separation between (i) the nucleic acid(s) having formed complexes with the GLA domain of said second target active GLA-domain coagulation protein and (ii) the nucleic acids not having formed complexes with the GLA domain of said second target active GLA-domain coagulation protein,
- h) amplifying the nucleic acids having formed complexes with the GLA domain of said second target active GLA-domain coagulation protein, so as to obtain a mixture or a collection of nucleic acids which bind to the GLA domain of said second target active GLA-domain coagulation protein,
- i) repeating steps f) to h) a sufficient number of times to obtain a collection of nucleic acids having the desired ability to bind to the GLA domain of said second target active GLA-domain coagulation protein, said nucleic acids having the ability to bind both to the GLA domain of said first target active GLA-domain coagulation protein and to the GLA domain of the second target active GLA-domain coagulation protein,
- j) optionally, repeating steps f) to i) with the GLA domain of one or more other distinct target GLA-domain proteins, so as to obtain, at the end of the method, a mixture or a collection of nucleic acids termed "anti-GLA aptamers" having the ability to bind to the active GLA-domain coagulation proteins.

The nucleic aptamers which are obtained at the end of step j) of the method above are capable of binding selectively to active GLA-domain coagulation proteins and do not bind to the other proteins, and in particular do not bind to the inactive GLA-domain coagulation proteins.

In certain embodiments of the second method for obtaining anti-GLA aptamers above, the GLA domains originating from 2 to 6 target active GLA-domain coagulation proteins are successively used for selecting anti-GLA aptamers.

For implementing the second method for obtaining anti-GLA aptamers above, the target active GLA-domain coagulation proteins from which the GLA domains used originate can be chosen from the group consisting of Factor II, Factor VII, Factor IX, Factor X, protein C and protein S. The order in which the target GLA domains are used is not an essential characteristic of the method above.

The essential difference between the second method for obtaining anti-GLA aptamers above and the first method for obtaining anti-GLA aptamers previously described lies in the target, which consists of a succession of target active GLA-domain coagulation proteins in the first method and consists of a succession of GLA domains of active GLA-domain coagulation proteins in the second method.

According to the invention, anti-GLA aptamers, which bind to a plurality of active GLA-domain coagulation proteins, can be obtained according to a third method, the principles of which are identical to the first and second methods described above, but in which the target substances are alternately active GLA-domain coagulation proteins and GLA domains of active GLA-domain coagulation proteins. The order in which the active GLA-domain coagulation proteins and the GLA domains of active GLA-domain coagulation proteins are used is easily determined by those skilled in the art, according in particular to the target substances to which said person skilled in the art has access.

The target GLA domains which are used in each of the second and third methods above can be easily obtained by those skilled in the art, in particular in situations in which the amino acid sequence of the parent GLA-domain coagulation protein, and therefore also the amino acid sequence of the GLA domain under consideration, are known.

According to certain embodiments, a GLA domain is obtained from the parent GLA-domain coagulation protein by proteolysis of said GLA-domain protein, using one or more suitable proteolytic enzymes of known cleavage specificity.

According to other embodiments, a GLA domain is obtained by peptide synthesis techniques known per se, on the basis of their known amino acid sequence, and then by gamma-carboxylation of the glutamate residues of the GLA domain, using a carboxylase, according to techniques well known to those skilled in the art. By way of illustration, a peptide comprising the GLA domain of a GLA domain coagulation protein can be synthesized with a peptide synthesizer apparatus of the Milligen® 9050 Plus type (Perkin Elmer, Stockholm, Sweden), for example using DPfp Fmoc amino acids sold by the company PerSeptive Biosystems® (Framingham, Mass., United States). For the step of enzymatic gamma-carboxylation of the neosynthesized GLA domain, use may, for example, be made of a semi-purified carboxylase as described by Soute et al. (1987, Thrombo Haemostasis, Vol. 57: 77-81), according to the technique described by Wu et al. (1990, J Biol Chem, Vol. 265(22): 13124-13129).

Other anti-GLA aptamers of the invention, which bind selectively to a single active GLA-domain coagulation protein, can also be obtained according to other methods which are described below, which also consist of processes of which the principle is based on the implementation of protocols used for the SELEX technique.

According to the invention, a fourth method for obtaining anti-GLA aptamers which bind selectively to a single active GLA-domain coagulation protein has been developed, which method comprises (i) one or more steps of selecting nucleic acids which bind to an active GLA-domain coagulation protein, and (ii) one or more steps of counterselection in order to remove (ii-a) the nucleic acids which bind to the inactive form of said GLA-domain coagulation protein, and/or (ii-b) the nucleic acids which bind to other GLA-domain coagulation proteins. It is specified that the fourth method below comprises one or more steps of counterselection of nucleic acids previously selected for binding to the active GLA-domain coagulation protein of interest. However, the counterselection step(s), or else one or more additional counterselection steps, can be provided for prior to step a) of the method below.

Thus, a fourth method for obtaining anti-GLA aptamers consists of a method comprising the following steps:
a) providing a mixture of nucleic acids, also called "collection" of nucleic acids having distinct sequences, said collection of nucleic acids optionally having been obtained at the end of one or more counterselection steps as described above,
b) bringing the mixture of nucleic acids provided in step a), or the mixture of nucleic acids obtained at the end of step d) when step b) is repeated, into contact with a first target active GLA-domain coagulation protein, under conditions which allow the formation of complexes between nucleic acids of said mixture and the GLA domain of said first target active GLA-domain coagulation protein,
c) carrying out a separation between (i) the nucleic acid(s) having formed complexes with said first target active GLA-domain coagulation protein and (ii) the nucleic acids not having formed complexes with said first target active GLA-domain coagulation protein,
d) amplifying the nucleic acids having formed complexes with said first target active GLA-domain coagulation protein, so as to obtain a mixture or a collection of nucleic acids which bind to said first target active GLA-domain coagulation protein,
e) repeating steps b) to d) a sufficient number of times to obtain a collection of nucleic acids having the desired ability to bind to said first target active GLA-domain coagulation protein,
f) bringing the mixture of nucleic acids obtained at the end of step d), or at the end of step e) when steps b) to d) are repeated, into contact with an inactive form of said first target GLA-domain coagulation protein, under conditions which allow the formation of complexes between nucleic acids of said mixture and said first target inactive GLA-domain coagulation protein,
g) carrying out a separation between (i) the nucleic acid(s) having formed complexes with said inactive form of said target GLA-domain coagulation protein and (ii) the nucleic acids not having formed complexes with said inactive form of said target GLA-domain coagulation protein,
h) amplifying the nucleic acids not having formed complexes with said inactive form of said target GLA-domain coagulation protein, so as to obtain a mixture or a collection of nucleic acids which bind to said active form of said first GLA-domain coagulation protein and which do not bind to said inactive form of said GLA-domain coagulation protein,
i) repeating steps f) to h) a sufficient number of times to obtain a collection of nucleic acids having the desired ability to bind to said target active GLA-domain coagulation proteins.

In the fourth method for obtaining anti-GLA aptamers above, steps b) to e) consist of steps for selecting nucleic acids which bind to the active GLA-domain coagulation protein of interest. In said fourth method, steps f) to i) consist of counterselection steps, during which those of the nucleic acids which also bind to the inactive forms of the active GLA-domain coagulation protein of interest are removed from the collection of nucleic acids selected in steps b) to e) for their ability to bind to the active GLA-domain coagulation protein of interest.

For implementing a SELEX-type method comprising one or more steps of counterselection against a non-target protein, those skilled in the art may refer in particular to the general teaching and also to the technical protocols described in U.S. Pat. No. 5,580,737.

In certain embodiments of fourth method for the obtaining anti-GLA aptamers counterselection above, steps f) to i) can be carried out with various inactive forms of a single GLA-domain coagulation protein of interest, for instance a protein comprising a GLA domain in which successively one GLA residue and then more than one GLA residue is not gamma-carboxylated and is therefore present in the GLA domain as a glutamate residue. By way of illustration, in order to implement successive counterselection steps, it is possible to successively use forms of the protein of interest comprising a GLA domain in which, successively, 1, 2, 3, 4, 5, 6, 7, 8, 9, 10, 11 or 12 GLA residues are present as glutamate residues, the number of GLAs present as GLU being of course limited by the maximum number of GLA residues that can be present in the GLA domain under consideration when it is completely gamma-carboxylated.

In order to implement the fourth method for obtaining anti-GLA aptamers above, the GLA-domain coagulation proteins can be chosen from the group consisting of Factor II, Factor VII, Factor IX, Factor X, protein C and protein S.

Other alternatives of a method for selecting aptamers which bind specifically to active GLA-domain coagulation proteins can be easily developed by those skilled in the art, including selection methods that include one or more initial counterselection step(s) using inactive GLA-domain coagulation proteins, followed by one or more selection step(s) in which active GLA-domain coagulation proteins are used.

According to yet other embodiments, a method for obtaining an anti-GLA aptamer may be of the type of any one of the methods described above, to which may be added a step of selecting those of the aptamers of which the ability to bind to the target protein is not modified by an environment of high ionic strength, for example a buffer solution comprising NaCl at a final concentration of at least 0.5M, which includes at least 1M, 1.5M, 2M, 2.5M and 3M.

According to yet other embodiments, a method for obtaining an anti-GLA aptamer may be of the type of any one of the methods described above, to which may be added a step of selecting those of the aptamers which allow the formation of complexes with target GLA-domain proteins, it being possible for said complexes to be dissociated, with release of the target GLA-domain proteins, by bringing said complexes into contact with a medium comprising a divalent-ion-chelating agent, for example EDTA. The step of selecting these aptamers can be carried out with a medium, including a buffer solution, comprising a final EDTA concentration of at least 1 mM and at most 100 mM.

According to yet other embodiments, a method for obtaining an anti-GLA aptamer may be of the type of any one of the methods described above, to which may be added a step of selecting those of the aptamers of which the ability to bind the target protein is not modified by the presence of an alkylene glycol or of a polyalkylene glycol.

According to yet other embodiments, a method for obtaining an anti-GLA aptamer may be of the type of any one of the methods described above, to which may be added a step of selecting those of the aptamers of which the ability to bind to the target protein is not modified by the presence of ethylene glycol. The step of selecting these aptamers may be carried out with a medium, including a buffer solution, comprising a final ethylene glycol concentration of at least 0.5M, which includes at least 1M and 1.5M.

According to yet other embodiments, a method for obtaining an anti-GLA aptamer may be of the type of any one of the methods described above, to which may be added a step of selecting those of the aptamers of which the ability to bind to the target protein is not modified by the presence of propylene glycol. The step of selecting these aptamers may be carried out with a medium, including a buffer solution, comprising a final propylene glycol concentration of at least 10% (v/v), which includes at least 15%, 20%, 25%, 30%, 35%, 40%, 45% and 50%.

According to yet other embodiments, a method for obtaining an anti-GLA aptamer may be of the type of any one of the methods described above, to which may be added a step of selecting those of the aptamers of which the ability to bind to the target protein is not modified by the presence of ethanol. The step of selecting these aptamers may be carried out with a medium, including a buffer solution, comprising a final ethanol concentration of at least 1% (v/v), which includes at least 1.5%, 2.0%, 2.5%, 3.0%, 3.5%, 4.0%, 4.5%, 5.0%, 5.5%, 6.0%, 6.5%, 7.0%, 7.5%, 8.0%, 9.0%, 9.5% and 10.0%.

Methods for Determining the Biological Activity of GLA-Domain Coagulation Proteins Generally, the determination of the biological activity of the GLA-domain coagulation proteins is commonly carried out in a manner known to those skilled in the art according to either of two types of tests, respectively (i) a test for determining the anticoagulant activity which takes advantage of the measurement of the property of the coagulation protein under consideration of restoring the coagulant activity of a plasma initially devoid of said coagulation protein, and (ii) a test for determining the actual enzymatic activity of the coagulation protein under consideration, by measuring the conversion of a chromogenic substrate. The general principles of these two types of determination of the biological activity of a GLA-domain coagulation protein are described below, as is their specific application to the biological determination of the GLA-domain coagulation proteins of interest.

It is specified that the results of the measurements for determining the biological activity of a GLA-domain coagulation protein are comparable for a given test protein, regardless of the test used, insofar as the results are expressed as a ratio between (i) the biological activity of the protein tested and (ii) the biological activity of an active reference protein.

According to the invention, the reference composition may consist of a plasma concentrate, preferentially a human plasma concentrate, or else a composition comprising a recombinant GLA-domain coagulation protein.

Determination of the Biological Activity of a GLA-Domain Coagulation Protein by Measuring the Coagulant Activity This first method consists in introducing the test coagulation factor into a plasma initially devoid of this factor, then measuring the percentage restoration of the anticoagulant activity relative to a normal plasma. Plasmas specifically depleted of each of the coagulation factors are commercially available, for example through companies such as Stago, American Diagnostica or Hyphen Biomed.

The activity of a plasma is characterized by a coagulation time, i.e. by a time which is necessary to form fibrin molecules which polymerize with one another and solidify the plasma. This modification of the mechanical properties of the plasma can be measured simply using coagulometer devices. Coagulometer devices have a small magnetic bar, the movement of which is stopped at the time of coagulation.

If the test coagulation factor is a procoagulant factor, the addition of this factor to a plasma initially depleted of this factor will cause a decrease in the coagulation time, which time will be close to that of a normal plasma. This type of method makes it possible to verify most of the functionalities of coagulation factors, such as: enzymatic activity, target and cofactor recognition, with the exception of the abilities to interact with blood cells and the endothelial cells of the blood vessel walls. This type of method gives an overall and averaged picture of the activities of the GLA-domain coagulation factors to be tested.

Generally, the first method for determining the biological activity of a GLA-domain coagulation protein consists of a method which comprises the following steps:
a) providing
  (i) a test composition comprising a GLA-domain coagulation protein,
  (ii) a plurality of samples prepared from a reference composition comprising a known amount of said biologically active GLA-domain protein, each sample comprising a known amount of said biologically active GLA-domain protein, distinct from the amount of said protein contained in each of the other samples,
  (iii) a composition of plasma depleted of said GLA-domain protein or a composition of plasma free of said GLA-domain protein and, if necessary,
  (iv) one or more purified cofactor(s) of said GLA-domain protein,
b) beginning the assay by carrying out the following steps b1) and b2):
  b1) bringing (i) the test composition comprising a GLA-domain coagulation protein into contact with (ii) the composition of plasma depleted of said GLA-domain protein or the composition of plasma free of said GLA-domain protein and, if necessary, also with (iii) one or more purified cofactor(s) of said GLA-domain protein, b2) bringing (i) each sample of the reference composition comprising a known amount of said biologically active GLA-domain protein into contact with (ii) the composition of plasma depleted of said GLA-domain protein or the composition of plasma free of said GLA domain protein and, if necessary, also with (iii) one or more purified cofactor(s) of said GLA-domain protein, c) determining:
  c1) for the test composition, the time that elapses between the beginning of step b1) and the moment at which the mixture prepared in step b1) with the test composition is coagulated, and
  c2) for each sample of the reference composition, the time that elapses between the beginning of step b2) and the moment at which the mixture prepared in step b2) with the reference composition is coagulated, d) preparing a calibration curve, also called reference curve, with the time measurements determined in step c2) as a function of the known amount of said GLA-domain coagulation protein in each sample, e) determining the amount of said GLA-domain coagulation protein contained in the test composition, by determining, on the calibration curve prepared in step d), and on the basis of the time determined in step c1), the deduced amount of said GLA-domain coagulation protein in the test composition.

Determination of the Biological Activity of Factor II (Prothrombin)

In step a)-(i), the test composition which comprises Factor II is provided.

In step a)-(ii), a plurality of samples of the reference Factor II composition are provided, for example in the form of samples of successive dilutions of a basic reference composition. It is, for example, possible to use a first sample of the reference composition (100%), then successive dilutions to 50%, 25%, 12.5% and 6.2% of the reference composition.

In step a)-(iii), a Factor II-depleted plasma composition is provided, for example the composition sold by the company American Diagnostica Inc. (Stanford, USA) under the reference No. 202.

For carrying out the method, those skilled in the art may refer to the test sold by the company Hyphen Biomed under the reference No. DP010K or the test sold by the company Hyphen Biomed under the reference No. DP010A.

For carrying out the method, those skilled in the art may refer to the following articles: Soulier et al. (1952, Sang, Vol. 23: 549-559), Favre-Gilly et al. (1967, Cah Med Lyonnais, Vol. 43(28): 2611-2668), Gjonaess et al. (Acta Obste Gynecol Scand, Vol. 54: 363-367) or Andrew et al. (1987, Blood, Vol. 70: 165-172).

Determination of the Biological Activity of Factor VII

In step a)-(i), the test composition which comprises Factor VII is provided.

In step a)-(ii), a plurality of samples of the reference Factor VII composition are provided, for example in the form of samples of successive dilutions of a basic reference composition. It is, for example, possible to use a first sample of the reference composition (100%), then successive dilutions to 50%, 25%, 12.5% and 6.2% of the reference composition. A plasma concentrate sold by the National Institute for Biological Standards and Control (NIBSC-United Kingdom) under the reference No. 97/592 can be used as reference composition.

In step a)-(iii), a Factor VII-depleted plasma composition is provided, for example the composition sold by the company American Diagnostica Inc. (Stanford, USA) under the reference No. 267.

For carrying out the method, those skilled in the art may refer to the test sold by the company Hyphen Biomed under the reference No. DP030K or the test sold by the company Hyphen Biomed under the reference No. DP030A.

For carrying out the method, those skilled in the art may refer to the following articles: Soulier et al. (1952, Sang, Vol. 23: 549-559) or Gjonaess et al. (Acta Obste Gynecol Scand, Vol. 54: 363-367).

Determination of the Biological Activity of Factor IX

In step a)-(i), the test composition which comprises Factor IX is provided.

In step a)-(ii), a plurality of samples of the reference Factor IX composition is provided, for example in the form of samples of successive dilutions of a basic reference composition. It is, for example, possible to use a first sample of the reference composition (100%), then successive dilutions to 50%, 25%, 12.5% and 6.2% of the reference composition. A plasma concentrate sold by the National Institute for Biological Standards and Control (NIBSC-United Kingdom) under the reference No. 07/182 can be used as reference composition.

In step a)-(iii), a Factor IX-depleted plasma composition is provided, for example the composition sold by the company American Diagnostica Inc. (Stanford, USA) under the reference No. 269.

For carrying out the method, those skilled in the art may refer to the test sold by the company Hyphen Biomed under the reference No. DP050K or the test sold by the company Hyphen Biomed under the reference No. DP050A.

For carrying out the method, those skilled in the art may refer to the following articles: Van Hylckama et al. (2000, Blood, Vol. 95(12): 3678-3682), Taran et al. (1997, Biochemistry (Mosc.), Vol. 62(7): 685-693), Orstavik et al. (1979, Br J Haematol, Vol. 42(2): 293-301), and also to the document available at the following internet address: "www.ncbi.nlm.nih.gov" (OMIM, Haemophilia B, FIX deficiency, +306900, +134540, +134510, +134520).

Determination of the Biological Activity of Factor X

In step a)-(i), the test composition which comprises Factor X is provided.

In step a)-(ii), a plurality of samples of the reference Factor X composition is provided, for example in the form of samples of successive dilutions of a basic reference composition. It is, for example, possible to use a first sample of the reference composition (100%), then successive dilutions to 50%, 25%, 12.5% and 6.2% of the reference composition. A plasma concentrate as described in the Hyphen Biomed references No. DP060K and DP060A can be used as reference composition.

In step a)-(iii), a Factor X-depleted plasma composition is provided, for example the composition sold by the company American Diagnostica Inc. (Stanford, USA).

For carrying out the method, those skilled in the art may refer to the test sold by the company Hyphen Biomed under the reference No. DP060K or the test sold by the company Hyphen Biomed under the reference No. DP060A.

For carrying out the method, those skilled in the art may refer to the following articles: Favre-Gilly et al. (1967, Cah Med Lyonnais, Vol. 43(28): 2611-2668) or Gjonaess et al. (Acta Obste Gynecol Scand, Vol. 54: 363-367).

Determination of the Biological Activity of Protein C and of Protein S

The same method is applied for the determination of the biological activity of protein C and of protein S.

Determination of the Biological Activity of a GLA-Domain Coagulation Protein by Measuring the Enzymatic Activity Using a Detectable Substrate, for Example a Chromogenic or Fluorogenic Substrate The basic principle of this second method is identical for all the GLA-domain coagulation factors. This second method consists in bringing the factor to be characterized into contact with a chromogenic or fluorogenic substrate peptide, which mimics the peptide sequence naturally recognized by said factor under consideration and which is lysed by said factor on its natural target protein(s).

The release of the chromophore or of the fluorophore is measured using a suitable spectrometer. This method may require the addition of a cofactor and, if necessary, the implementation of a step of activating the test factor. This second method makes it possible to measure the enzymatic functionalities of the GLA-domain coagulation protein tested with the cofactors. It is a less overall method than the method for measuring the coagulant activity previously described. However, this second method has the advantage of measuring the enzymatic activity of the GLA-domain coagulation protein of interest. Owing to a possibility of cross reaction(s) with other enzymes having trypsin-like activity, this second method is used mainly for measuring the biological activity of factors that are prepurified, concentrated or present in a matrix not containing other enzymes in significant amount, compared with the amount of the coagulation factor of interest.

In step a)-(iii) a protein C-depleted plasma composition is provided, for example the composition sold by the company American Diagnostica Inc. (Stanford, USA) under the No. 249.

In step a)-(iii) a protein C-depleted plasma composition is provided, for example the composition sold by the company American Diagnostica Inc. (Stanford, USA), under the No. 253.

Generally, the second method for determining the biological activity of a GLA-domain coagulation protein consists of a method which comprises the following steps:

a) providing
   (i) a test composition comprising a GLA-domain coagulation protein,
   (ii) a plurality of samples prepared from a reference composition comprising a known amount of said biologically active GLA-domain protein, each sample comprising a known amount of said biologically active GLA-domain protein, distinct from the amount of said protein contained in each of the other samples, and
   (iii) a detectable substrate of said GLA-domain protein, or a detectable substrate of a coagulation protein which is activated, directly or indirectly, by said GLA-domain protein, b) beginning the assay by carrying out the following steps b1) and b2):
   b1) bringing (i) the test composition comprising a GLA-domain coagulation protein into contact with (ii) a detectable substrate of said GLA-domain protein or with (iii) a detectable substrate of a coagulation protein which is activated, directly or indirectly, by said GLA-domain protein, in which case a composition comprising one or more coagulation protein(s) which is (are) activated, directly or indirectly, by said GLA-domain protein, and of which the coagulation protein that is the last to be activated consists of the coagulation protein capable of converting said detectable substrate, is also added,
   b2) bringing (i) each sample of the reference composition comprising a known amount of said biologically active GLA-domain protein into contact with (ii) a detectable substrate of said GLA-domain protein or with (iii) a detectable substrate of a coagulation protein which is activated, directly or indirectly, by said GLA-domain protein, in which case a composition comprising one or more coagulation protein(s) which is (are) activated, directly or indirectly, by said GLA-domain protein, and of which the coagulation protein that is the last to be activated consists of the coagulation protein capable of converting said detectable substrate, is also added, c) allowing the enzymatic conversion of said detectable substrate to take place for a predetermined time starting, respectively, from the beginning of step b1) and from the beginning of step b2), and then stopping the enzymatic reaction at the end of said predetermined time, d) measuring the amount of said detectable substrate which has been enzymatically converted:
   d1) for each sample of the reference composition, and
   d2) for the test composition, e) preparing a calibration curve, also called reference curve, with the measurements of the amount of said detectable substrate which has been enzymatically converted, determined in step d1), as a function of the known amount of said GLA-domain coagulation protein in each sample of the reference composition, f) determining the amount of said GLA-domain coagulation protein contained in the test composition, by determining, on the calibration curve prepared in step e), and on the basis of the amount of said detectable substrate which was enzymatically converted, determined in step d2), the deduced amount of said GLA-domain coagulation protein in the test composition.

The term "detectable" substrate is intended to mean a substrate which is converted, owing to the enzymatic reaction under consideration, into a converted product that is detectable. Generally, a chromogenic or fluorogenic substrate is used.

Determination of the Biological Activity of Factor II (Prothrombin)

For carrying out this method, those skilled in the art can use the colorimetric test sold by the company Hyphen Biomed under the reference No. 221605.

The standard curve can be prepared using the undiluted reference composition (200% prothrombin) and a series of diluted samples of the reference composition, for example samples diluted respectively to 160%, 100% and 10% prothrombin, and also a prothrombin-free sample.

For carrying out this method, those skilled in the art may refer to the following articles: Gomez et al. (2002, Clin Neurol Neurosurg, Vol. 104(4): 285-288), Delahousse et al. (2002, Blood Coagulation & Fibinolysis, Vol. 13(5): 465-470), Neville et al. (2001, Haemostasis, Vol. 31: 211-217), Lane et al. (1996, Thromb Haemost, Vol. 76(5): 651-662), Poort et al. (Blood, Vol. 88: 3698-3703), Rosen et al. (1999, ISTH, Abstract 269) or Stocker et al. (1996, Toxicon, Vol. 24(1): 81-89) or else to the documentation available at the following internet address: www.ncbi.nlm.nih.gov (OMIM, Coagulation Factor II, +176930).

Determination of the Biological Activity of Factor VII

For carrying out this method, those skilled in the art can use the colorimetric test sold by the company Hyphen Biomed under the reference No. 221304.

The standard curve can be prepared using the undiluted reference composition (200% prothrombin) and a series of diluted samples of the reference composition, for example samples diluted respectively to 100%, 10% and 1% Factor VII.

For carrying out this method, those skilled in the art may refer to the following articles: Seligsohn et al. (1978, Blood, Vol. 52(5): 978-988), Avvisati et al. (1980, Br J Haematol, Vol. 45(2): 343-352), Poller et al. (1981, Br J Haematol, Vol. 49(1): 69-75), Van Diejien et al. (1982, Haemostasis, Vol. 12(3): 241-255), Clarke et al. (1992, FEBS Lett, Vol. 298 (2-3): 206-210), Ledwozyw et al. (1993, Arch Vet Pol, Vol. 33(1-2): 123-127), Van Wersch et al. (1993, Int J Clin Lab Res, Vol. 23(4): 221-224), Devies et al. (1997, Vol. 76(5): 405-408), Topper et al. (1998, Am J Vet Res, Vol. 59(5): 538-541) or Chang et al. (1999, Biochemistry, Vol. 28(34): 10940-10948).

Determination of the Biological Activity of Factor IX

For carrying out this method, those skilled in the art can use the colorimetric test sold by the company Hyphen Biomed under the reference No. 221812.

The standard curve can be prepared using a series of diluted samples of the reference composition, for example samples comprising respectively a final Factor IXa concentration of 1.4, 3.4, 6.8 and 13.5 mU/ml of Factor IXa.

For carrying out this method, those skilled in the art may refer to the following articles: Taran et al. (1997, Biochemistry (Mosc.), Vol. 62(7): 685-693), Wagenwoord et al. (1990, Haemostasis, Vol. 20(5): 276-288) or the documentation available at the following internet address: "www.ncbi.nlm.nih.gov" (OMIM, Haemophilia B, FIX deficiency, +306900, +134540, +134510, +134520).

For carrying out this method, those skilled in the art can use the colorimetric test sold by the company Hyphen Biomed under the reference No. 221802. 221605.

The standard curve can be prepared using the undiluted reference composition (200% Factor IXa) and a series of diluted samples of the reference composition, for example samples diluted respectively to 100%, 50% and 20% Factor IXa.

For carrying out this method, those skilled in the art may refer to the following articles: Van Hylckama et al. (2000, Blood, Vol. 95(12): 3678-3682), Taran et al. (1997, Biochemistry (Mosc.), Vol. 62(7): 685-693), Wagenwoord et al. (1990, Haemostasis, Vol. 20(5): 276-288), Parekh et al. (1978, Br J Haematol, Vol. 40(4): 643-655), Orstavik et al. (1979, Br J Haematol, Vol. 42(2): 293-301) or the documentation available at the following internet address: "www.ncbi.nlm.nih.gov" (OMIM, Haemophilia B, FIX deficiency, +306900, +134540, +134510, +134520).

Determination of the Biological Activity of Factor X

For carrying out this method, those skilled in the art can use the test sold by American Diagnostica Inc., denoted Actichrom® FX, under the reference No. 880.

The standard curve can be prepared using the undiluted reference composition (100% Factor Xa) and a series of diluted samples of the reference composition, for example samples diluted respectively to 75%, 50%, 25%, 10% and 5% Factor IXa, and also a sample free of Factor X.

For carrying out this method, those skilled in the art may refer to the following articles: Kisiel et al. (1976, Biochemistry, Vol. 15: 4901-4906), Aurell et al. (1977, Thrombosis Research, Vol. 11: 595-605), Lindhout et al. (1978, Biochem Biophys Acta, Vol. 533: 327-341) or Bergstrom et al. (1978, Thrombosis Research, Vol. 12: 531-547).

Determination of the Biological Activity of Protein C

For carrying out this method, those skilled in the art can use the test sold by American Diagnostica Inc., denoted Actichrome Protein C, under the reference No. 836.

The standard curve can be prepared using the undiluted reference composition (100% protein C) and a series of diluted samples of the reference composition, for example samples diluted respectively to 75%, 50%, 25%, 10% and 5% protein C, and also a protein C-free sample.

For carrying out this method, those skilled in the art may refer to the following article: Francis et al. (1987, American journal of Clinical Pathology, Vol. 85(5): 619-625).

| Table of sequences | | |
|---|---|---|
| SEQ ID No. | Type | Designation |
| 1 | Nucleic acid | 5' region of the aptamer |
| 2 | | 3' region of the aptamer |
| 3 | | Mapt-1 core sequence |
| 4 | | Mapt-1 aptamer |
| 5 | | Aptamer not related to Mapt-1 |
| 6 to 34 | | Aptamers ("core sequences") |
| 35 | | Mapt-1.2.-CS aptamer |
| 36 | | Mapt-1.2.-CSO aptamer |
| 37 | | Mapt-2-CS aptamer |
| 38 | | Mapt-2.2.-CS aptamer |
| 39 | | Mapt-2 aptamer |

The present invention is also illustrated by the following examples.

EXAMPLES

Example 1: Preparation of an Affinity Support

The affinity support was made from a solid support material consisting of a matrix onto which streptavidin (streptavidin-agarose—Novagen®) was grafted.

A volume of 1 ml of gel was introduced into a container consisting of a column (i.d. 11 mm). The gel was washed with purified water in order to remove the storage solvent. The Gel Characteristics are:

Biotin adsorption capacity: ≥85 nanomol/ml of gel

Functional test: Capture>99% of biotinylated thrombin in 30 minutes at AT

Other tests: Protease-free, endo/exonuclease-free, RNase-free

Preservative: 100 mM sodium phosphate, pH 7.5, +NaN$_3$ 0.02.

The output of the packed column (gel bed height=1 cm) is connected to a detector of UV absorbance at 254 nm and a recording device.

The biotinylated anti-GLA nucleic aptamers of sequence SEQ ID No. 4, also called "Mapt-1" aptamers in the present description, are solubilized in purified water at a final concentration of 0.5 mg/0.187 ml, i.e. a final molar concentration of 0.1 mM. The solution of nucleic aptamers was activated at 95° C. according to the standard cycle, for immobilizing the aptamers on the solid support material.

The solution of nucleic aptamers was previously diluted with 4.8 ml of purified water then 1.5 ml of concentrated buffer so as to obtain the following formulation: 50 mM Tris, 50 mM NaCl, 4 mM MgCl$_2$, 10 mM CaCl$_2$, pH 7.5.

The absorbance detector is adjusted to 1 AUFS (Absorbance Unit Full Scale) and the OD at 254 nm of this solution is recorded at 0.575 $AU_{254}$.

The solution of biotinylated nucleic aptamers is injected onto the prepacked streptavidin-agarose gel and recirculated with a peristaltic pump at a flow rate of 2.5 ml/minute, i.e. a contact time on the gel of 24 seconds (input/output I/O). Under these conditions, the OD at 254 nm stabilizes rapidly at 0.05 $AU_{254}$, which is 91% of the theoretical coupling, i.e. 0.455 mg of nucleic aptamers per milliliter of gel.

Washing with a 2M NaCl buffer is carried out, in order to remove the nucleic aptamers that were not bound specifically to the streptavidin molecules grafted onto the solid support material.

Example 2: Purification of a Recombinant GLA-Domain Protein (Transgenic Human Factor IX)

An affinity support of the type described in example 1 was used to purify recombinant human factor IX produced in the milk of pigs transgenic for human Factor IX.

A. Protocol for Purifying by Affinity Chromatography

The characteristics for implementing the step of affinity chromatography of the starting sample on an affinity support on which the Mapt-1 anti-GLA aptamers are immobilized are described in the tables below.

Step 1: Clarification

Clarification with citrate to obtain clarified milk at pH 7.5 at a final concentration of 0.25M of citrate buffer.

Step 2: MEP Hypercel

SM: clarified milk (IBF 25-10 ml of gel)

FIX loading: 243 IU/ml of gel
Equilibration buffer: 0.25M citrate, pH 7.5
Elution buffer: water Step 3: Dialysis SM: MEP eluate
Dialysis buffer: 50 mM Tris-50 mM NaCl, pH 7.5

Step 4: MAPT-1 (3 run)

SM: Dialyzed MEP eluate (IBF 1.1-1 ml of gel)
FIX loading: 230 IU/ml of gel
Equilibration buffer: 50 mM Tris-50 mM NaCl-4 mM $MgCl_2$-10 mM $CaCl_2$, pH 7.5
Elution buffer: 20 mM Tris-10 mM EDTA, pH 7.5
Regeneration buffer: 20 mM Tris-1M NaCl-5% PG, pH 7.5

B. Characteristic of the Raw Material (RM)

The raw material used consists of untreated milk from a pig transgenic for human Factor IX.

C. Monitoring of the Process

C.1. Step 1: Clarification

C.1.1.—Monitoring of Clarification

Thawing of E0 at 37° C.

Mixture with a very milky appearance: 45 g (⅔) pig's milk+25 g (⅓) citrate buffer concentrated to 0.75M Gentle stirring for 30 min at ambient temperature Centrifugation for 30 min, 15° C., 5000 g Pellet: small and white containing pig hairs and impurities Supernatant: two phases, the upper solid phase creamy and white constituting the fatty substances and the yellowish phase representing the clarified milk (E1

Clarified milk recovered with pump

Deep filtration of the clarified milk with a Cuno BioCap 25 Filter

Deep freezing at −80° C. of the clarified filtered milk (E2).

C.1.2—Results in Total Proteins, in FIX:C, FIX:Ag and FIX:am

The results are shown in tables 1 and 2 below.

TABLE 1

| | | | Coagulation | | | Total proteins | | | | | |
| | | | | Q | R | | Q | R | Purification | | |
| Step | Code | Weight (g) | [FIX:C] (IU/ml) | FIX:C (IU) | FIX:C (%) | [Prot] (g/l) | Prot. (g) | Prot. (%) | AS (IU/mg) | Purity | Increased purity |
|---|---|---|---|---|---|---|---|---|---|---|---|
| Untreated milk | E0 | 45.0 | 57.2 | 2574 | 100.0 | 103.2 | 644 | 100.0 | 0.6 | 0.2 | / |
| Clarified milk before filtration | E1 | 65.3 | 36.0 | 2350 | 91.3 | 37.5 | 2451 | 52.8 | 1.0 | 0.4 | 1.7 |
| Clarified milk | E2 | 63.8 | 38.2 | 2438 | 94.7 | 34.7 | 2214 | 47.7 | 1.1 | 0.5 | 2.0 |

TABLE 2

| | | Amidolytic | | | Antigenic | | | |
| | | | Q | R | | Q | R | Ratio | |
| | Code | [FIX:Am] (IU/ml) | FIX:Am (IU) | FIX:Am (%) | [FIX:Ag] (IU/ml) | FIX:Ag (IU) | FIX:Ag (%) | [C]/[Ag] | [Am]/[Ag] |
|---|---|---|---|---|---|---|---|---|---|
| | E0 | 40 | 1798 | 100 | 147 | 6615.0 | 100.0 | 0.4 | 0.3 |
| | E1 | 23 | 1510 | 84 | 1147 | 443.1 | 112.5 | 0.3 | 0.2 |
| | E2 | 22 | 1426 | 79 | 95 | 6062.0 | 91.6 | 0.4 | 0.2 |

C.2. Step 2: MEP Hypercel
C.2.1.—Characteristics of the Chromatography Support
  Column: IBF 25, 2.5 cm high
  Gel: MEP 10 ml of gel, batch 200920/G206-04
  No. of use: $2^{nd}$ use
  Regeneration of the gel before use: 1 CV 1M NaOH; 2 CV 2M NaCl; 4 CV water
C.3.2—Preparation of the Starting Material (SM)
  Thawing of E2 at 37° C.
  Reference: 1 IU of FIX=4 µg/ml
  Injected volume (g): 63.81
  FIX loading in IU per ml of gel (IU/ml gel): 243 IU/ml of gel
  FIX loading in µg per ml of gel (µg/ml gel): 972 µg/ml of gel
C.2.3—Characteristics of Chromatography Buffers
  Equilibration buffer: 0.25M citrate, pH 7.5, 612 mOsmol/kg, 31.9 mS/cm
  MEP elution buffer: water
C.2.4—Monitoring of Chromatography Steps C.3. Step 3: Dialysis
Dialysis of E4 (50 g) in 2 baths of 1 L, all night with stirring at 4° C.,

TABLE 6

| Samples | Fractions | Weight g | pH | Osmolarity mosmol/kg | Conductivity mS/cm |
|---|---|---|---|---|---|
| E4 | before dialysis | 49.18 | 7.81 | 121 | 7.11 |
| E5 | after dialysis | 51.08 | 7.81 | 149 | 7.18 |
|  | Dialysis buffer 50 mM Tris - 50 mM NaCl |  | 7.50 | 157 | 7.52 |

C.4.: Chromatography on Affinity Support with Anti-GLA Aptamers (Mapt-1)

Three independent purification tests for transgenic human Factor IX pre-purified as described above were carried out. The operating conditions and the results of each test are specified below.

TABLE 3

| Code | Step | Flow rate ml/min | Weight g | Peak AU | pH | Osmolarity mosmol/kg | Conductiv. mS/cm | Observations |
|---|---|---|---|---|---|---|---|---|
| E2 | SM | 0.85 | 63.81 | NA | 7.43 | 231 | 31.9 | NA |
| E3 | NR | 0.85 | 139.61 | 2 | 7.45 | 719 | 32 | Saturation |
| E4 | E MEP | 1 | 51.68 | 2 | 7.81 | 121 | 7.11 | Saturation |

Regeneration of the gel before use: 10 CV 1M NaOH; 4 CV 2M NaCl; 10 CV water; 10 CV 20% ethanol.

C.2.5. Results in Total Proteins

Column: IBF 1.1, 0.9 cm high
Gel: MAPT-1, 1 ml of gel
No. of use: $2^{nd}$ use

TABLE 4

|  |  |  | Coagulation | | | Total proteins | | | Purification | | |
|---|---|---|---|---|---|---|---|---|---|---|---|
|  |  |  |  | Q | R |  | Q | R |  |  |  |
| Steps | Code | Weight (g) | [FIX:C] (IU/ml) | FIX:C (IU) | FIX:C (%) | [Prot] (g/l) | Prot. (g) | Prot. (%) | AS (IU/mg) | Purity | Increased purity |
| Clarified milk | E2 | 63.8 | 38.2 | 2438 | 100.0 | 34.7 | 2214.2 | 100.0 | 1.1 | 0.5 | / |
| Nonadsorbed | E3 | 139.6 | 3.1 | 433 | 17.8 | 8.4 | 1175.4 | 53.1 | 0.4 | 0.2 | 0.3 |
| Elution MEP | E4 | 51.7 | 20.3 | 1049 | 43.0 | 3.6 | 186.6 | 8.4 | 5.6 | 2.5 | 5.1 |
| MEP eluate dialyzed | E5 | 51.1 | 14.5 | 741 | 30.4 | 3.3 | 169.1 | 7.6 | 4.4 | 1.9 | 4.0 |

TABLE 5

|  | Amidolytic | | | Antigenic | | | Ratio | |
|---|---|---|---|---|---|---|---|---|
|  |  | Q | R |  | Q | R |  |  |
| Code | [FIX:Am] (IU/ml) | FIX:Am (IU) | FIX:Am (%) | [FIX:Ag] (IU/ml) | FIX:Ag (IU) | FIX:Ag (%) | [C]/[Ag] | [Am]/[Ag] |
| E2 | 22 | 1426 | 100 | 95 | 6062.0 | 100.0 | 0.4 | 0.2 |
| E3 | 1 | 148 | 10 | ND | ND | ND | ND | ND |
| E4 | 9 | 484 | 34 | 47 | 2429.0 | 40.1 | 0.4 | 0.2 |
| E5 | 9 | 455 | 32 | 45 | 2298.6 | 37.9 | 0.3 | 0.2 |

C.4.2—Preparation of the Starting Material (SM)
Adjustment of pH and addition of 4 mM $MgCl_2$ and 10 mM $CaCl_2$ final concentration, to E5
Aliquoting of E5 (48.17 g), aliquoted as 3×16 g, two of which are stored at −80° C. for the following tests
Reference: 1 IU of FIX=4 μg/ml
Injected volume (g): 16.14
FIX loading in IU per ml of gel (IU/ml gel): 234 IU/ml of gel
FIX loading in μg per ml of gel (μg/ml gel): 936 μg/ml of gel C.4.3. Characteristics of Chromatography Buffers
Equilibration buffer: 50 mM Tris, 50 mM NaCl, 10 mM $CaCl_2$, 4 mM $MgCl_2$, pH 7.51, 218 mOsmol/kg, 10.77 mS/cm
Elution buffer 1: 20 mM Tris, 10 mM EDTA, pH 7.53, 56 mOsmol/kg, 2.64 mS/cm
Elution buffer 2 (regeneration buffer): 20 mM Tris, 1M NaCl, 50% propylene glycol, pH 7.52, 18.27 mS/cm.

C.4.4. Monitoring of Chromatography Steps

Test 1
Column equilibrated at pH 7.34 and 211 mOsm/kg
FIX loading: 234 IU/ml of gel.

TABLE 7

| Samples | Fractions | Flow rate ml/min | Weight g | Peak AU | pH | Osmolarity mosmol/kg | Conductiv. mS/cm | Observations |
|---|---|---|---|---|---|---|---|---|
| E5 | SM | 0.6 | 16.14 | na | 7.51 | 181 | 8.18 | na |
| E6 | NR | 0.6 | 29.56 | 0.5 | 7.44 | 193 | 9.03 | saturation |
| E7 | E1 MAPT-1 | 0.6 | 6.68 | 0.02 | 6.40 | 99 | na | decrease in pH |
| E8 | E2 MAPT-1 | 0.6 | 6.66 | 0.1 | 7.41 | na | na | na |

Test 2
Column equilibrated at pH 7.39 and 220 mOsm/kg, use of the gel
FIX loading: 236 IU/ml of gel.

TABLE 8

| Fractions 315 256 | Flow rate ml/min | Weight g | Peak AU | pH | Osmolarity mosmol/kg | Observations |
|---|---|---|---|---|---|---|
| SM | 0.1 | 13.50 | na | 7.42 | 179 | Na |
| NR | 0.1 | 20.29 | 0.5 | 7.36 | 197 | saturation |
| E1 MAPT-1 | 0.1 | 2.84 | 0.02 | 7.06 | 187 | decrease in pH |
| E2 MAPT-1 | 0.1 | 3.77 | 0.1 | 6.39 | na | decrease in pH |

Test 3
Column equilibrated at pH 7.45 and 219 mOsm/kg, 5± use of the gel
FIX loading: 210 IU/ml of gel.

TABLE 9

| Fractions 315 258 | Flow rate ml/min | Weight g | Peak AU | pH | Osmolarity mosmol/kg | Observations |
|---|---|---|---|---|---|---|
| SM | 0.6 | 12.71 | na | 7.47 | 180 | na |
| NR | 0.6 | 23.79 | 0.5 | 7.46 | 206 | saturation |
| E1 MAPT-1 | 0.6 | 2.67 | 0.02 | 6.94 | 168 | decrease in pH |
| E2 MAPT-1 | 0.6 | 4.20 | 0.1 | 7.36 | na | na |

C.4.5. Results in Total Proteins, in FIX:C, FIX:Ag and FIX:Am,

The assays of total proteins were carried out by the Tebu Bio laboratory. FIX:C levels were determined by LBA and FIX:Ag and FIX:Am levels by LIB.

C.4.5.1 Affinity Chromatography Results, Test 1

TABLE 10

| Step | Code | Weight (g) | [FIX:C] (IU/ml) | Q FIX:C | Coag R FIX:C (%) | [Total prot.] | Protein Q Total prot. | R Total prot. (%) | Purification AS (IU/mg) | Purity | Increased purity |
|---|---|---|---|---|---|---|---|---|---|---|---|
| Injection | E5 | 16.1 | 14.5 | 234 | 100.0 | 3.310 | 53.4 | 100.0 | 4.4 | 1.9 | / |
| Nonadsorbed | E6 | 29.6 | 8.9 | 263 | 112.4 | 1.360 | 40.2 | 75.3 | 6.5 | 2.9 | 1.5 |
| Elution 1 | E7 | 6.7 | 0.50 | 3.3 | 1.4 | 0.015 | 0.1 | 0.2 | 33.3 | 14.7 | 7.6 |

TABLE 11

| Code | [FIX:Am] (IU/ml) | Am Q FIX:Am (IU) | R FIX:Am (%) | [FIX:Ag] (IU/ml) | Ag Q FIX:Ag (IU) | R FIX:Ag (%) | Ratio [C]/[Ag] | [Am]/[Ag] |
|---|---|---|---|---|---|---|---|---|
| E5 | 9 | 143.6 | 100.0 | 45 | 726.3 | 100.0 | 0.3 | 0.2 |
| E6 | 2.7 | 78.6 | 54.7 | 26 | 768.6 | 105.8 | 0.3 | 0.1 |
| E7 | 0.2 | 1.1 | 0.7 | 0.238 | 1.6 | 0.2 | 2.1 | 0.7 |

C.4.5.2. Affinity Chromatography Results, Test 2

TABLE 12

| Step | Code | Weight (g) | [FIX:C] (IU/ml) | Q FIX:C | Coag R FIX:C (%) | [Total prot.] | Protein Q Total prot. | R Total prot. (%) | Purification AS (IU/mg) | Purity | Increased purity |
|---|---|---|---|---|---|---|---|---|---|---|---|
| Injection | SM | 13.5 | 17.5 | 236 | 100.0 | 3.110 | 42.0 | 100.0 | 5.6 | 2.5 | / |
| Nonadsorbed | NR | 20.3 | 8.7 | 177 | 74.7 | 1.940 | 39.4 | 93.8 | 4.5 | 2.0 | 0.8 |
| Elution 1 | E1 | 2.8 | 0.32 | 0.91 | 0.4 | 0.007 | 0.0 | 0.0 | 45.7 | 20.1 | 8.1 |

TABLE 13

| Code | [FIX:Am] (IU/ml) | Am Q FIX:Am (IU) | R FIX:Am (%) | [FIX:Ag] (IU/ml) | Ag Q FIX:Ag (IU) | R FIX:Ag (%) | Ratio [C]/[Ag] | [Am]/[Ag] |
|---|---|---|---|---|---|---|---|---|
| SM | 9.4 | 127.4 | 100.0 | 45.0 | 607.5 | 100.0 | 0.4 | 0.2 |
| NR | 5 | 100.4 | 78.8 | 25.0 | 507.3 | 83.5 | 0.3 | 0.2 |
| E1 | 0.1 | 0.4 | 0.3 | 0.2 | 0.6 | 0.1 | 1.6 | 0.7 |

C.4.5.3. Affinity Chromatography Results, Test 3

TABLE 14

| Step | Code | Weight (g) | Protein Coag [FIX:C] (IU/ml) | Q FIX:C | R FIX:C (%) | [Total prot.] | Total prot. | R Total prot. (%) | Purification AS (IU/mg) | Purity | Increased purity |
|---|---|---|---|---|---|---|---|---|---|---|---|
| Injection | SM | 12.7 | 16.5 | 210 | 100.0 | 4.430 | 56.3 | 100.0 | 3.7 | 1.6 | / |
| Nonadsorbed | NR | 23.8 | 8.0 | 190 | 90.8 | 2.130 | 50.7 | 90.0 | 3.8 | 1.7 | 1.0 |
| Elution 1 | E1 | 2.7 | 1.8 | 4.8 | 2.3 | 0.011 | 0.0 | 0.1 | 163.6 | 72.1 | 43.9 |

TABLE 15

| | Am | | | Ag | | | | Ratio | |
|---|---|---|---|---|---|---|---|---|---|
| Code | [FIX:Am] (IU/ml) | Q FIX:Am (IU) | R FIX:Am (%) | [FIX:Ag] (IU/ml) | Q FIX:Ag (IU) | R FIX:Ag (%) | [C]/[Ag] | [Am]/[Ag] | [C]/[Am] |
| SM | 9.4 | 119.1 | 100.0 | 47 | 597.4 | 100.0 | 0.4 | 0.2 | 1.8 |
| NR | 4.4 | 105.6 | 88.7 | 23 | 547.2 | 91.6 | 0.3 | 0.2 | 1.8 |
| E1 | 0.5 | 1.4 | 1.2 | 0.80 | 2.1 | 0.4 | 2.3 | 0.7 | 3.3 |
| E2 | 22 | 1426 | 79 | 95 | 6062.0 | 91.6 | 0.4 | 0.2 | 1.7 |

Example 3: Purification of a GLA-Domain Protein with a Correctly Gamma-Carboxylated GLA Domain In example 3, tests were carried out in particular for purifying a GLA protein with a correctly gamma-carboxylated GLA domain, from a starting sample comprising a mixture of different forms of the same GLA-domain protein, respectively forms in which the GLA domain is correctly gamma-carboxylated and forms in which the GLA domain is incorrectly gamma-carboxylated.

More specifically, tests were carried out for purifying recombinant Factor IX produced in the milk of pigs transgenic for human Factor IX. The milk of the transgenic pigs comprises a mixture of (i) active transgenic recombinant human Factor IX with a correctly gamma-carboxylated GLA domain and (ii) inactive transgenic recombinant human Factor IX with an incorrectly gamma-carboxylated GLA domain.

The results of these tests are given below.

4.1. Selective Binding of Mapt-1 to GLA Proteins with a Correctly Gamma-Carboxylated GLA Domain 4.1.1. Experimental Conditions a) Binding Measurement: Biacore T100 Apparatus Chip: the biotinylated Mapt-1 aptamer was immobilized on a streptavidin surface (chip SA, GE) at 4326 RU on the active flow cell No. 3 (FC3). A control nucleic aptamer is immobilized at 4069 RU on the flow cell No. 1 (FC1). The injected sample runs over FC3 and FC1 in order to completely extract the background noise due to nonspecific interactions.

Run buffer and dilution buffer for samples: 50 mM Tris/50 mM NaCl/10 mM $CaCl_2$/4 mM $MgCl_2$/pH=7.4.

Flow rate: 30 μl/min, injection for 60 s, dissociation for 120 s

Signal: Fc3 signal corrected for the flow cell No. 1 signal

Regeneration: 10 mM EDTA in water for injection.

More specifically, a first solid support (FC3) was produced, on which molecules of the nucleic aptamer of the invention having the sequence SEQ ID No. 4, also known here as "Mapt-1", were immobilized. Before being bound to the solid support, the 5' end of the Mapt-1 aptamer was chemically coupled to a spacer chain consisting of one molecule of PEG (C18). Then, the free end of the spacer chain, opposite to the end coupled to the aptamer, was coupled to a biotin molecule.

A second solid support (FC1) was also produced, on which molecules of an aptamer not related to Mapt-1, having the sequence SEQ ID No. 5, which does not bind to GLA-domain proteins, were immobilized.

A solid support containing immobilized molecules of streptavidin is available (series S sensor chip SA, GE).

Then, the above solid support was brought into contact with the above aptamer compounds in order to immobilize the nucleic acids having the sequences SEQ ID No. 4 and SEQ ID No. 5, by noncovalent association between the streptavidin molecules of the support and the biotin molecules of the aptamer compounds.

The Mapt-1 aptamer is thus immobilized with an immobilization rate of 4326 RU (1 RU corresponds approximately to 1 pg of product immobilized per $mm^2$).

Transgenic recombinant human FIX produced in pigs and prepurified by chromatography on an MEP HyperCel® support was diluted in run buffer (50 mM Tris, 50 mM NaCl, 10 mM $CaCl_2$, 4 mM $MgCl_2$, pH 7.4).

The sample was injected sequentially onto (i) the FC1 chip containing the non-related aptamer immobilized by a biotin-streptavidin interaction and (ii) the FC3 chip (solid support) containing the Mapt-1 aptamer immobilized by a biotin-streptavidin interaction. Controls are obtained by injecting blanks containing only run buffer. All the injections were carried out with a flow rate of 30 μl/min for 60 sec. After the injection, run buffer was injected onto the chip at an identical flow rate for 120 sec. Elution buffer (10 mM EDTA in water for injection) was then injected for 30 sec with a flow rate of 30 μl/min in order to uncouple the substances bound to the aptamer. The chip makes it possible to study in real time the formation and the breaking of interactions between FIXtg and the immobilized aptamer through surface plasmon resonance (SPR). Binding to the immobilized aptamer generates an increase in the signal expressed in resonance units (RU) recorded by the apparatus (FIG. 3). These analyses are carried out with the Biacore T100 SPR apparatus (GE). The modeling of the recorded interactions is carried out by means of the Biaevaluation software (GE).

The signal obtained with the FC1 chip is subtracted from the signal obtained with the FC3 chip in order to eliminate the background noise due to nonspecific interactions.

b) Measurement of Specific Activity: Ratio of Amidolytic Activity Over Antigen Level Amidolytic activity is measured using the Biophen FIX kit according to the supplier's instructions.

The antigen level is measured using the Stago Asserachrom® VII:Ag kit according to the supplier's instructions.

c) Samples:

Benefix® recombinant FIX (Nonacog alpha, Wyeth) with 12 γ-carboxylations according to the manufacturer's data.

FIX-TG purified from transgenic pig's milk (milk K97, supplied by GTC) by various chromatography steps (assay 315138) in order to obtain more than 95% purity. The γ-carboxylation of the light chain was analyzed by LC-MS after activation and digestion with PNGase F. The MS spectra showed different degrees of γ-carboxylation on the light chain ranging from 1 to 7. The normal level of γ-carboxylation is 12.

4.1.2. Results

Figure 1:
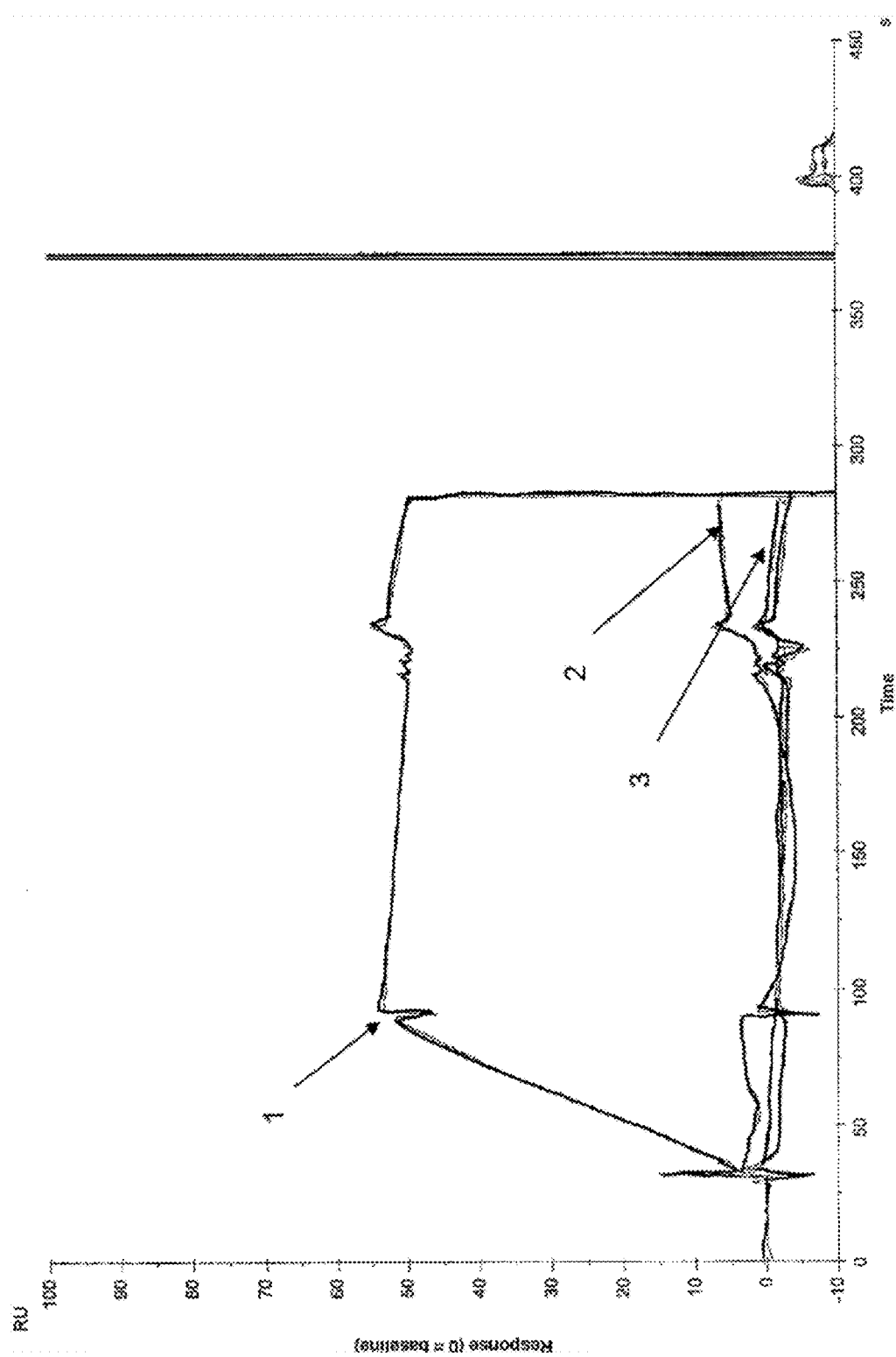
FIG. 1 shows the curves of binding (i) of the Factor IX present in various compositions to (ii) an aptamer specific for GLA-domain proteins which is immobilized on a support, in an assay according to the surface plasmon resonance technique. Along the x-axis: the time, expressed in seconds; along the y-axis, the resonance signal, expressed in arbitrary resonance units. Curve No. 1: recombinant FIX sold under the name BeneFIX® by the company Wyeth; curve No. 2: semi-purified preparation of recombinant Factor IX produced by transgenic pigs (FIXtg). This FIX is poorly gamma-carboxylated (carboxylation measurement <7 gamma carboxylations out of the 12 present); curve No. 3: negative control (buffer alone).

The results are shown in FIG. 1.

The biacore binding measurements show that the Mapt-1 aptamer does not bind to the purified FIX-Tg sample characterized by an incomplete degree of γ-carboxylation and a specific activity of 0.2. These results suggest a selectivity of Mapt-1 for the correctly γ-carboxylated forms.

4.2. Capacity of an Affinity Support According to the Invention to Selectively Retain Human Factor IX of which the GLA Domain is Correctly Gamma-Carboxylated Milk from a pig transgenic for human Factor IX was subjected to a method similar to that described in example 2, comprising the following steps:

a) clarifying with citrate, b) running the clarified milk on an MEP Hypercel® chromatography support, c) eluting the retained fraction and dialyzing the eluate against a 50 mM Tris, 50 mM NaCl buffer, at pH 7.5, then adjusting with 10 mM CaCl$_2$ and 4 mM MgCl$_2$, d) running the eluate obtained at the end of step c) on an affinity support on which anti-GLA aptamers are immobilized, in this case the Mapt-1 aptamer.

Separately, as a control test, plasma factor IX was run on an affinity support on which anti-GLA aptamers are immobilized, in this case the Mapt-1 aptamer.

4.2.1. Experimental Conditions 4.2.1.1. Chromatography Conditions a) Step 1: Clarification Clarification with citrate to obtain clarified milk at pH 7.5 at a final citrate buffer concentration of 0.25M b) Step 2: Running on MEP Hypercel®
SM: clarified milk (IBF 25-10 ml of gel)
FIX loading: 243 IU/ml of gel
Equilibration buffer: 0.25M citrate, pH 7.5
Elution buffer: water.

c) Step 3: Dialysis
SM: MEP eluate
Dialysis buffer: 50 mM Tris-50 mM NaCl, pH 7.5.

d) Step 4: MAPT-1 (3 runs)
SM: Dialysed MEP eluate (IBF 1.1-1 ml of gel) adjusted for MgCl$_2$ and CaCl$_2$ so as to obtain the respective concentrations: 10 mM and 4 mM
FIX loading: 230 IU/ml of gel
Equilibration buffer: 50 mM Tris-50 mM NaCl-4 mM MgCl$_2$-10 mM CaCl$_2$, pH 7.5
Elution buffer: 20 mM Tris-10 mM EDTA, pH 7.5
Regeneration buffer: 20 mM Tris-1M NaCl-5% PG, pH 7.5.

4.2.1.2. Measurement of Specific Activity: Ratio of Amidolytic Activity Over Antigen Level or of Coagulant Activity Over Antigen Level Amidolytic activity is measured using the Biophen FIX kit according to the supplier's recommendations.

Coagulant activity is measured by a chronometric method that consists in measuring the coagulation time in the presence of cephalin and kaolin, of a system in which all the factors are present in excess except for Factor IX (Factor IX deficient plasma, Stago). The FIX is provided by the dilution of the standard or of the sample. The analyses are done on an auto-analyzer: type BCT and the data is processed by "hemostasis" software for calculating the activity and the confidence interval.

Antigen level is measured using the Stago Asserachrom® VII:Ag kit according to the supplier's instructions.

4.2.1.3. Binding Measurement: Biacore T100 Apparatus

Chip: Mapt-1 immobilized on a streptavidin surface (chip SA, GE) at 5073 RU on the active flow cell No. 2 (FC2). A non-relevant aptamer is immobilized at 4959 RU on the flow cell No. 1. The injected sample runs over FC2 and FC1 in order to completely subtract the background noise due to nonspecific interactions.

Buffer for running and dilution of samples: 50 mM Tris/10 mM CaCl$_2$/pH=7.4

Flow rate: 30 μl/min injection for 100 s, dissociation for 200 s

Signal: FC2 signal corrected for the flow cell No. 1 signal
Regeneration: 10 mM EDTA in PBS buffer, pH 7.4.

4.2.2. Results 4.2.2.1. Chromatography

Figure 2:
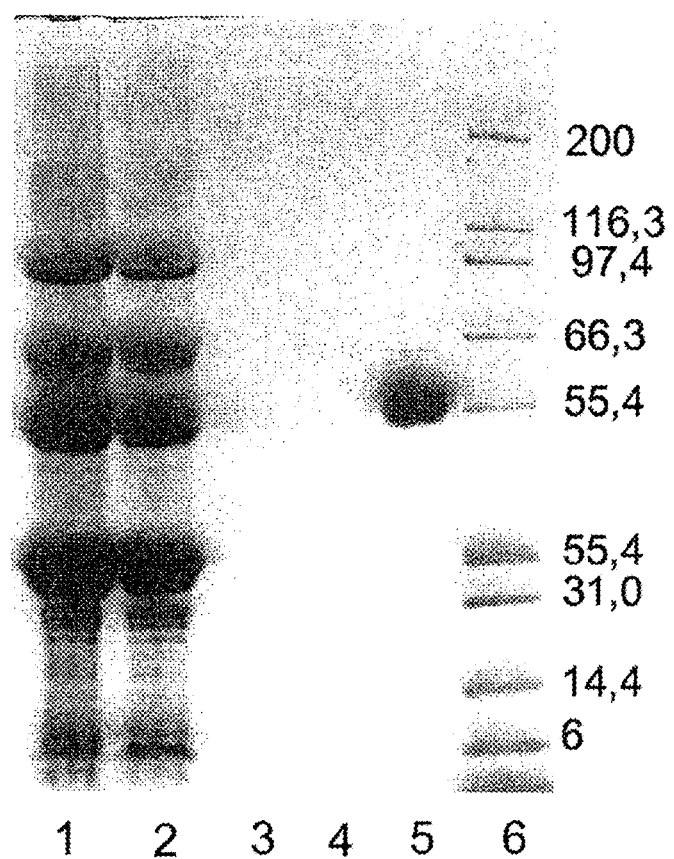
FIG. 2 is the image of an SDS-PAGE electrophoresis gel of proteins contained in a purified fraction of human plasma Factor IX or milk from a pig transgenic for Factor IX, having undergone a pretreatment by clarification then chromatography on an MEP HyperCel® support, then chromatography on an affinity support on which nucleic aptamers specific for GLA-domain proteins are grafted. The SDS-PAGE gel was treated with Coomassie blue. From left to right: lane 1: starting composition: milk from a pig transgenic for human Factor IX, having undergone a pretreatment by clarification then chromatography on an MEP HyperCel® support; lane 2: proteins contained in the fraction not retained on the affinity support; lane 3: proteins contained in the elution fraction; lane 4: proteins contained, in the output from the affinity support, in the regeneration buffer; lane 5: purified fraction of human plasma Factor IX; lane 6: reference proteins of known molecular weight. The apparent molecular weights of certain protein bands of the reference proteins are indicated.

A chromatogram was produced and also an SDS-PAGE gel electrophoresis was carried out with Coomassie blue staining. The results are shown in FIG. 2.

The analysis of the chromatogram of the Mapt-1 step shows first that the vast majority of the injected sample is not retained and, second, a very weak elution peak that may correspond to minority species of FIX-TG.

As shown in the image of FIG. 3, the SDS-PAGE gel analysis of the eluates does not enable the visualization of possibly purified FIX, which is coherent with the quantity related to the observed peak height.

Figures 3A, 3B:
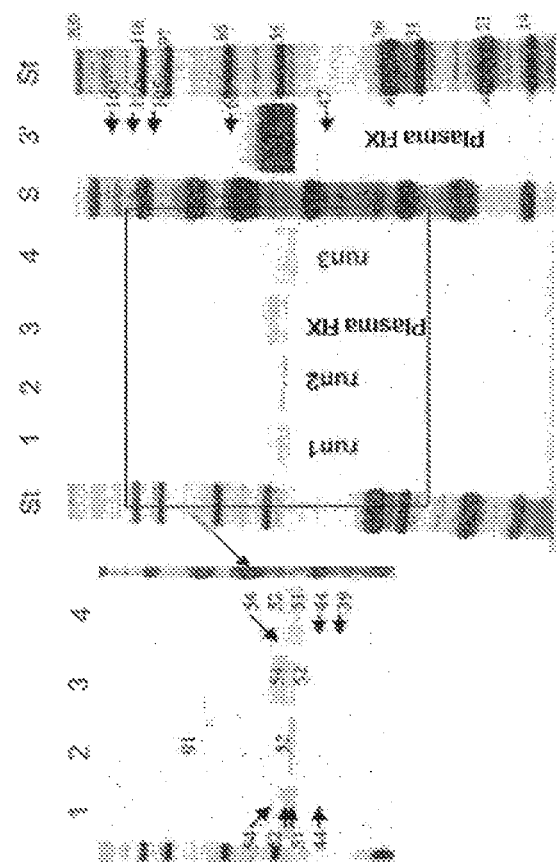
FIGS. 3A-3B are the images of an SDS-PAGE electrophoresis gel of proteins contained in a purified fraction of human plasma Factor IX or in milk from a pig transgenic for human Factor IX, having undergone a pretreatment by clarification then chromatography on an MEP HyperCel® support, then purification on an affinity support on which nucleic aptamers specific for GLA-domain proteins are grafted. The SDS-PAGE gel was treated with silver nitrate.

On the other hand, when an SDS-PAGE electrophoresis gel is prepared and then stained with silver nitrate, protein bands of purified transgenic recombinant human FIX, which has been shown to possess a very high biological activity, are clearly visualized in the eluate of the fraction retained on the Mapt-1 affinity support (see the SDS-PAGE gel image shown in FIGS. 3A and 3B).

4.2.2.2. Specific Activity of Factor IX Found in the Various Fractions

Table 19 below presents the results of biological activity of Factor IX in the starting product and in the various fractions obtained during the affinity chromatography on the Mapt-1 affinity support.

TABLE 16

| Sample | Test 1 Test No. 09315255 | | Test 2 Test No. 09315256 | | Test 3 Test No. 09315258 | | Plasma controls Test No. 09315257 | |
|---|---|---|---|---|---|---|---|---|
| Analysis | [C]/[Ag] | [Am]/[Ag] | [C]/[Ag] | [Am]/[Ag] | [C]/[Ag] | [Am]/[Ag] | [C]/[Ag] | [Am]/[Ag] |
| Start | 0.3 | 0.2 | 0.4 | 0.2 | 0.4 | 0.2 | 1.1 | 1.3 |
| Nonabsorbed | 0.3 | 0.1 | 0.3 | 0.2 | 0.3 | 0.2 | 1.0 | 0.7 |
| Mapt eluate | 2.1 | 0.7 | 1.6 | 0.7 | 2.1 | 0.7 | 1.2 | 1.7 |

4.2.2.3 Binding Test on Biacore® for Various Forms of Human Factor IX

Figure 4:
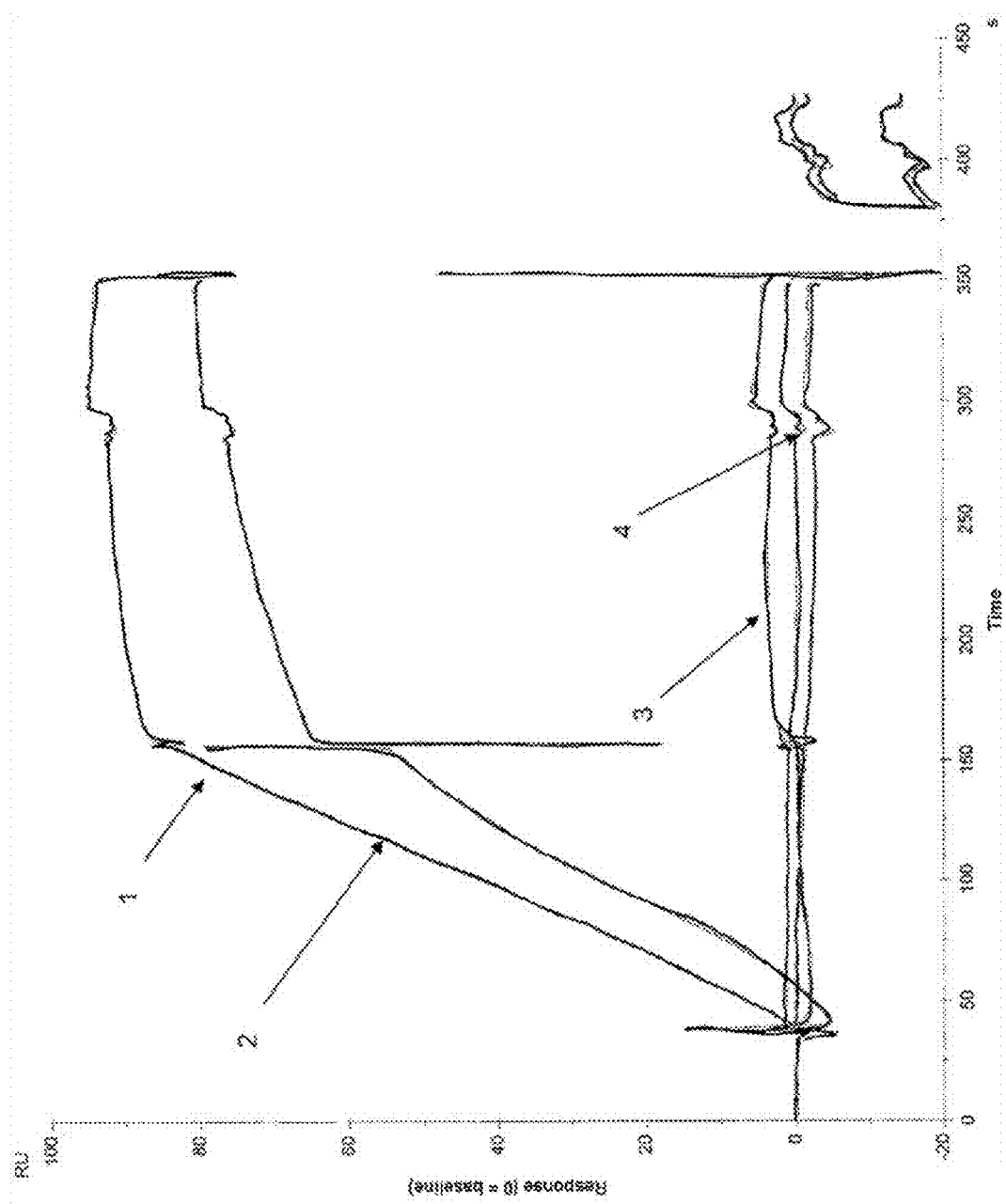
FIG. 4 shows the curves of binding (i) the Factor IX present in various compositions to (ii) an aptamer specific for GLA-domain proteins which is immobilized on a support, in an assay according to the surface plasmon resonance technique. Along the x-axis: the time, expressed in seconds; along the y-axis, the resonance signal, expressed in arbitrary resonance units. Curve No. 1: preparation of human plasma Factor IX; curve No. 2: preparation of recombinant Factor IX produced by a transgenic pig, purified by chromatography on an MEP HyperCel® support then on an affinity support comprising anti-GLA aptamers; curve No. 3: preparation of recombinant Factor IX produced by a transgenic pig, before running over an affinity support comprising anti-GLA aptamers (after MEP HyperCel®); curve No. 4: negative control preparation (buffer alone).

The results are shown on the graph in FIG. 4.

Figure 5:
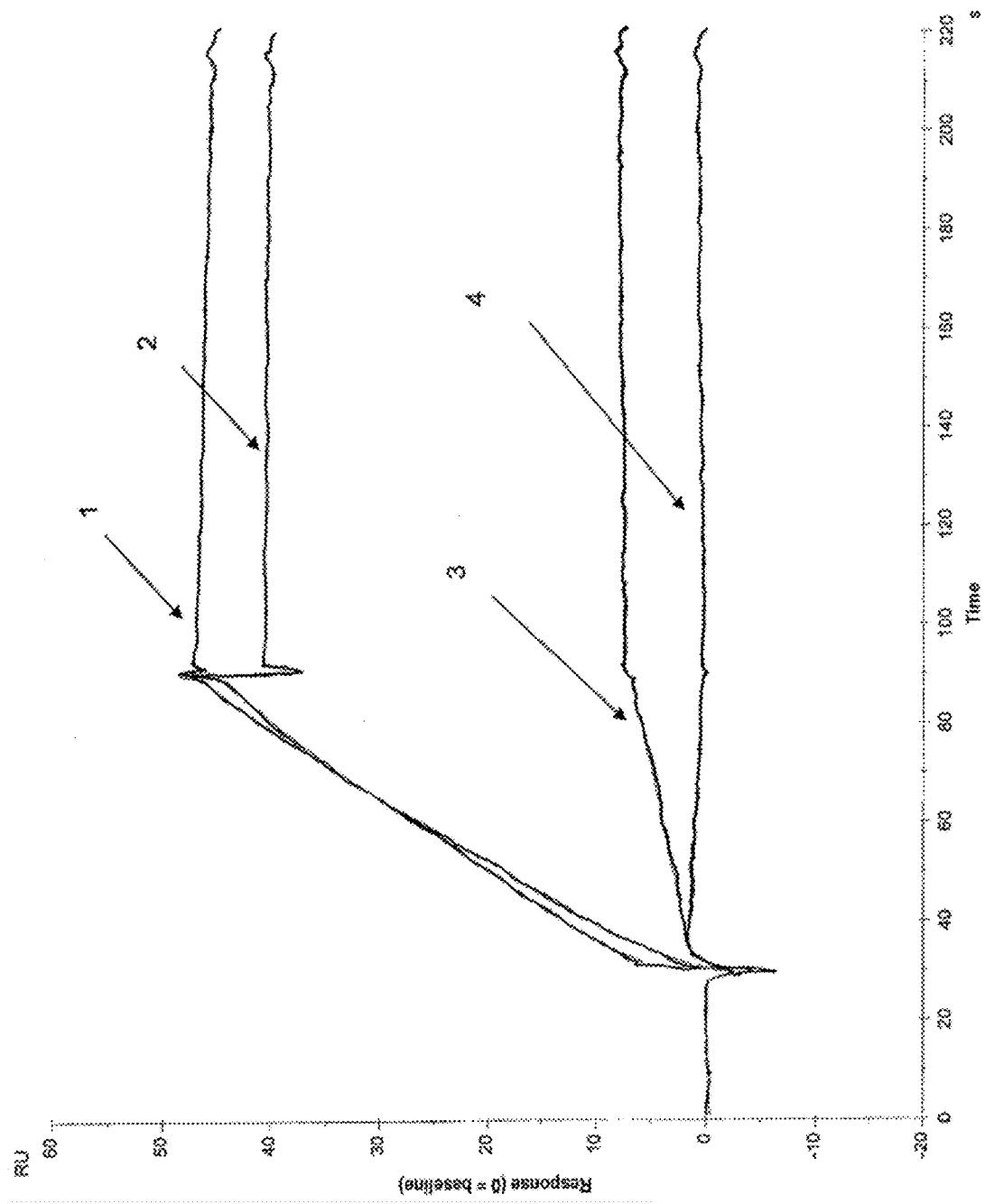
FIG. 5 shows the curves of binding (i) respectively of Factor VII, of Factor IX or of Factor X, present in various compositions to (ii) an aptamer specific for GLA-domain proteins which is immobilized on a support, in an assay according to the surface plasmon resonance technique. Along the x-axis: the time, expressed in seconds; along the y-axis, the resonance signal, expressed in arbitrary resonance units. Curve No. 1: preparation of human recombinant Factor IX (BeneFIX®); curve No. 2: preparation of human plasma Factor VII; curve No. 3: preparation of human plasma Factor X; curve No. 4: negative control preparation.

The binding measurement results represented in FIG. 5 show that the FIX-TGs obtained in the weak elution peak are indeed characterized by a significant affinity to Mapt-1, contrary to the majority of other forms of FIX-TG represented by the sample resulting from the purification process.

In example 3, it is shown that the Mapt-1 affinity support possesses a selectivity of binding for the species of GLA-domain proteins with the highest biological activity, in the case in point the most active species of transgenic recombinant human Factor IX.

Thus, in addition to enabling selective enrichment in Factor IX from the starting sample, the Mapt-1 affinity support makes it possible to increase the biological activity/Factor IX quantity ratio.

Example 4: Purification of Various GLA-Domain Proteins with an Affinity Support on which Anti-GLA Aptamers are Immobilized In example 4, it was shown that an affinity support on which anti-GLA aptamers are immobilized is successfully used for purifying a variety of GLA-domain proteins.

More specifically, it was shown in example 4 that an affinity support on which Mapt-1 anti-GLA aptamers are immobilized selectively retains Factor VII, Factor IX and Factor X.

Figure 6:
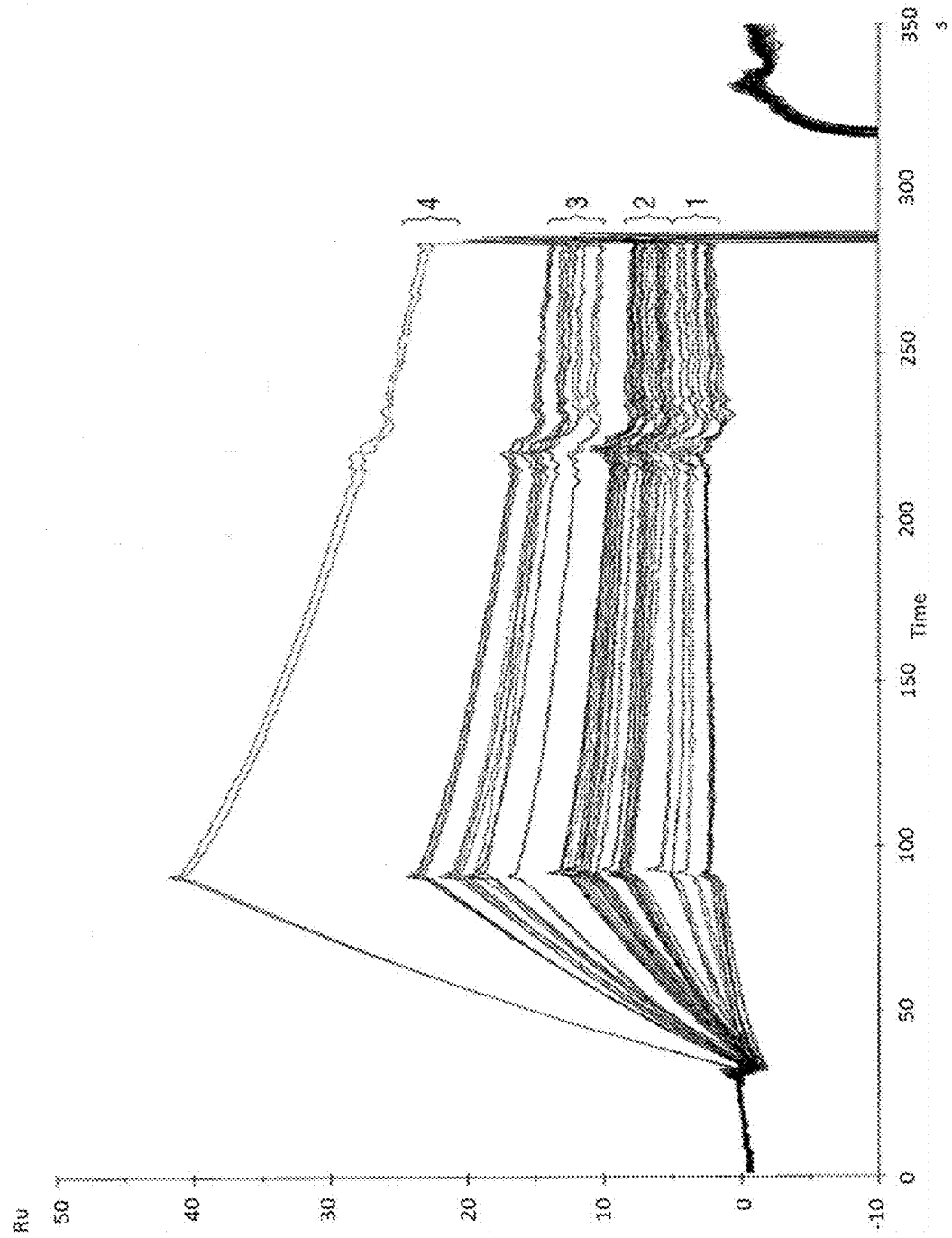
FIG. 6 shows the curves of binding of a diversity of nucleic acids of the invention to recombinant human Factor IX which is immobilized on a support, in an assay according to the surface plasmon resonance technique. Along the x-axis: the time, expressed in seconds; along the y-axis, resonance signal, expressed in arbitrary resonance units. Curves "1": low-affinity nucleic acids; curves "2": intermediate-affinity nucleic acids; curves "3": high-affinity nucleic acids; curves "4": very high-affinity nucleic acid.

5.1.1. Experimental Conditions
Binding Measurement: Biacore T100 Apparatus
  Chip: Mapt-1 immobilized on a streptavidin surface (Chip SA, GE) at 3596 RU on the active flow cell No. 2 (FC2). Buffer for running and diluting samples: 50 mM Tris/50 mM NaCl/10 mM CaCl$_2$/4 mM MgCl$_2$/pH=7.4
  Flow rate: 30 µl/min injection for 60 s, dissociation for 120 s
  Signal: FC2 signal corrected for the flow cell No. 1 signal which is the blank
  Regeneration: 10 mM EDTA in 50 mM Tris, pH=7.4.
5.1.2. Results
  The results are given in FIG. 5.
  FIG. 6 shows that the Mapt-1 affinity support selectively retains a variety of GLA-domain proteins, in the case in point a variety of human GLA-domain coagulation proteins such as Factor VII, Factor IX and Factor X.

Example 5: Capture of Nucleic Acid Aptamers According to the Invention by Human Factor IX Immobilized on a Support A solid support on which purified recombinant human Factor IX molecules were immobilized was produced. A purified preparation of recombinant human Factor IX sold under the name Benefix® by the company Wyeth was used.

Human Factor IX was immobilized on carboxymethyl dextran activated with NHS-EDC and which binds to the free amines present on FIX.

The human recombinant Factor IX is thus immobilized with an immobilization rate of 3153 RU (1 RU corresponds approximately to 1 pg of product immobilized per mm$^2$).

Nucleic aptamers of the invention (purity: 99%), respectively the aptamers having the sequences SEQ ID Nos. 3 and 6 to 35, were diluted in run buffer (50 mM Tris, 10 mM CaCl$_2$, 4 mM MgCl$_2$, pH 7.5) in order to obtain as many aptamer samples as distinct aptamers to be tested.

Each sample was injected sequentially onto the same chip (solid support) containing the immobilized human recombinant FIX. Controls are obtained by injecting blanks containing only run buffer. All the injections were carried out with a flow rate of 30 µl/min for 60 sec; after the injection, run buffer was injected onto the chip at an identical flow rate for 120 sec.

Elution buffer (10 mM EDTA) was then injected for 60 sec with a flow rate of 30 µl/min to uncouple the aptamer from the immobilized human FIX.

The chip makes it possible to observe in real time the formation and the disruption of interactions between the immobilized human recombinant FIX and each of the aptamers, having the sequences SEQ ID Nos. 3 and 6 to 35, tested, through surface plasmon resonance (SPR). Binding to the immobilized recombinant human FIX generates an increase in signal expressed in resonance units (RU) recorded by the apparatus (FIG. 6). These analyses are carried out with the Biacore T100 SPR apparatus (GE). The modeling of the recorded interactions is carried out by means of the Biaevaluation software (GE).

The results obtained show that all the nucleic aptamers tested bind with significant affinity to recombinant human plasma Factor IX.

The results of FIG. 6 also show that the 30 aptamers tested can be classified in four main groups, according to their level of affinity for human Factor IX.

The very high affinity for human Factor IX of the aptamers classified in group 4 as shown in FIG. 6 may in particular be noted. Out of the 30 aptamers tested, the aptamer with the highest affinity for human Factor IX, which is designated Mapt-1.2, consists of the aptamer having the sequence SEQ ID No. 35 [Mapt-1.2-CS].

Example 6: Capture of Nucleic Acid Aptamers According to the Invention by Human Factor IX Immobilized on a Support A solid support on which purified recombinant human Factor IX molecules were immobilized was produced. A purified preparation of recombinant human Factor IX sold under the name Benefix® by the company Wyeth was used.

Human Factor IX was immobilized on carboxymethyl dextran activated with NHS-EDC and which binds to the free amines present on FIX.

The recombinant human Factor IX is thus immobilized with an immobilization rate of 3153 RU (1 RU corresponds approximately to 1 pg of product immobilized per $mm^2$).

Nucleic aptamers of the invention (purity: 99%), respectively the aptamers having the sequences SEQ ID No. 35 [Mapt-1.2-CS] and SEQ ID No. 36 [Mapt-1.2-CSO], were diluted in run buffer (50 mM Tris, 10 mM $CaCl_2$, 4 mM $MgCl_2$, pH 7.5) in order to obtain as many aptamer samples as distinct aptamers to be tested.

The Mapt-1.2.-CSO aptamer having the sequence SEQ ID No. 36 is derived from the nucleic acid with the structure: 5'-SEQ ID No. 1-SEQ ID No. 35-SEQ ID No. 2 that is 80 nucleotides in length. More specifically, the Mapt-1.2.-CSO aptamer having the sequence SEQ ID No. 36 consists of the nucleic acid ranging from the nucleotide in position 10 and terminated with the nucleotide in position 49 of the nucleic acid with the structure: 5'-SEQ ID No. 1-SEQ ID No. 35-SEQ ID No. 2.

Each sample was injected sequentially onto the same chip (solid support) containing the immobilized recombinant human FIX. Controls are obtained by injecting blanks containing only run buffer. All the injections were carried out with a flow rate of 30 µl/min for 60 sec; after the injection, run buffer was injected onto the chip at an identical flow rate for 120 sec.

Elution buffer (10 mM EDTA) was then injected for 60 sec with a flow rate of 30 µl/min to uncouple the aptamer from the immobilized human FIX.

Figure 7:
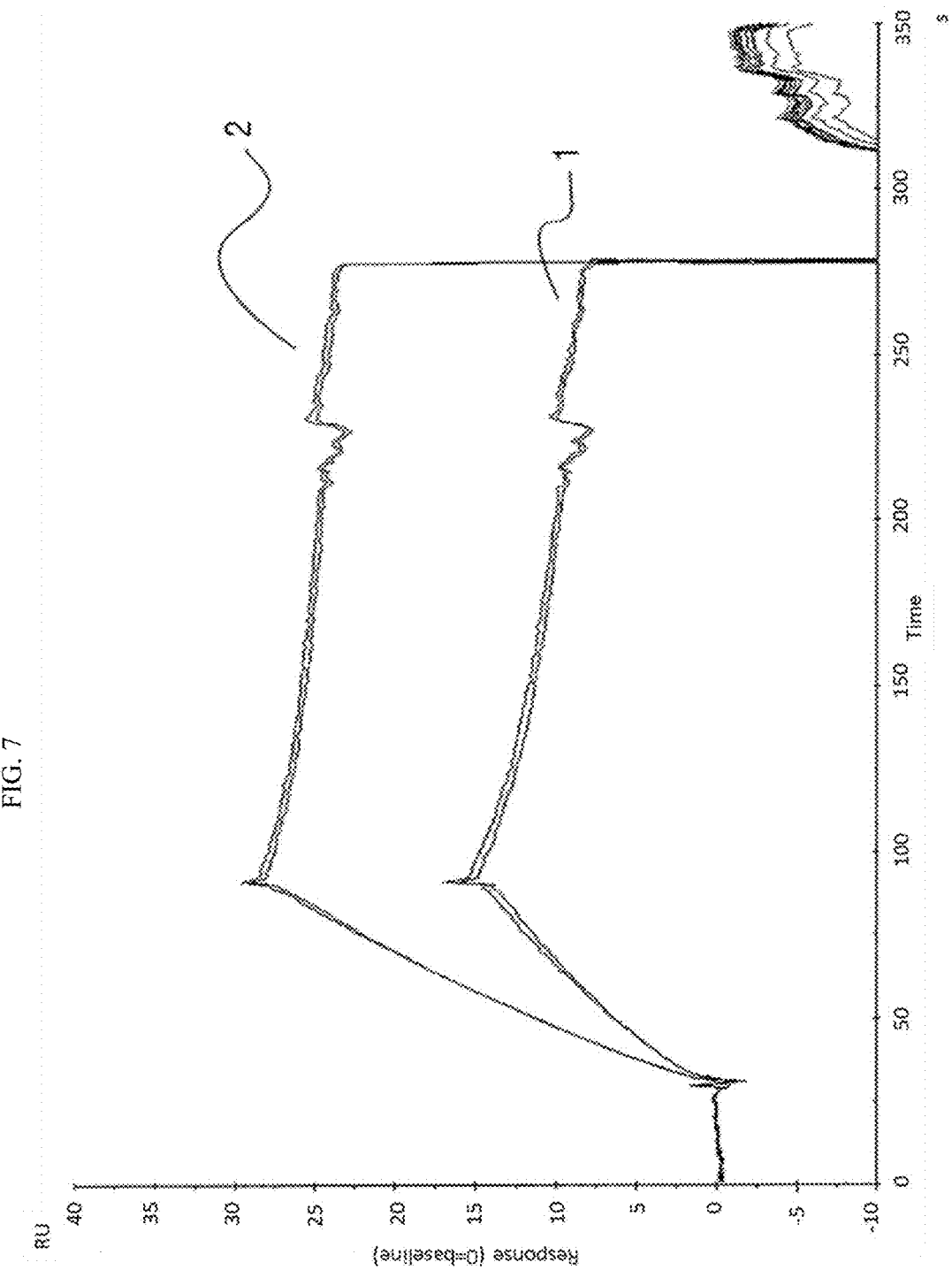
FIG. 7 shows the curves of binding of the nucleic acid aptamers "Mapt-1.2.-CS" and "Mapt-1.2.-CSO" to recombinant human Factor IX which is immobilized on a support, in an assay according to the surface plasmon resonance technique. Along the x-axis: the time, expressed in seconds; along the y-axis, resonance signal, expressed in arbitrary resonance units. Curve No. 1 is the curve of binding obtained with the Mapt-1.2.-CS aptamer. Curve No. 2 is the curve of binding obtained with the Mapt-1.2.-CSO aptamer.

The chip makes it possible to study in real time the formation and the disruption of interactions between the immobilized recombinant human FIX and each of the aptamers, having the sequences SEQ ID No. 35 [Mapt-1.2-CS] and SEQ ID No. 36 [Mapt-1.2-CSO] tested, through surface plasmon resonance (SPR). Binding to the immobilized recombinant human FIX generates an increase in the signal expressed in resonance units (RU) recorded by the apparatus (FIG. 7). These analyses are carried out with the Biacore T100 SPR apparatus (GE). The modeling of the recorded interactions is carried out by means of the Biaevaluation software (GE).

The results obtained show that the two nucleic aptamers tested bind with significant affinity to recombinant human plasma Factor IX.

The results of FIG. 7 also show that, of the two aptamers tested, Mapt-1.2.-CSO (SEQ ID No. 36) exhibits a level of affinity for human Factor IX that is significantly higher than the level of affinity of the Mapt-1.2.-CS aptamer (SEQ ID No. 35).

The results of FIG. 7 also show the excellent stability of the binding of the Mapt-1.2.-CSO aptamer (SEQ ID No. 36) to Factor IX.

It is recalled that the Mapt-1.2.-CS aptamer (SEQ ID No. 35) was the aptamer exhibiting the highest level of affinity of the 30 aptamers tested in example 5.

Example 7: Preparation of an Affinity Support

The affinity support was made from a solid support material consisting of a matrix on which streptavidin (streptavidin-agarose—Novagen®) was grafted.

A volume of 1 ml of gel was introduced into a container consisting of a column (i.d. 11 mm). The gel was washed with purified water, to remove the storage solvent.
The Gel Characteristics are:
  Biotin adsorption capacity: ≥85 nanomol/ml of gel
  Functional test: Capture>99% of biotinylated thrombin in 30 minutes at AT
  Other tests: Protease-free, endo/exonuclease-free, RNase-free
  Preservative: 100 mM sodium phosphate, pH 7.5, +$NaN_3$ 0.02.

The output of the packed column (gel bed height=1 cm) is connected to an absorbance detector fitted with a UV filter at 254 nm and a recording device.

Biotinylated anti-human FIX nucleic aptamers comprising the nucleic acid having the sequence SEQ ID No. 4 [Mapt-1-WS] are solubilized in purified water at a final concentration of 0.5 mg/0.187 ml, i.e. a final molar concentration of 0.1 mM. The solution of nucleic aptamers was activated at 95° C. according to the standard cycle, for immobilizing the aptamers on the solid support material.

The solution of nucleic aptamers was diluted beforehand with 4.8 ml of purified water then 1.5 ml of $Mg^{++}$ buffer (concentrated 5×).

The absorbance detector is adjusted to 1 AUFS (Absorbance Unit Full Scale) and the OD at 254 nm of this solution is recorded at 0.575 $AU_{254}$.

The solution of biotinylated nucleic aptamers is injected onto the prepacked streptavidin-agarose gel and recirculated with a peristaltic pump at a flow rate of 2.5 ml/minute, i.e. a contact time on the gel of 24 seconds (input/output I/O). Under these conditions, the OD at 254 nm stabilizes rapidly at 0.05 $AU_{254}$, which is 91% of the theoretical coupling, i.e. 0.455 mg of nucleic aptamers per milliliter of gel.

Washing with a buffer containing 10 mM $CaCl_2$+4 mM $MgCl_2$, then 2M NaCl, is carried out, in order to remove the nucleic aptamers which are not bound specifically to the streptavidin molecules grafted onto the solid support material.

Example 8: Method for Purifying Recombinant Human Factor IX

A. Use of an Affinity Support Comprising the Immobilized Mapt-1WS Aptamer

The aptamer affinity supports were tested on a purified preparation of human plasma FIX. It is specified that the purified preparation of human plasma FIX consists of a 60% pure FIX concentrate sold under the name Betafact® by the Laboratoire Français du Fractionnement et des Biotechnologies [French Laboratory of Fractionation and Biotechnologies] (LFB).

The affinity support was prepared in accordance with the protocol described in example 7. The aptamers consist of biotinylated anti-GLA aptamers that do not comprise a spacer chain and are known as Mapt-1, which comprise the nucleic acid having the sequence SEQ ID No. 4.

The affinity support used to carry out example 8 has a theoretical ligand density of 0.46 mg/ml. A gel volume of 1 ml was used.

The affinity support is equilibrated with a 0.05M Tris-HCl, 0.01M $CaCl_2$ buffer at pH 7.5.

A purified human plasma FIX load in a quantity of 200 IU (i.e. 800 µg) per milliliter of affinity support (gel) is used for the human FIX purification step.

The purified human plasma FIX solution, previously adjusted to 50 mM Tris+50 mM NaCl+4 mM $MgCl_2$+10 mM $CaCl_2$ at pH 7.5, is injected onto the aptamer-agarose gel (affinity support) with a peristaltic pump at a flow rate of 0.1 ml/minute, i.e. a contact time with the affinity support of 10 minutes (I/O).

After injection, the gel is washed with a 50 mM Tris+50 mM NaCl+4 mM $MgCl_2$+10 mM $CaCl_2$ buffer at pH 7.5.

A volume of 10 ml of nonadsorbed solution is recovered.

The FIX is eluted with a 20 mM Tris-HCl+10 mM EDTA buffer, at pH 7.5. The elution peak is collected according to the OD profile.

In order to regenerate the affinity support, a 20 mM Tris-HCl, 1M NaCl, 50% propylene glycol buffer, at pH 7.5, is used.

Figure 8:
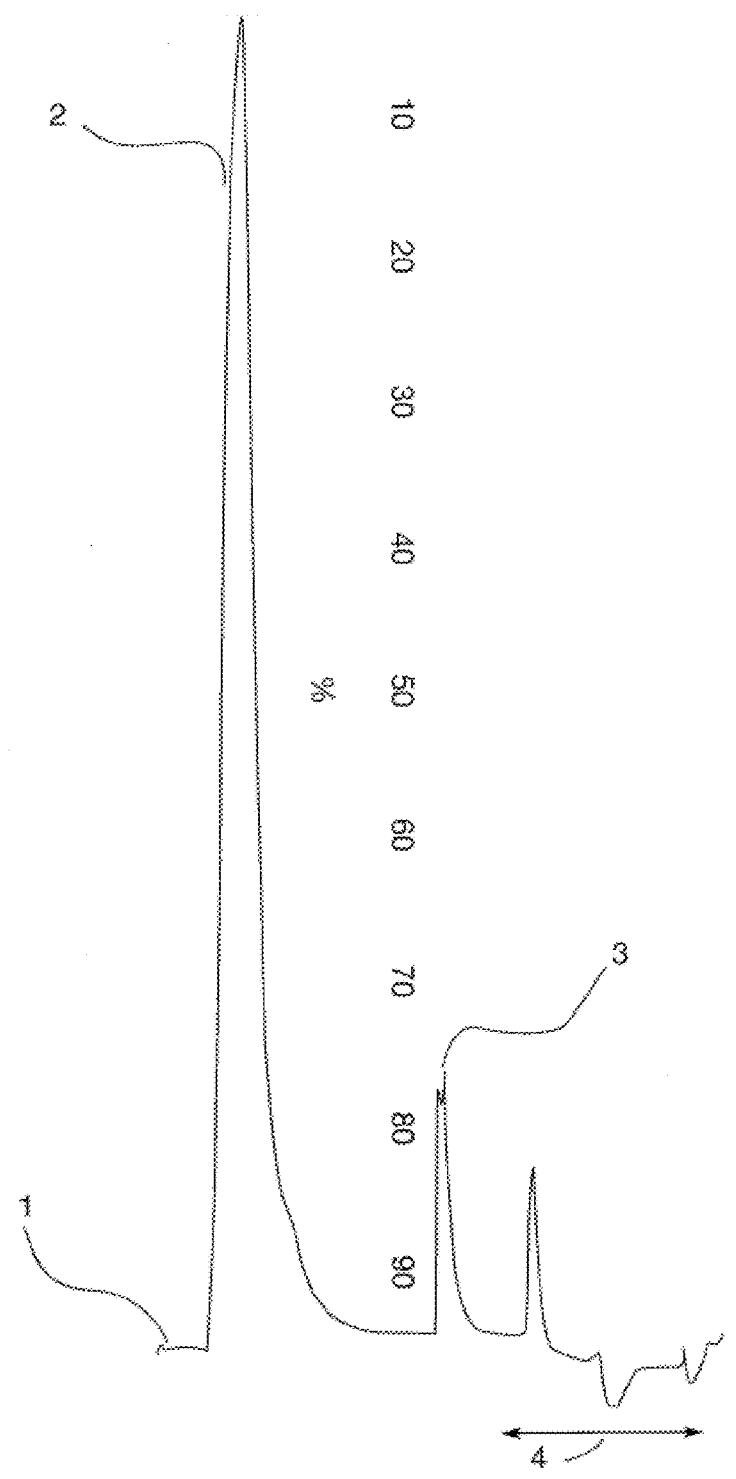
FIG. 8 shows a chromatography profile obtained when carrying out the method for purifying a human plasma Factor IX, produced with the affinity support on which anti-GLA nucleic aptamers are immobilized. Along the x-axis: the time; along the y-axis: the absorbance value (O.D.) at 254 nanometers. (1): moment of injection of the human plasma FIX concentrate; (2): nonretained fraction elimination peak; (3): purified FIX elution peak; (4): peaks generated during the chromatographic support regeneration step.

FIG. 8 shows a chromatography profile for human plasma FIX, with continuous monitoring of the absorbance values (OD) at 254 nanometers.

In FIG. 8, the injection (1) of the human plasma FIX concentrate is rapidly followed by the elimination peak (2) of the fraction not retained on the affinity support. The affinity support continues to saturate with the coagulation protein of interest: complexes between (i) the anti-GLA nucleic aptamers of the affinity support and (ii) the human plasma FIX molecules initially contained in the composition to be purified were formed. After running the composition to be purified, a step of washing the column with the previously specified washing buffer is performed. Then, the elution step is performed, by injecting the elution buffer solution comprising a final concentration of 10 mM of EDTA.

The absorption peak (3) in FIG. 8 shows the release of the human plasma FIX from the nucleic aptamer/recombinant FIX complexes, during the elution step.

It should be noted that the human plasma FIX molecules are released rapidly, and thus in a small volume. Consequently, by virtue of the affinity support of the invention, an elution solution is obtained with a high concentration of human plasma FIX protein.

After elution, an affinity support regeneration step was carried out, with a 20 mM Tris-HCl, 1M NaCl, 50% propylene glycol buffer at pH 7.5.

A chromatogram was produced and also an SDS-PAGE gel electrophoresis was carried out with a 4-12% bisacrylamide gradient without a reducing agent, with Coomassie blue staining. The results are shown in FIG. 9.

Figure 9:
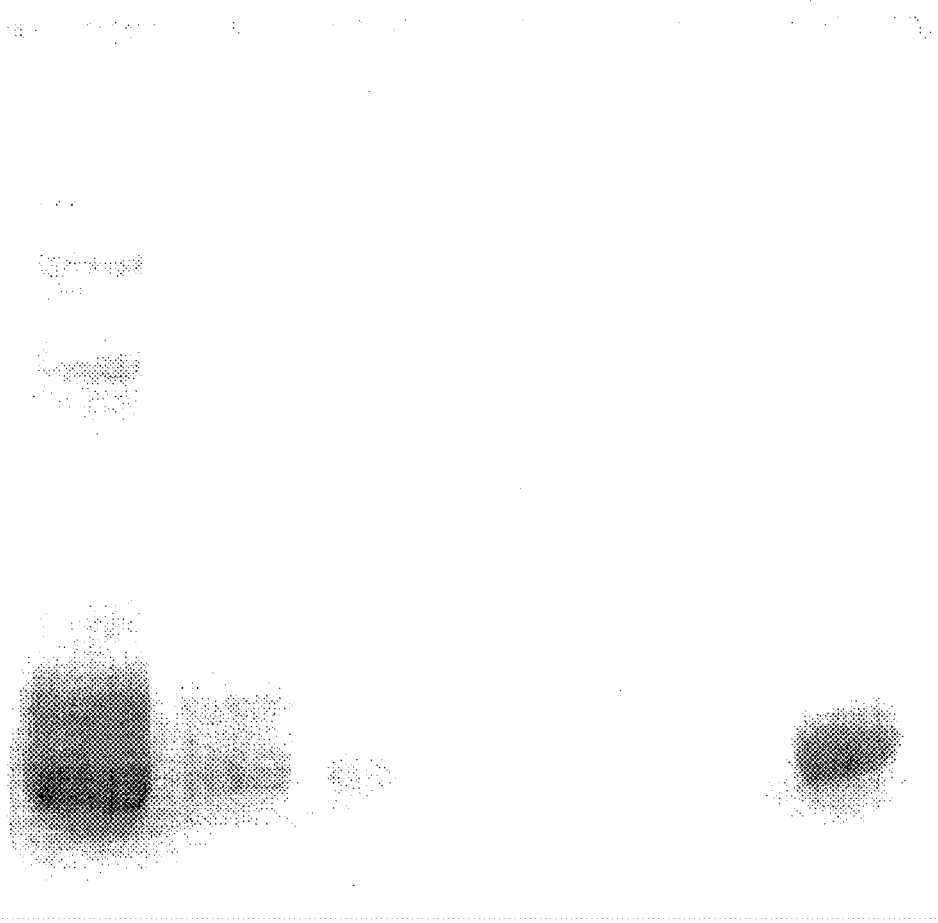
FIG. 9 is the image of an SDS-PAGE electrophoresis gel, with a gradient of from 4 to 12% of bisacrylamide without reducing agent, of proteins contained in a purified fraction of human plasma Factor IX, having undergone chromatography on an affinity support on which nucleic aptamers specific for GLA-domain proteins are grafted. The SDS-PAGE gel was treated with Coomassie blue. From left to right: lane 1 ("SM"): starting composition, human plasma Factor IX concentrate; lane 2 ("NR"): proteins contained in the fraction not retained on the affinity support; lane 3 ("E1"): proteins contained in the elution fraction E1; lane 4 ("E2"): proteins contained in the output from the affinity support, in the regeneration buffer; lane 5 ("E3"): proteins contained in the output from the affinity support, in the regeneration buffer; lane 6 ("T FIX"): purified fraction of human plasma Factor IX.

The analysis of the chromatogram in FIG. 9 shows that the eluate exhibits good chromatographic purity and the biological activity analysis is characterized by preservation of the functionality of the Factor IX.

These analyses also show that the value of the "FIX activity"/"Factor IX quantity" ratio found in the eluate fraction is almost identical to the value of the "FIX activity"/"Factor IX quantity" ratio found in the starting product: this value is 1.2. These results show that the FIX has not been modified during the method for purifying by affinity chromatography.

The results of example 8-A show the ability of the Mapt-1WS aptamer that was immobilized on the affinity support in the absence of a spacer chain, for example in the absence of a polyethylene glycol spacer chain, to purify the human factor IX from a complex starting medium containing numerous plasma-derived impurities.

B. Use of an Affinity Support Comprising the Immobilized Mapt-1.2.-CSO Aptamer

An affinity support on which molecules of the biotinylated Mapt-1.2.-CSO aptamer comprising a PEG (C18) spacer chain were immobilized, was used.

The Mapt-1.2.-CSO aptamer comprises the nucleic acid having the sequence SEQ ID No. 36.

With this affinity support, human plasma Factor IX was purified.

The affinity support was prepared in accordance with the protocol described in example 7.

The affinity support used to carry out example X4 has a theoretical ligand density of 0.25 mg/ml. A gel volume of 1 ml was used.

The affinity support is equilibrated with a 0.05M Tris-HCl, 0.01M $CaCl_2$ buffer at pH 7.5.

A 50%-pure human plasma FIX load in a quantity of 207 µg per milliliter of affinity support (gel) is used for the human FIX purification step.

The purified human plasma FIX solution, previously adjusted to 10 mM $CaCl_2$ and pH 7.5, is injected onto the aptamer-agarose gel (affinity support) with a peristaltic pump at a flow rate of 0.05 ml/minute, i.e. a contact time on the affinity support of 20 minutes (I/O).

After injection, the gel is washed in 50 mM Tris+50 mM NaCl+4 mM $MgCl_2$+10 mM $CaCl_2$ buffer at pH 7.5.

A volume of 10 ml of nonadsorbed solution is recovered.

The FIX is eluted with a 50 mM Tris-HCl+10 mM EDTA buffer at pH 7.5. The elution peak is collected according to the OD profile.

In order to regenerate the affinity support, a 1M NaCl, 50% propylene glycol regeneration buffer, at pH 7.5, was used.

Figure 10:
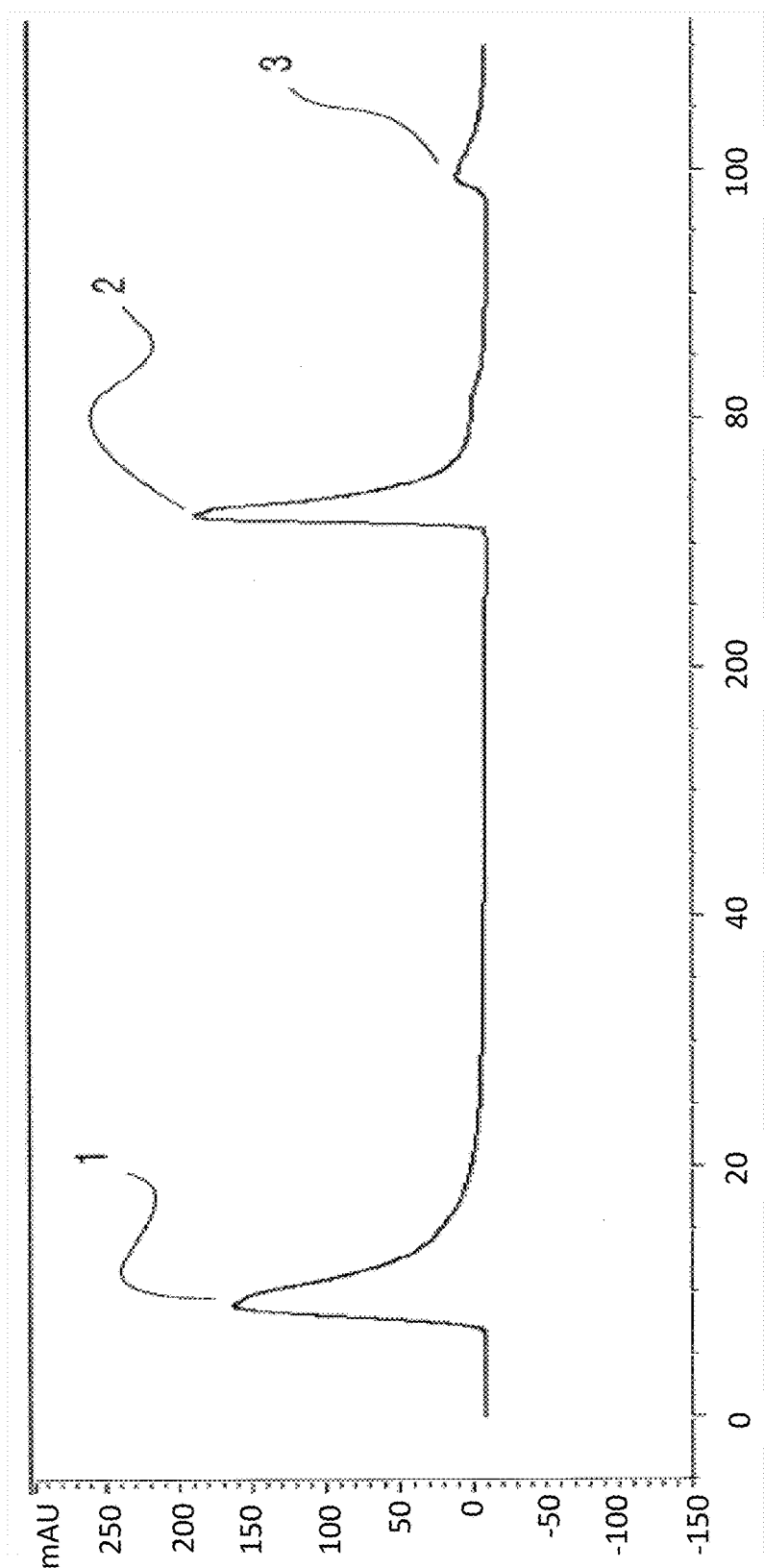
FIG. 10 shows a chromatography profile obtained when carrying out the method for purifying a human plasma Factor IX, produced with the affinity support in which anti-GLA nucleic aptamers are immobilized. Along the x-axis; the time; along the y-axis: the absorbance value (O.D.) at 254 nanometers. (1): nonretained fraction; (2): purified human FIX elution peak; (3) chromatographic support regeneration peak.

The chromatography profile is shown in FIG. 10. In FIG. 10, the injection of the human plasma FIX concentrate is followed by the elimination peak (1) for the fraction not retained on the affinity support. The affinity support continues to saturate with the coagulation protein of interest: complexes between (i) the anti-GLA nucleic aptamers of the affinity support and (ii) the human plasma FIX molecules initially contained in the composition to be purified were formed. After running the composition to be purified, a step of washing the column with the previously specified washing buffer is carried out. Then, the elution step is carried out, by injecting the elution buffer solution comprising a final concentration of 10 mM of EDTA.

It is specified that the nonretained fraction contains 57% by weight of the proteins contained in the starting sample, the eluate fraction represents 40% by weight of the proteins contained in the starting sample and the regeneration fraction represents 3% by weight of the proteins contained in the starting sample.

The absorption peak (3) in FIG. 10 shows the release of human plasma FIX from the nucleic aptamer/recombinant FIX complexes, during the elution step.

Figure 11:
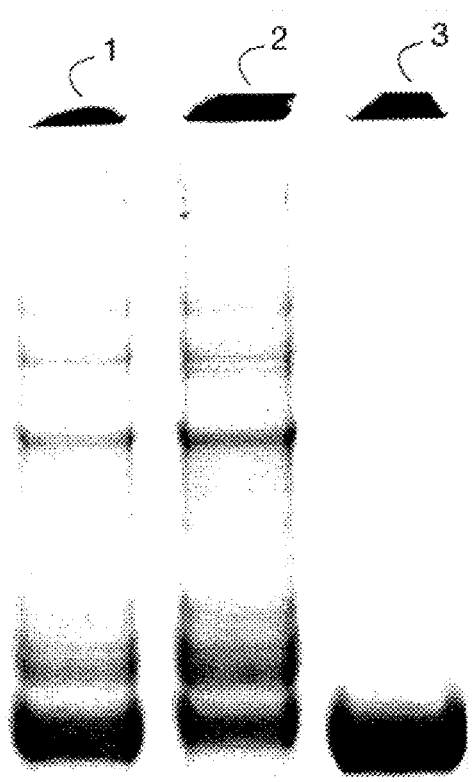
FIG. 11 is the image of an SDS-PAGE electrophoresis gel, with a gradient of 4 to 12% of bisacrylamide without reducing agent, of proteins contained in a purified fraction of human plasma Factor IX, having undergone chromatography on an affinity support on which nucleic aptamers specific for GLA-domain proteins are grafted. The SDS-PAGE gel was treated with Coomassie blue. From left to right: lane 1 ("Start"): starting composition, human plasma Factor IX concentrate; lane 2 ("Not retained"): proteins contained in the fraction not retained on the affinity support; lane 3 ("Eluate"): proteins contained in the elution fraction.

In addition, FIG. 11 shows the excellent ability of the affinity support, on which molecules of the Mapt-1.2.-CSO aptamer are immobilized, to purify human Factor IX.

The results of FIG. 11 show that the eluate fraction exhibits good electrophoretic purity.

The results of example 8-B show the ability of the Mapt-1.2.-CSO aptamer, that was immobilized on the affinity support, to purify human Factor IX from a complex starting medium containing numerous plasma-derived impurities.

These results are particularly unexpected because the Mapt-1.2.-CSO aptamer comprises only part of the "core sequence" of the Mapt-1.2-CS aptamer and comprises a 5' region that consists of the 3' part of a region intended to be recognized by consensus primers. More specifically, the Mapt-1.2.-CSO aptamer comprises the region of 40 nucleotides nt10-nt49 of the nucleic acid having the sequence 5'-SEQ ID No. 1-SEQ ID No. 3-SEQ ID No. 2-3' that is 80 nucleotides in length.

Example 9: Method for Purifying Recombinant Human Factor VII

Tests for purification of recombinant Factor IX produced in the milk of pigs transgenic for human Factor IX were carried out. The milk of transgenic pigs comprises a mixture of (i) active transgenic recombinant human Factor IX having a correctly gamma-carboxylated GLA domain and (ii) inactive transgenic recombinant human Factor IX having an incorrectly gamma-carboxylated GLA domain.

Transgenic recombinant human FIX produced in pigs and prepurified by chromatography on an MEP HyperCel® support was dialyzed against the buffer used for the equilibration of the chromatography support in order to remove the sodium citrate. The prepurification step on MEP Hyper-Cel resulted in a composition containing human Factor IX at 1.8% purity.

The affinity support was prepared in accordance with the protocol described in example 7.

The Mapt-1WS affinity support without spacer chain used to carry out example 9 has a theoretical ligand density of 0.46 mg/ml. A gel volume of 1 ml was used. The Mapt-1WS aptamer comprises the nucleic acid having the sequence SEQ ID No. 4.

The affinity support is equilibrated with a 0.05M Tris-HCl, 0.01M $CaCl_2$ buffer at pH 7.5.

A load of 302 IU (i.e. 1200 µg) of prepurified recombinant human FIX derived from transgenic sow's milk, per milliliter of affinity support (gel), is used for the human FIX purification step.

The purified human plasma FIX solution, previously adjusted to 10 mM $CaCl_2$ and pH 7.5, is injected onto the aptamer-agarose gel (affinity support) with a peristaltic pump at a flow rate of 0.1 ml/minute, i.e. a contact time with the affinity support of 10 minutes (I/O).

There was no apparent modification of the starting product when the calcium chloride was added.

After injection, the gel is washed in 50 mM Tris+50 mM NaCl+4 mM $MgCl_2$+10 mM $CaCl_2$ buffer at pH 7.5.

A volume of 10 ml of nonadsorbed solution is recovered.

The FIX is eluted with a 20 mM Tris-HCl+10 mM EDTA buffer at pH 7.5. The elution peak is collected according to the OD profile.

In order to regenerate the affinity support, a 20 mM Tris-HCl, 1M NaCl, 50% propylene glycol regeneration buffer, at pH 7.5, is used.

Figure 12:
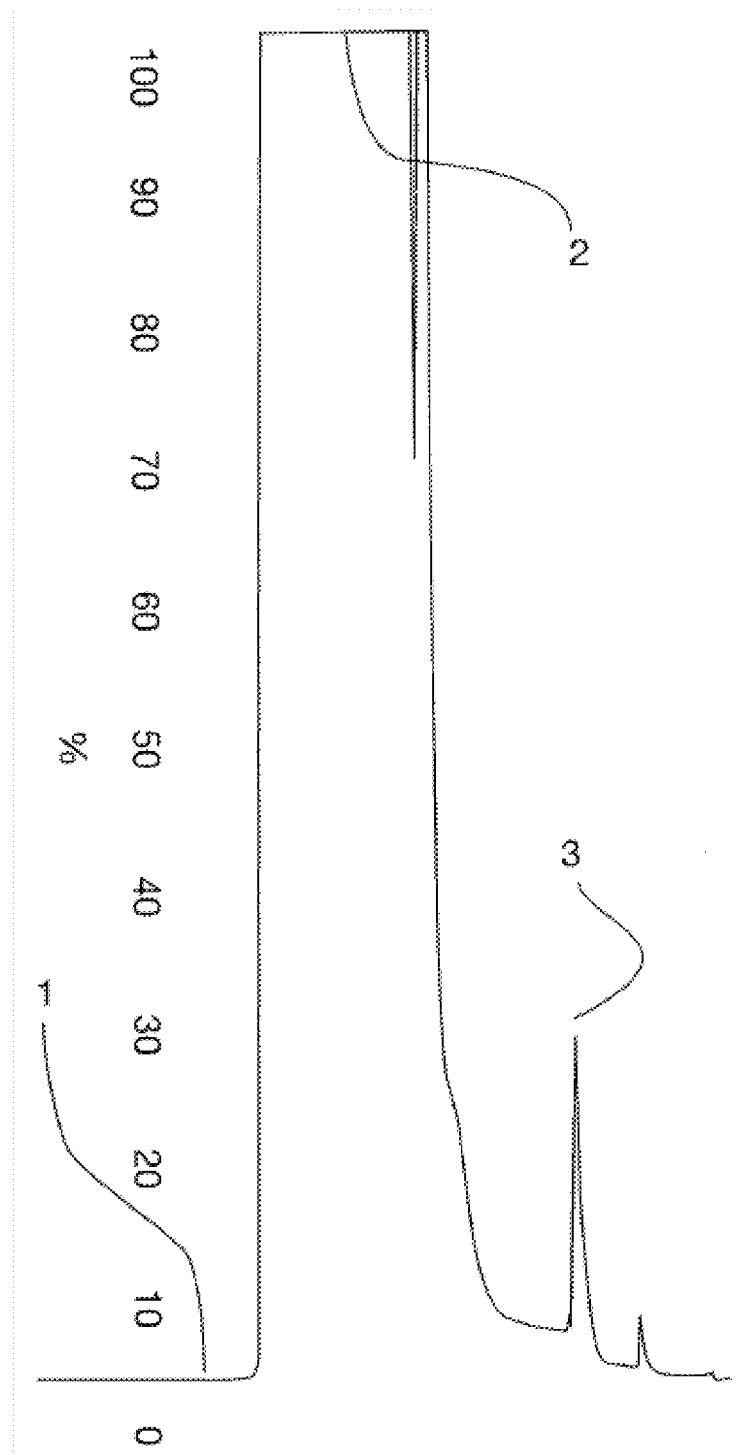
FIG. 12 shows a chromatography profile obtained when carrying out the method for purifying a transgenic human Factor IX, produced in the milk of a transgenic sow, with the affinity support on which anti-GLA nucleic aptamers are immobilized. Along the x-axis: the time; along the y-axis: the absorbance value (O.D.) at 254 nanometers. (1): moment of injection of the transgenic FIX, (2): nonretained fraction; (3): elution fraction.
Figure 13:
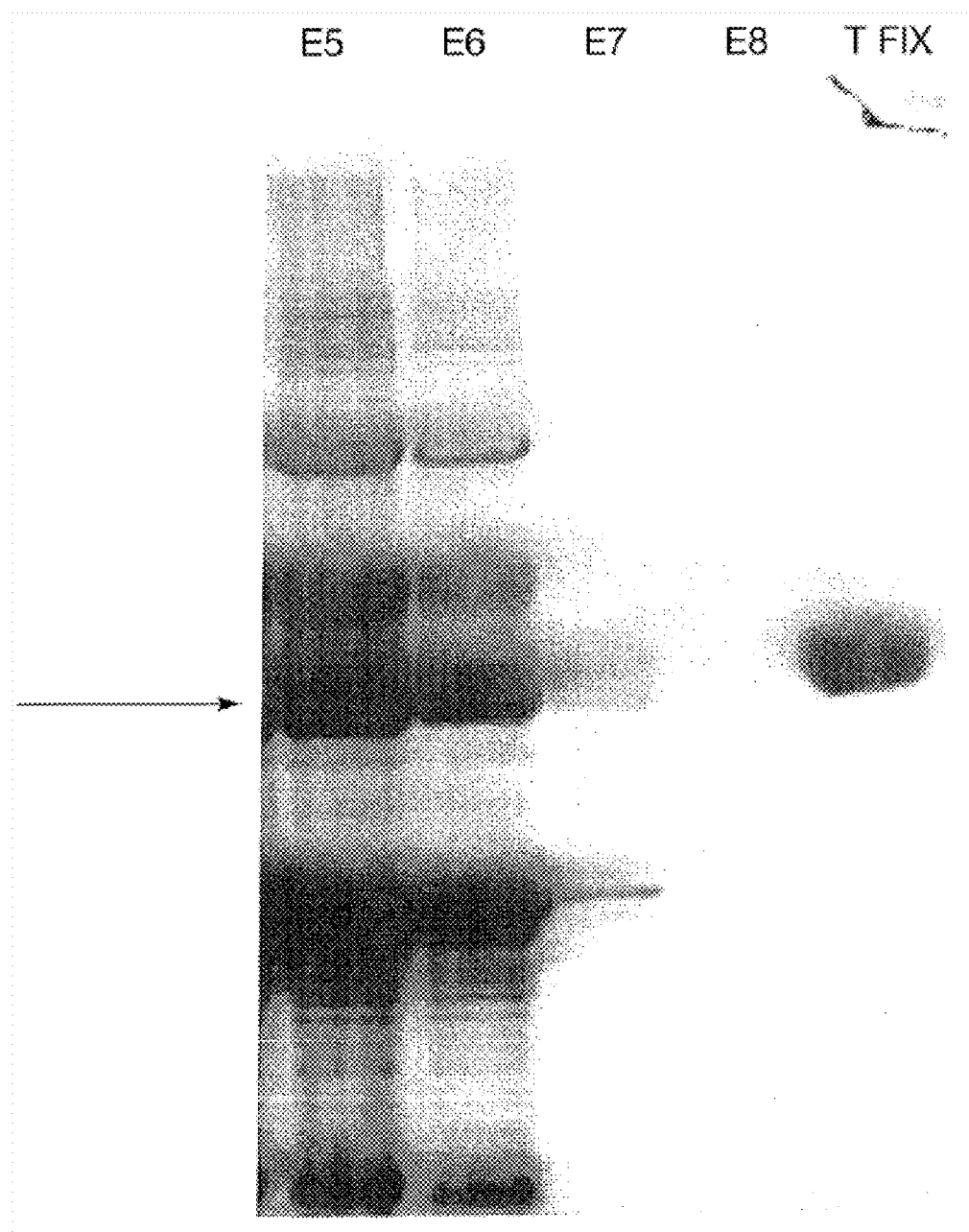
FIG. 13 is the image of an SDS-PAGE electrophoresis gel of the proteins contained in a prepurified fraction of recombinant human Factor IX produced in the milk of a transgenic sow, having undergone chromatography on an affinity support on which nucleic aptamers specific for GLA-domain proteins are grafted. The SDS-PAGE gel was treated with Coomassie blue. From left to right: lane 1 ("E5", "Start"): starting composition, transgenic human Factor IX prepurified on MEP HyperCel®; lane 2 ("E6", "Not Retained"): proteins contained in the fraction not retained on the affinity support; lane 3 ("E7", "Elution"): proteins contained in the elution fraction; lane 4 ("E8", "Regeneration"): proteins contained in the regeneration fraction; lane 5 ("T FIX", "Pure FIX control"): purified FIX control. Arrow: position of migration of FIX.

FIG. 12 shows a chromatography profile for human plasma FIX, with continuous monitoring of the absorbance values (OD) at 254 nanometers.

In FIG. 12, the injection (1) of human plasma FIX concentrate is rapidly followed by the elimination peak (2) of the fraction not retained on the affinity support. The affinity support continues to saturate with the coagulation protein of interest: complexes between (i) the anti-GLA nucleic aptamers of the affinity support and (ii) the transgenic human FIX molecules initially contained in the composition to be purified were formed. After running the composition to be purified, a step of washing the column with the previously specified washing buffer is carried out.

Then, the elution step is carried out by injecting the elution buffer solution comprising a final concentration of 10 mM of EDTA.

The absorption peak (3) in FIG. 12 shows the release of human transgenic FIX from the nucleic aptamer/recombinant FIX complexes, during the elution step.

It should be noted that the transgenic human FIX molecules are released rapidly, and thus in a small volume. Consequently, by virtue of the affinity support of the invention, an elution solution is obtained with a high concentration of transgenic human FIX protein.

After elution, a step of regenerating the affinity support is carried out, with a 20 mM Tris-HCl, 10 mM EDTA buffer at pH 7.5.

A chromatogram was produced and an SDS-PAGE gel electrophoresis was carried out with Coomassie blue staining. The results are shown in FIG. 12.

The analysis of the chromatogram in FIG. 12 shows that the eluate exhibits good chromatographic purity and is characterized by the fact that the Factor IX functionality is maintained with a selection of the whole and thus active GLA-domain proteins.

The results of example 9 show the ability of the Mapt-1WS aptamer without a spacer chain that was immobilized on the affinity support in the absence of a spacer chain, for example in the absence of a polyethylene glycol spacer chain, to purify human Factor IX from a complex starting medium containing numerous plasma-derived impurities.

The results of the step of purification by chromatography are also shown in table T1 below.

TABLE T1

|  | Specific activity (IU/mg) | Purity (%) | Increase in purity |
|---|---|---|---|
| Starting product | 4.0 | 1.8 | 1.0 |
| Fraction not retained | 3.8 | 1.7 | 0.9 |
| Elution fraction | 104.5 | >46.1 | >26.0 |
| Regeneration fraction | 1.4 | 0.6 | 0.3 |

The results presented in table T1 show that the affinity support prepared in example 9 shows an excellent ability to purify human factor IX, and more specifically recombinant human Factor IX produced in the milk of a sow transgenic for human Factor IX. In particular, the results of table T1 show that an increase in purity of at least 26-fold is obtained.

Example 10: Capture of Nucleic Acid Aptamers According to the Invention by Human Factor VII Immobilized on a Support A solid support was produced on which purified recombinant human Factor VII molecules were immobilized. A purified preparation of recombinant human Factor VII sold under the name Novoseven® by the company Laboratoires Français du Fractionnement et des Biotechnologies (LFB) [French Laboratory of Fractionation and Biotechologies] was used.

Human factor VII is immobilized on carboxymethyl dextran activated with NHS-EDC and which binds to the free amines present on FIX.

Recombinant human Factor VII is thus immobilized with an immobilization rate of 2525 RU (1 RU corresponds approximately to 1 pg of product immobilized per $mm^2$).

Nucleic aptamers of the invention (purity: 99%) were diluted in run buffer (50 mM Tris, 10 mM $CaCl_2$, 4 mM MgCl$_2$, pH 7.5) in order to obtain as many aptamer samples as distinct aptamers to be tested.

Each sample was injected sequentially onto the same chip (solid support) containing the immobilized recombinant human FVII. Controls are obtained by injecting blanks containing only run buffer. All the injections were carried out with a flow rate of 30 µl/min for 60 sec; after the injection, run buffer was injected onto the chip at an identical flow rate for 120 sec.

Elution buffer (5 mM EDTA) was then injected for 60 sec with a flow rate of 30 µl/min to recover the aptamer from the immobilized human FVII.

Figure 14:
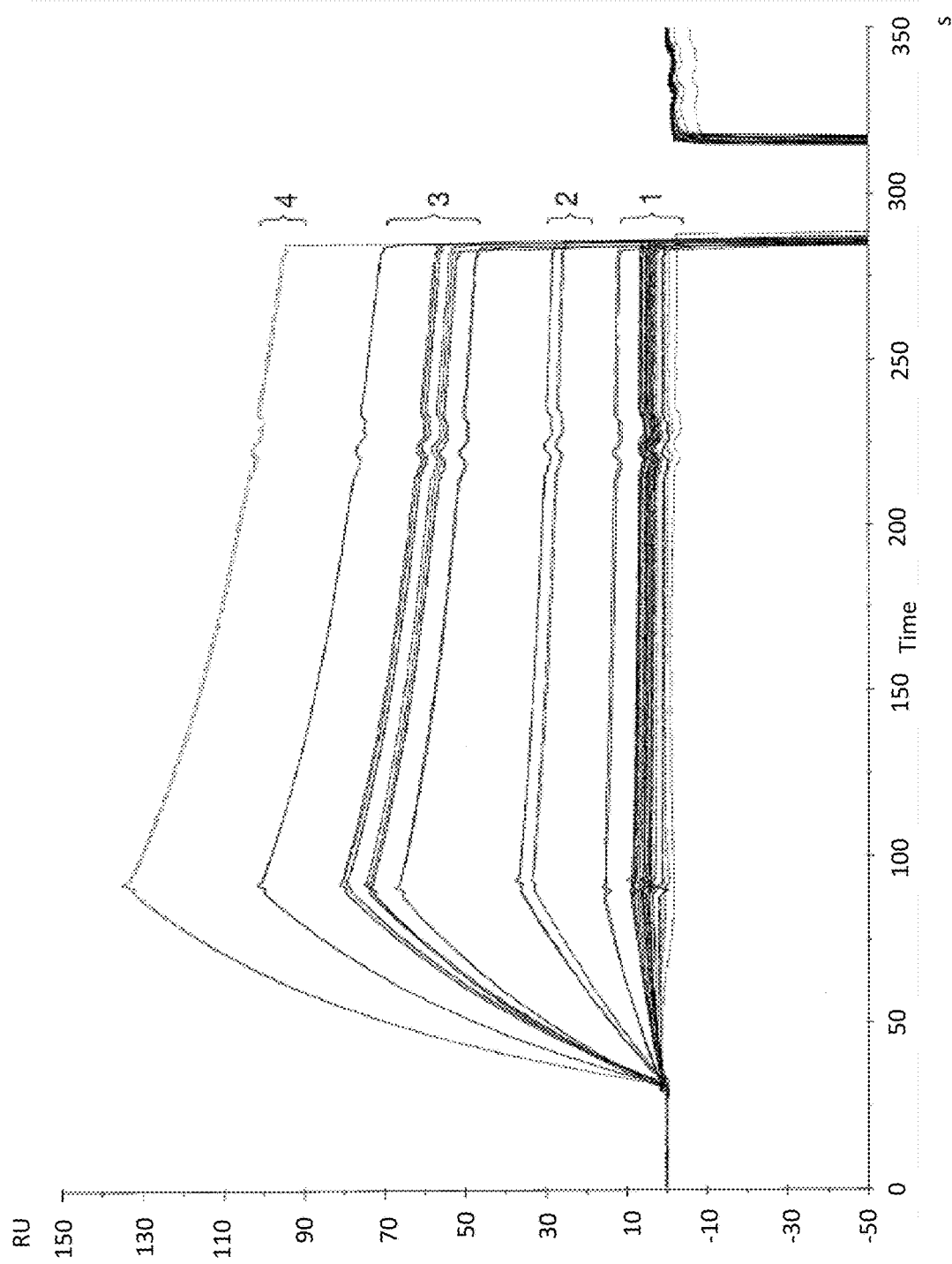
FIG. 14 shows the curves of binding of a diversity of nucleic acids of the invention to recombinant human Factor IX which is immobilized on a support, in an assay according to the surface plasmon resonance technique. Along the x-axis: the time, expressed in seconds; along the y-axis, resonance signal, expressed in arbitrary resonance units. Curves "1": low-affinity nucleic acids; curves "2": intermediate-affinity nucleic acids; curves "3": high-affinity nucleic acids; curves "4": very high-affinity nucleic acid.

The chip makes it possible to study in real time the formation and the disruption of the interactions between the immobilized recombinant human Factor VII and each of the aptamers tested, through surface plasmon resonance (SPR). Binding to the immobilized recombinant human FVII generates an increase in the signal expressed in resonance units (RU) recorded by the apparatus (FIG. 14). These analyses are carried out with the Biacore T100 SPR apparatus (GE). The modeling of the recorded interactions was carried out by means of the Biaevaluation software (GE).

The results obtained show that all the nucleic aptamers tested bind with significant affinity to recombinant human plasma Factor IX.

The results of FIG. 14 also show that the 27 aptamers tested can be classified in four main groups, according to their level of affinity for human Factor VII.

The very high affinity for human Factor VII of the aptamers classified in group 4 as shown in FIG. 14 should in particular be noted. Out of the 27 aptamers tested, the aptamer with the highest affinity for human Factor IX, which is designated Mapt-2.2, consists of the aptamer having the sequence SEQ ID No. 38, Mapt-2.2-CS.

Example 11: Method for Purifying Human Plasma Factor VII

A. Use of an Affinity Support Comprising the Immobilized Mapt-2-CS Aptamer

The aptamer affinity supports were tested on a purified preparation of human plasma FVII. It is specified that the purified preparation of human plasma FVII consists of a 98% pure FVII concentrate sold under the name ACSET® by the Laboratoire Français du Fractionnement et des Biotechnologies (LFB) [French Laboratory for Fractionation and Biotechnologies].

The affinity support was prepared in accordance with the protocol described in example 7. The affinity support of example 11-A comprises the Mapt-2-CS aptamer comprising the nucleic acid having the sequence SEQ ID No. 37 which was immobilized.

The affinity support used to carry out example 11-A has a theoretical ligand density of 0.40 mg/ml. A gel volume of 1 ml was used.

The affinity support is equilibrated with a 0.05M Tris-HCl, 0.01M CaCl$_2$, 0.05 mM MgCl$_2$ buffer at pH 7.5.

A purified human plasma FVII load is used for the human FVII purification step.

The purified human plasma FVII solution, previously adjusted to 4 mM MgCl$_2$ and 10 mM CaCl$_2$ and pH 7.5, is injected onto the aptamer-agarose gel (affinity support) with a peristaltic pump at a flow rate of 0.1 ml/minute, i.e. a contact time with the affinity support of 10 minutes (I/O).

After injection, the gel is washed in 50 mM Tris+50 mM NaCl+4 mM MgCl$_2$+10 mM CaCl$_2$ buffer at pH 7.5.

A volume of 10 ml of nonadsorbed solution is recovered.

The FVII is eluted with a 20 mM Tris-HCl+10 mM EDTA buffer at pH 7.5. The elution peak is collected according to the OD profile.

In order to regenerate the affinity support, a 20 mM Tris-HCl, 1M NaCl, 50% propylene glycol buffer at pH 7.5 is used.

Figure 15:
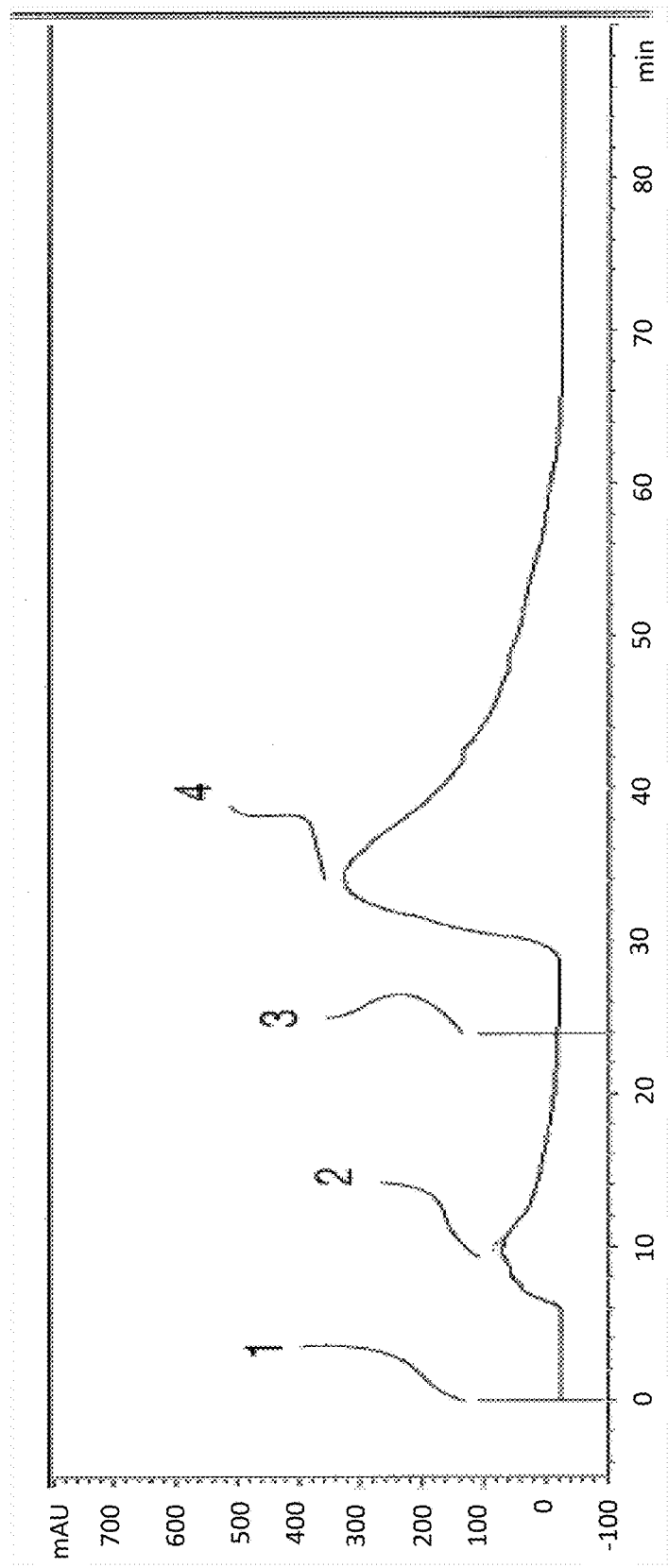
FIG. 15 shows a chromatography profile obtained when carrying out the method for purifying a transgenic human Factor VII, produced with the affinity support in which anti-GLA nucleic aptamers are immobilized. Along the x-axis; the time; along the y-axis: the absorbance value (O.D.) at 254 nanometers. (1): moment of injection; (2): nonretained fraction; (3): moment of injection of the elution buffer; (4): elution fraction.

FIG. 15 shows a chromatography profile for human plasma FVII, with continuous monitoring of the absorbance values (OD) at 254 nanometers.

In FIG. 15, the injection (1) of human plasma FIX concentrate is followed rapidly by the elimination peak (2) of the fraction not retained on the affinity support. The affinity support continues to saturate with the coagulation protein of interest: complexes between (i) the anti-GLA nucleic aptamers of the affinity support and (ii) the human plasma FVII molecules initially contained in the composition to be purified were formed. After running the composition to be purified, a step of washing the column with the previously specified washing buffer is carried out. Then, the elution step is carried out by injecting the elution buffer solution comprising a final concentration of 10 mM of EDTA.

The absorption peak (3) in FIG. 15 shows the release of human plasma FIX from the nucleic aptamer/recombinant FIX complexes, during the elution step.

It should be noted that the human plasma FIX molecules are released rapidly, and thus in a small volume. Consequently, by virtue of the affinity support of the invention, an elution solution is obtained with a high concentration of human plasma FIX protein.

After elution, a step of regenerating the affinity support was carried out, with a 20 mM Tris buffer.

A chromatogram is produced and an SDS-PAGE gel electrophoresis was carried out with Coomassie blue staining. The results are shown in FIG. 16.

Figure 16:
FIG. 16 is the image of an SDS-PAGE electrophoresis gel of proteins contained in a prepurified fraction of human plasma Factor VII, having undergone chromatography on an affinity support on which nucleic aptamers specific for GLA-domain proteins are grafted. The SDS-PAGE gel was treated with Coomassie blue. From left to right: (1): lane 1 ("Start"): starting composition, human plasma Factor VII; (2): lane 2 ("Eluate"): proteins contained in the elution fraction; (3): Des-Gla FVII: poorly glycosylated forms of FVII; (4): other poorly identified forms of FVII.

The analysis of the chromatogram in FIG. 16 shows that the eluate exhibits good chromatographic purity and is characterized by the fact that Factor VII functionality is maintained.

The analysis of the chromatogram in FIG. 16 shows that only the active forms of the starting purified human plasma FVII were retained on the affinity support. The inactive forms present in the starting purified composition, including the poorly glycosylated forms of FVII and the Des-Gla forms of FVII, were not retained on the affinity support.

The results of example 11-A show the ability of the Mapt-2-CS aptamer that was immobilized on the affinity support in the absence of a spacer chain, for example in the absence of a polyethylene glycol spacer chain, to purify human Factor VII from a complex starting medium containing numerous plasma-derived impurities.

B. Use of an Affinity Support Comprising the Immobilized Mapt-2.2-CS Aptamer

An affinity support on which molecules of the biotinylated Mapt-2.2.-CS aptamer comprising a PEG (C18) spacer chain were immobilized, was used.

With this affinity support, human plasma Factor VII was purified to 98% purity (ACSET®).

The affinity support was prepared in accordance with the protocol described in example 7. The affinity support of example 11-B comprises Mapt-2.2.-CS aptamers comprising the nucleic acid having the sequence SEQ ID No. 37 which are immobilized.

The affinity support used to carry out example 11-B has a theoretical ligand density of 0.50 mg/ml. A gel volume of 1 ml was used.

The affinity support is equilibrated with a 0.05M Tris-HCl, 0.05M NaCl, 0.01M $CaCl_2$, 0.004M $MgCl_2$ buffer at pH 7.5.

A human plasma FVII load purified to 98% in a quantity of 115 µg per milliliter of affinity support (gel) is used for the human FVII purification step.

The purified human plasma FVII solution, previously adjusted to 4 mM $MgCl_2$ and 10 mM $CaCl_2$ and pH 7.5, is injected onto the aptamer-agarose gel (affinity support) with a peristaltic pump at a flow rate of 0.05 ml/minute, i.e. a contact time with the affinity support of 20 minutes (I/O).

After injection, the gel is washed in 50 mM Tris+50 mM NaCl+4 mM $MgCl_2$+10 mM $CaCl_2$ buffer at pH 7.5.

A volume of 10 ml of nonadsorbed solution is recovered.

The FVII is eluted with a 50 mM Tris-HCl+10 mM EDTA buffer at pH 7.5. The elution peak is collected according to the OD profile.

In order to regenerate the affinity support, a 1M NaCl, 50% propylene glycol buffer at pH 7.5 is used.

Figure 17:
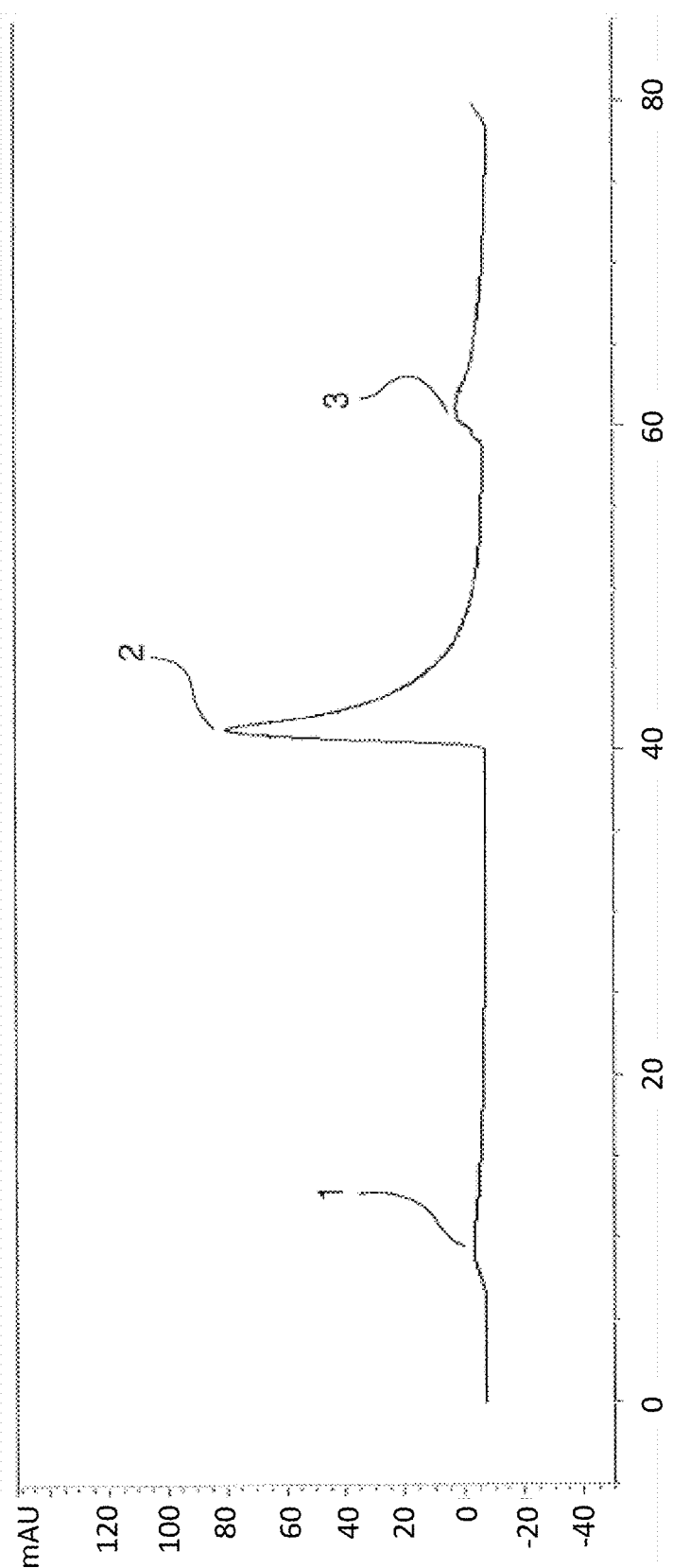
FIG. 17 shows a chromatography profile obtained when carrying out the method for purifying a transgenic human factor VII, produced with the affinity support in which anti-GLA nucleic aptamers are immobilized. Along the x-axis: the time; along the y-axis: the absorbance value (O.D.) at 254 nanometers. (1): nonretained fraction; (2): elution fraction; (3): regeneration fraction.

The chromatography profile is shown in FIG. 17. In FIG. 17, the injection of human plasma FVII concentrate is followed by the elimination peak (1) of the fraction not retained on the affinity support. The affinity support continues to saturate with the coagulation protein of interest: complexes between (i) the anti-GLA nucleic aptamers of the affinity support and (ii) the human plasma FIX molecules initially contained in the composition to be purified were formed. After running the composition to be purified, a step of washing the column with the previously specified washing buffer is carried out. Then, the elution step is carried out by injecting the elution buffer solution comprising a final concentration of 10 mM of EDTA.

The absorption peak (2) in FIG. 17 shows the release of human plasma FVII from the nucleic aptamer/recombinant FVII complexes, during the elution step.

It is specified that the nonretained fraction represents 9% by weight of proteins contained in the starting sample, the elution fraction contains 78% by weight of proteins contained in the starting sample and the regeneration fraction represents 13% by weight of proteins contained in the starting sample.

Figure 18:
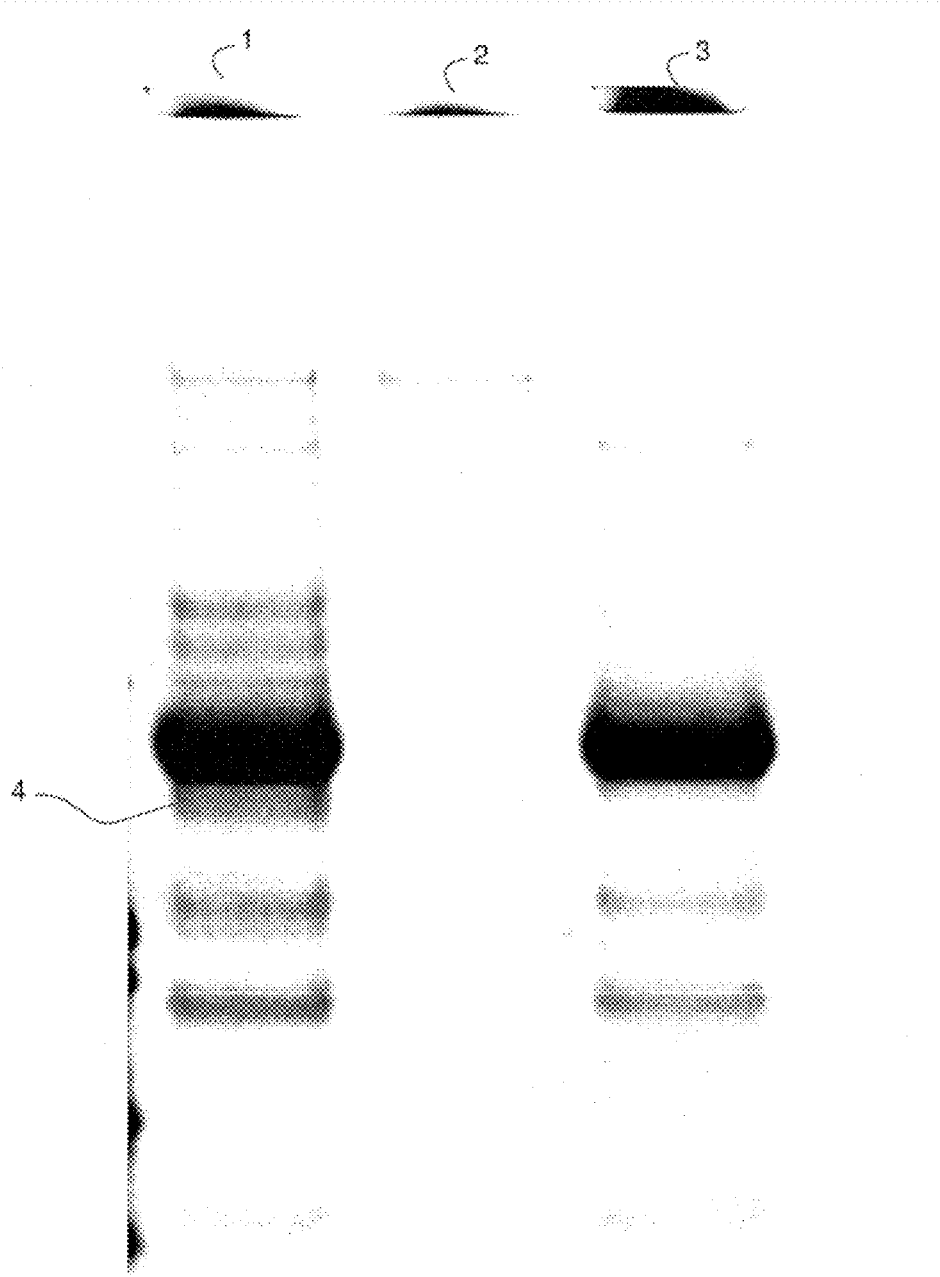
FIG. 18 is the image of an SDS-PAGE electrophoresis gel of proteins contained in a prepurified fraction of human plasma Factor VII, having undergone chromatography on an affinity support on which nucleic aptamers specific for GLA-domain proteins are grafted. The SDS-PAGE gel was treated with Coomassie blue. From left to right: (1): lane 1 ("Start"): starting composition, human plasma Factor VII; (2): lane 2 ("NR"): fraction of nonretained proteins; (3): lane 3: ("Eluate"): proteins contained in the elution fraction; (4): Des-Gla FVII, poorly glycosylated forms of FVII.

Moreover, FIG. 18 shows the excellent ability of the affinity support on which Mapt-2.2.-CS aptamer molecules are immobilized, to purify human Factor VII.

The results of FIG. 18 show that the eluate fraction exhibits good electrophoretic purity.

The analysis of the chromatogram in FIG. 18 shows that only the active forms of the starting purified human plasma FVII were retained on the affinity support. The inactive forms present in the starting purified composition, including the poorly glycosylated forms of FVII and the Des-Gla forms of FVII, were not retained on the affinity support.

The results of example 11-B show the ability of the Mapt-2.2.-CS aptamer that was immobilized on the affinity support to purify human Factor IX from a complex starting medium containing numerous plasma-derived impurities.

Example 12: Optimization of Conditions for Capture of the Aptamers on the Affinity Support A solid support was produced on which molecules of the nucleic aptamer of the invention having the sequence SEQ ID No. 39, of 80 nucleotides, also denoted here as "Mapt2" were immobilized. Before being bound to the solid support, the 5' end of the Mapt2 aptamer was chemically coupled to a spacer chain consisting of 5 molecules of PEG (C18). Then, the free end of the spacer chain, opposite to the end coupled to the aptamer, was coupled to a biotin molecule.

A solid support containing immobilized molecules of streptavidin is available (series S sensor Chip SA, GE).

Then, the above solid support was brought into contact with the above aptamer compounds in order to immobilize the nucleic acids having the sequence SEQ ID No. 39, by noncovalent association between the streptavidin molecules of the support and the biotin molecules of the aptamer compounds.

The Mapt2 aptamer is thus immobilized with an immobilization rate of 4900 RU (1 RU corresponds approximately to 1 pg of product immobilized per $mm^2$).

Human FVII purified from plasma (FVII HP, purity: 99%) was diluted in various run buffers, respectively:
buffer 1: 50 mM Tris, 50 mM NaCl, 10 mM $CaCl_2$, 4 mM $MgCl_2$, pH 7.5;
buffer 2: 50 mM Tris, 50 mM NaCl, 10 mM $CaCl_2$, 10 mM $MgCl_2$, pH 7.5;
buffer 3: 50 mM Tris, 50 mM NaCl, 20 mM $MgCl_2$, pH 7.5;
buffer 4: 50 mM Tris, 10 mM $CaCl_2$, 4 mM $MgCl_2$, pH 7.5; and
buffer 5: 50 mM Tris, 10 mM $CaCl_2$, pH 7.5.

Each sample was injected sequentially onto the same chip (solid support) containing the Mapt2 aptamer immobilized by a biotin-streptavidin interaction. Controls are obtained by injecting blanks containing only run buffer. All the injections were carried out with a flow rate of 30 µl/min for 60 sec; after the injection, run buffer was injected onto the chip at an identical flow rate for 120 sec.

Elution buffer (5 mM EDTA) was then injected for 30 sec with a flow rate of 30 µl/min to uncouple the FVII HP from the aptamer.

The chip makes it possible to study in real time the formation and the disruption of the interactions between the FVII HP and the immobilized aptamer through surface plasmon resonance (SPR). Binding to the immobilized aptamer generates an increase in the signal expressed in resonance units (RU) recorded by the apparatus. These analyses are carried out with the Biacore T100 SPR apparatus (GE). The modeling of the recorded interactions is carried out using the Biaevaluation software (GE).

Figure 19:
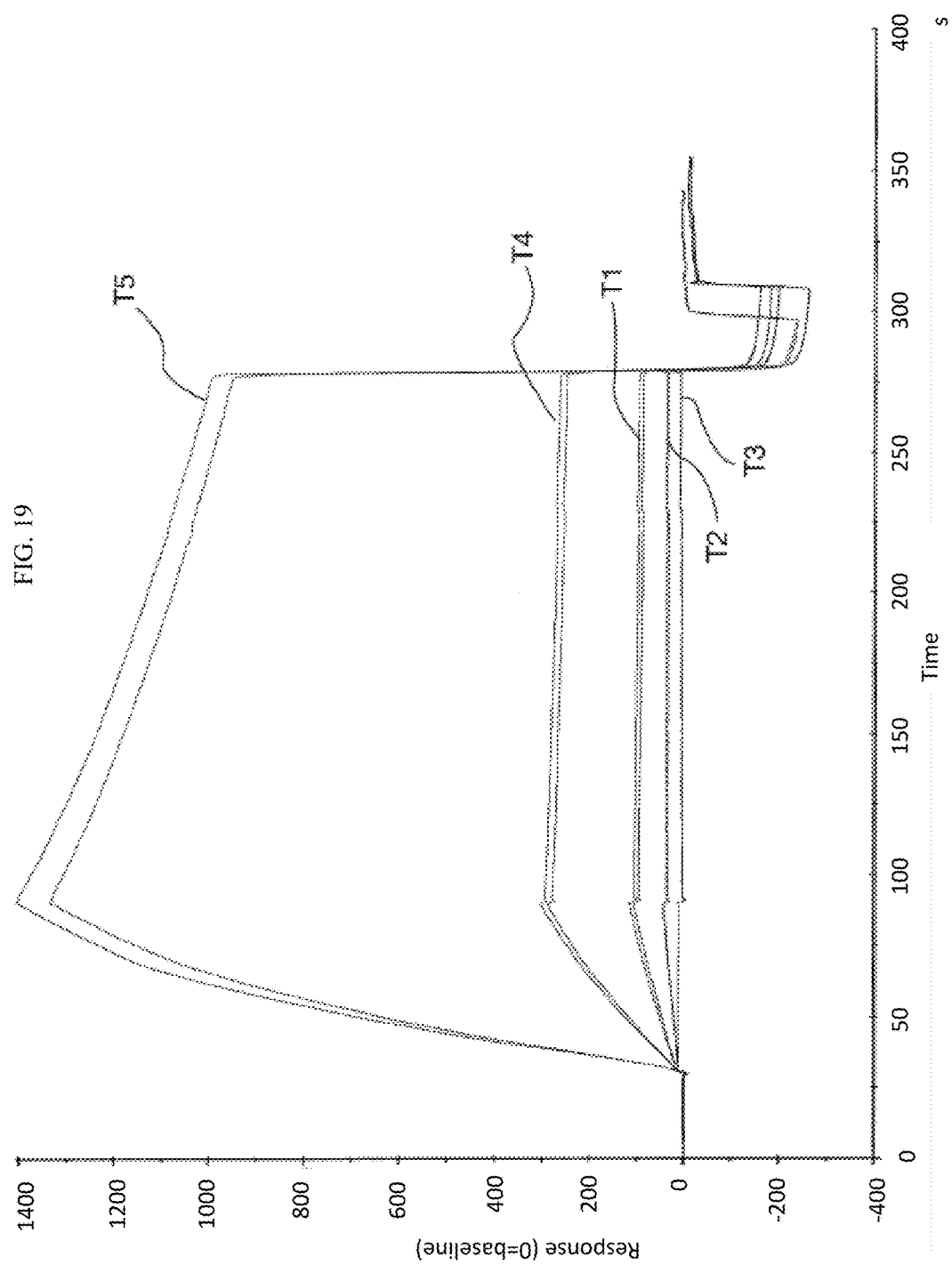
FIG. 19 shows the curves of binding of the Mapt-2 aptamer which is immobilized on a support, to human plasma Factor VII, in an assay according to the surface plasmon resonance technique. The curves correspond to the plasma FVII binding kinetics during the use of various running buffers, respectively, from bottom to top of FIG. 16: T3: buffer 3, T2: buffer 2, T1: buffer 1, T4: buffer 4 and T5: buffer 5. Along the x-axis: the time, expressed in seconds; along the y-axis: resonance signal, expressed in arbitrary resonance units. From bottom to top of the figure: curves illustrating interactions of increasing affinity.

The results are shown in FIG. 19.

The results in FIG. 19 show that the optimum capture conditions are obtained with buffer 5, which comprises neither NaCl nor $MgCl_2$.

The results in FIG. 19 show that the presence of $MgCl_2$ is not necessary for the optimum capture of FVII by the immobilized aptamer molecules. The results show that the presence of $MgCl_2$ is even unfavorable to the optimum binding of FVII.

Moreover, the results in FIG. 19 show that the presence of NaCl in the run buffer is unfavorable to the optimum binding of FVII to the aptamer molecules immobilized on the affinity support.

Figure 20:
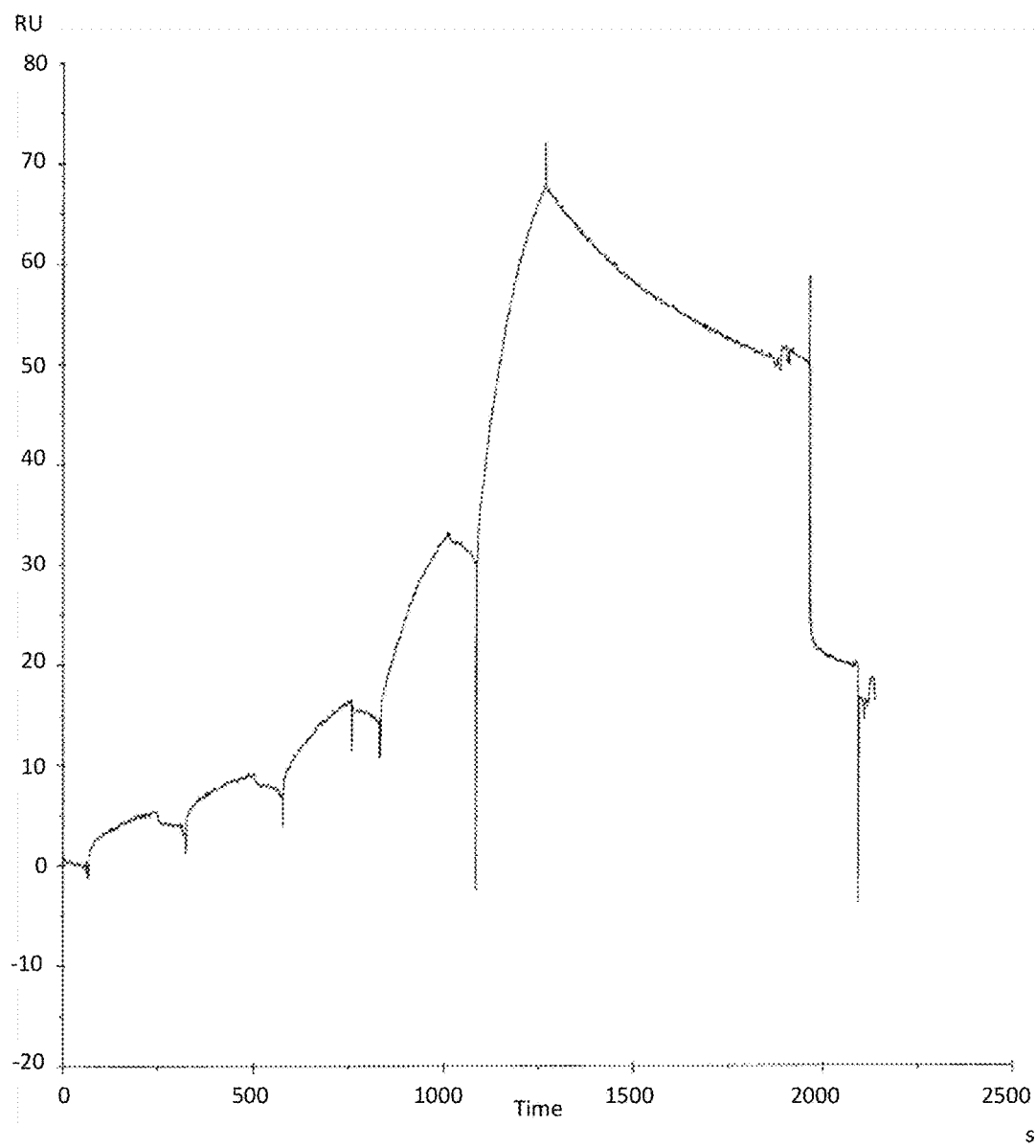
FIG. 20 shows the curves of binding of the Mapt-2 aptamer which is immobilized on a support, to human plasma Factor VII, in an assay according to the surface plasmon resonance technique. The curve makes it possible to determine the parameters of the plasma FVII binding kinetics during the use of buffer 1 (50 mM Tris, 50 mM NaCl, 10 mM $CaCl_2$, 4 mM $MgCl_2$, pH 7.5). Along the x-axis: the time, expressed in seconds; along the y-axis, resonance signal, expressed in arbitrary resonance units.
Figure 21:
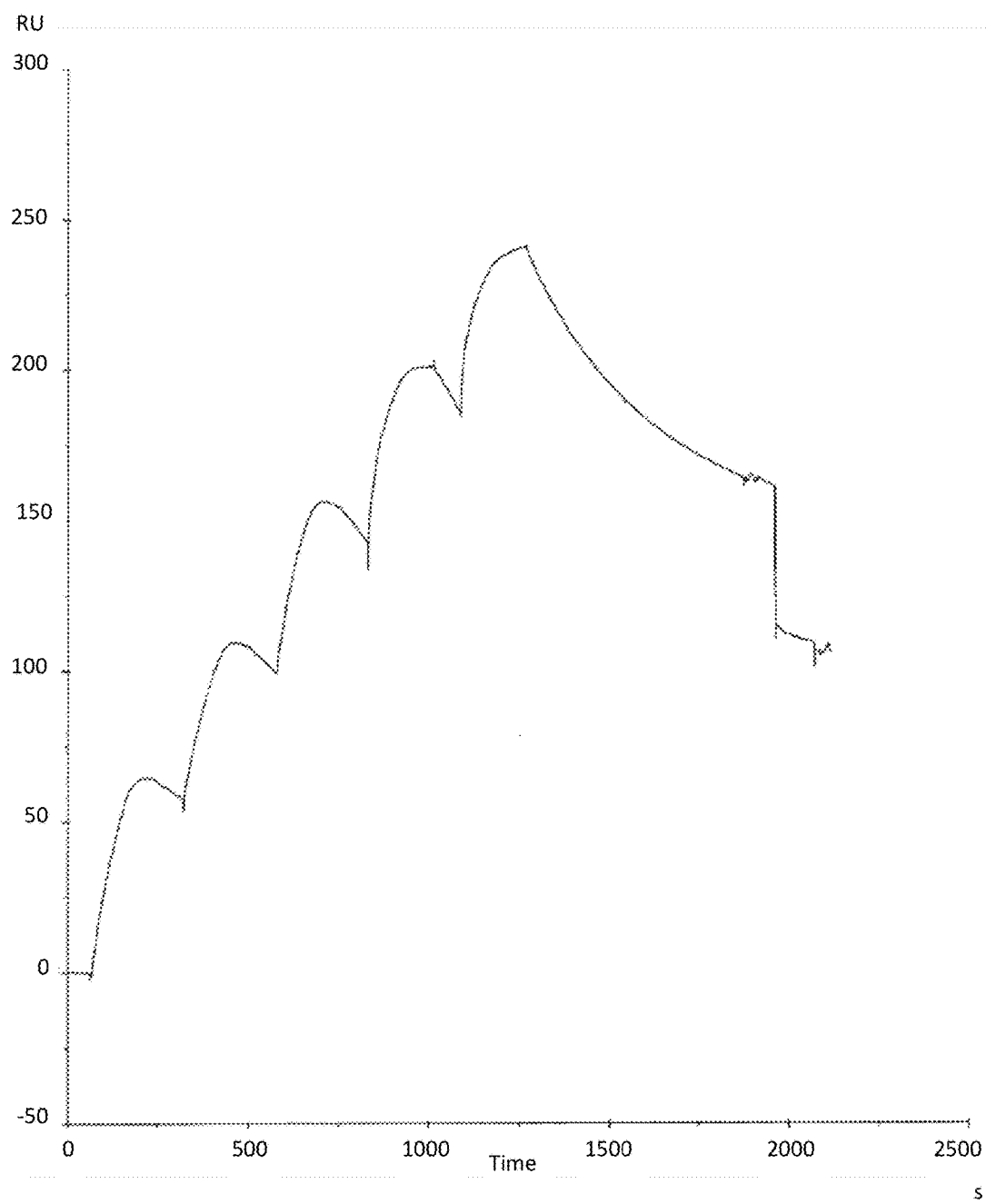
FIG. 21 shows the curves of binding of the Mapt-2 aptamer which is immobilized on a support, to human plasma Factor VII, in an assay according to the surface plasmon resonance technique. The curve corresponds to the plasma FVII binding kinetics during the use of buffer 5 (50 mM Tris, 10 mM $CaCl_2$, pH 7.5). Along the x-axis: the time, expressed in seconds; along the y-axis, resonance signal, expressed in arbitrary resonance units.

FIGS. 20 and 21 show the kinetic analysis of the binding of human plasma FVII to the Mapt-2 aptamers immobilized on the affinity support, respectively with buffer 1 (FIG. 20) and with buffer 5 (FIG. 21).

The results in FIG. 20 show that, with buffer 1, the aptamer exhibits an affinity for human FVII of 148 nM (Kd value), a ka value of $3.3 \times 10^3$ $M^{-1}$ $s^{-1}$, and a kd value of $4.8 \times 10^{-4}$ $s^{-1}$.

The results in FIG. 21 show that, with buffer 5, the aptamer exhibits an affinity for human FVII of 13 nM (Kd value), a ka value of $4.7 \times 10^4$ $M^{-1}$ $s^{-1}$, and a kd value of $6 \times 10^{-4}$ $s^{-1}$.

Example 13: Optimization of the Conditions for Washing the Aptamers on the Affinity Support The affinity support described for example X8 above was used.

Figure 22:
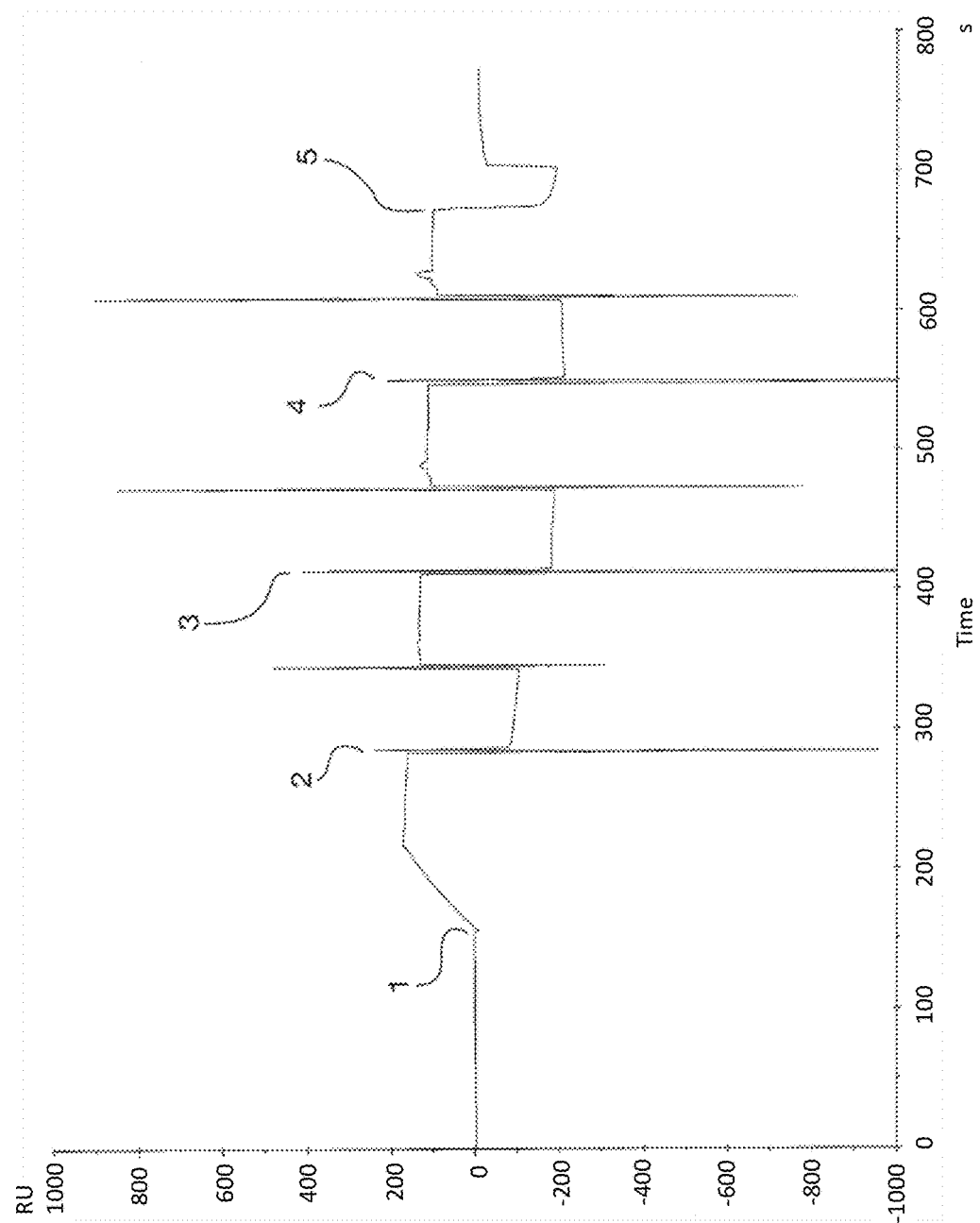
FIG. 22 shows the curves of binding of the Mapt-2 aptamer which is immobilized on a support, to human plasma Factor VII, in an assay according to the surface plasmon resonance technique. The curves correspond to the resistance of the binding of plasma FVII to Mapt-2 during the use of various washing buffers: (1): injection of FVII; (2): 50 mM Tris buffer containing 1M NaCl, 10 mM $CaCl_2$, 4 mM $MgCl_2$, pH 7.5, (3): 50 mM Tris buffer containing 2M NaCl, 10 mM $CaCl_2$, 4 mM $MgCl_2$, pH 7.5, (4): 50 mM Tris buffer containing 3M NaCl, 10 mM $CaCl_2$, 4 mM $MgCl_2$, pH 7.5 and (5): 50 mM Tris buffer containing 10 mM EDTA. Along the x-axis: the time, expressed in seconds; along the y-axis: resonance signal, expressed in arbitrary resonance units.

FIG. 22 shows results relating to the possible effects of various washing conditions on the retention of human FVII on the Mapt-2 aptamers immobilized on the affinity support. The following washing buffers were tested: (1) 50 mM Tris, 1M NaCl, 10 mM $CaCl_2$, 4 mM $MgCl_2$ buffer, pH 7.5, (2) 50 mM Tris, 2M NaCl, 10 mM $CaCl_2$, 4 mM $MgCl_2$ buffer, pH 7.5, (3) 50 mM Tris, 3M NaCl, 10 mM $CaCl_2$, 4 mM $MgCl_2$ buffer, pH 7.5, and (4) 50 mM Tris, 10 mM EDTA buffer.

The results show that the use of increasing concentrations of NaCl does not cause any modification of the binding of human FVII to the Mapt-2 aptamers.

The results in FIG. 22 show that the FVII remains bound to the Mapt-2 aptamer, even when a step of washing the affinity support is carried out with a high ionic strength buffer.

The results in FIG. 22 also show that the FVII is eluted with EDTA.

Figure 23:
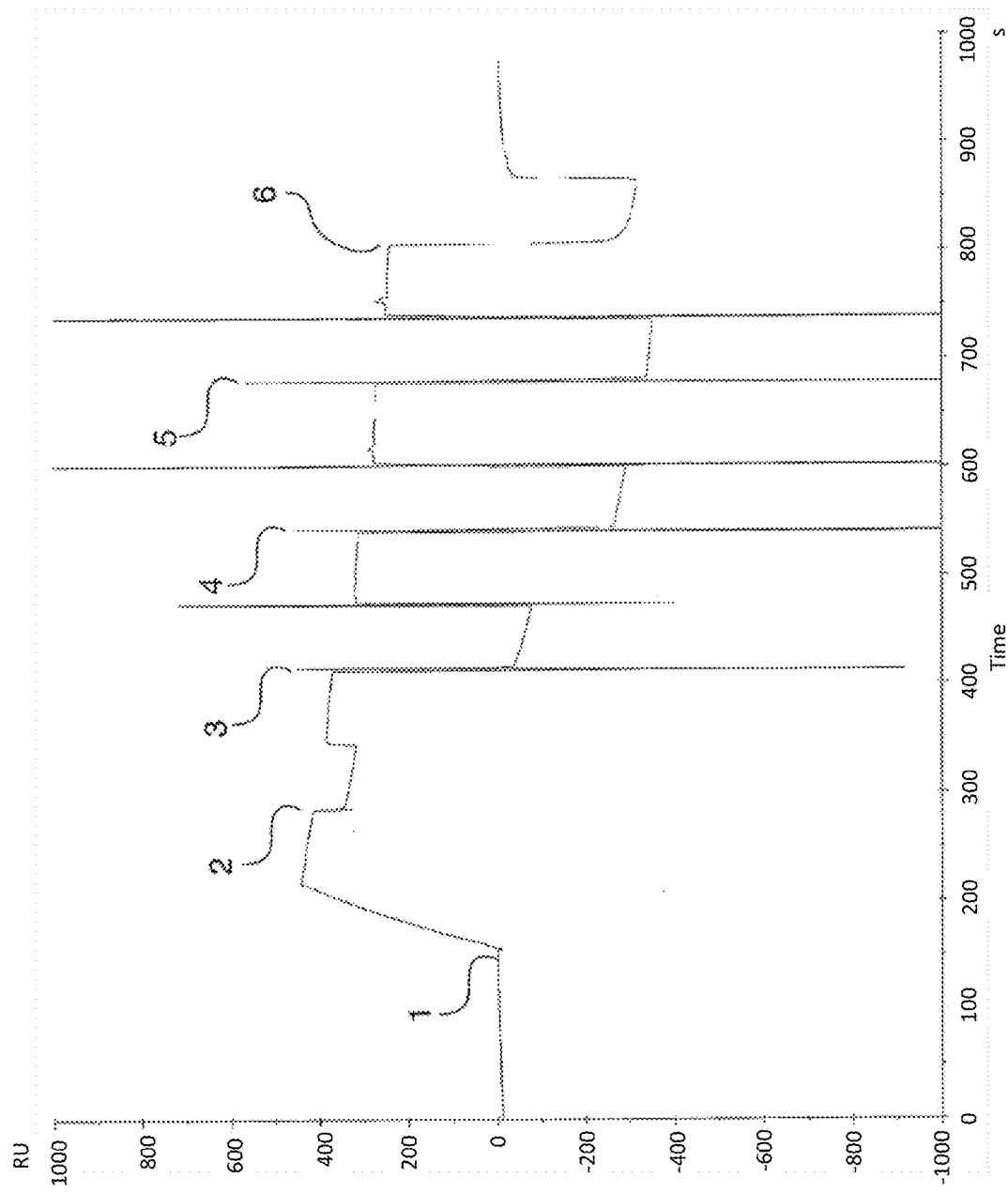
FIG. 23 shows the curves of binding of the Mapt-2 aptamer which is immobilized on a support, to human plasma Factor VII, in an assay according to the surface plasmon resonance technique. The curves correspond to the resistance of the binding of plasma FVII to Mapt-2 when various washing buffers are used: (1): injection of FVII; (2): 50 mM Tris buffer containing 10 mM $CaCl_2$, 4 mM $MgCl_2$, pH 7.5, (3): 50 mM Tris buffer containing 10 mM $CaCl_2$, 4 mM $MgCl_2$, 1M NaCl, pH 7.5, (4): 50 mM Tris buffer containing 10 mM $CaCl_2$, 4 mM $MgCl_2$, 2M NaCl, pH 7.5.

FIG. 23 shows results relating to the possible effects of various washing conditions on the retention of human FVII on the Mapt-2 aptamers immobilized on the affinity support. The following washing buffers were tested: (1) 50 mM Tris, 10 mM $CaCl_2$, 4 mM $MgCl_2$ buffer, pH 7.5, (2) 50 mM Tris, 10 mM $CaCl_2$, 4 mM $MgCl_2$, 1M NaCl buffer, pH 7.5, (3) 50 mM Tris, 10 mM $CaCl_2$, 4 mM $MgCl_2$, 2M NaCl buffer, pH 7.5, (4) 50 mM Tris, 10 mM $CaCl_2$, 4 mM $MgCl_2$, 3M NaCl buffer, pH 7.5, and (5) 50 mM Tris, 10 mM EDTA buffer.

The results show that the use of increasing concentrations of NaCl does not cause any modification of the binding of human FVII to the Mapt-2 aptamers.

The results in FIG. 23 show that the FVII remains bound to the Mapt-2 aptamer, even when a step of washing the affinity support is carried out with a high ionic strength buffer.

The results in FIG. 23 also show that the FVII is eluted with EDTA.

FIG. 24 shows results relating to the possible effects of various washing conditions on the retention of human FVII on the Mapt-2 aptamers immobilized on the affinity support. The following washing buffers were tested: (1) 10% ethanol buffer, (2) 50 mM Tris, 10 mM $CaCl_2$, 4 mM $MgCl_2$, 1M NaCl buffer, pH 7.5, (3) 50 mM Tris, 10 mM $CaCl_2$, 4 mM $MgCl_2$, 2M NaCl buffer, pH 7.5, (4) 50 mM Tris, 10 mM $CaCl_2$, 4 mM $MgCl_2$, 3M NaCl buffer, pH 7.5, and (5) 50 mM Tris, 10 mM EDTA buffer.

The results in FIG. 24 show that the use of ethanol in the washing step does not cause any modification of the binding of human FVII to the Mapt-2 aptamers.

The results show that the use of increasing concentrations of NaCl in the washing step does not cause any modification of the binding of human FVII to the Mapt-2 aptamers.

The results in FIG. 24 show that FVII remains bound to the Mapt-2 aptamer, even when a step of washing the affinity support is carried out with a high ionic strength buffer.

The results in FIG. 24 also show that the FVII is eluted with EDTA.

Example 14: Optimization of the Conditions for Washing the Aptamers on the Affinity Support A solid support was produced on which molecules of the Mapt-1 nucleic aptamer of the invention having the sequence SEQ ID No. 4, also denoted here "Mapt1", were immobilized. Before being bound to the solid support, the 5' end of the Mapt2 aptamer was chemically coupled to a spacer chain consisting of 5 molecules of PEG (C18). Then, the free end of the spacer chain, opposite to the end coupled to the aptamer, was coupled to a biotin molecule.

A solid support containing immobilized streptavidin molecules is available (series S sensor Chip SA, GE).

Then, the above solid support was brought into contact with the above aptamer compounds in order to immobilize the nucleic acids having the sequence SEQ ID No. 4, by noncovalent association between the streptavidin molecules of the support and the biotin molecules of the aptamer compounds.

The Mapt1 aptamer is thus immobilized with an immobilization rate of 4900 RU (1 RU corresponds approximately to 1 pg of product immobilized per $mm^2$).

Each sample was injected sequentially onto the same chip (solid support) containing the Mapt1 aptamer immobilized by biotin-streptavidin interaction. Controls are obtained by injecting blanks containing only run buffer. All the injections were carried out with a flow rate of 30 µl/min for 60 sec; after the injection, run buffer was injected onto the chip at an identical flow rate for 120 sec.

Elution buffer (5 mM EDTA) was then injected for 30 sec with a flow rate of 30 µl/min to uncouple the FVII HP from the aptamer.

The chip makes it possible to study in real time the formation and the disruption of the interactions between FIX and the immobilized aptamer through surface plasmon resonance (SPR). Binding to the immobilized aptamer generates an increase in the signal expressed in resonance units (RU) recorded by the apparatus. These analyses are carried out with the Biacore T100 SPR apparatus (GE). The modeling of the recorded interactions is carried out by means of the Biaevaluation software (GE).

FIG. 25 shows results relating to the possible effects of various washing conditions on the retention of human FIX on the Mapt-1 aptamers immobilized on the affinity support. The following washing buffers were tested: (1) 50 mM Tris, 10 mM $CaCl_2$, 4 mM $MgCl_2$, 1M NaCl buffer, pH 7.5, (2) 50 mM Tris, 10 mM $CaCl_2$, 4 mM $MgCl_2$, 2M NaCl buffer, pH 7.5, (3) 50 mM Tris, 10 mM $CaCl_2$, 4 mM $MgCl_2$, 3M NaCl buffer, pH 7.5, and (5) 50 mM Tris, 10 mM EDTA buffer.

The results show that the use of increasing concentrations of NaCl in the washing step does not cause any modification of the binding of human FIX to the Mapt-1 aptamers.

The results in FIG. 25 show that the FIX remains bound to the Mapt-1 aptamer, even when a step of washing the affinity support is carried out with a high ionic strength buffer.

The results in FIG. 25 also show that the FIX is eluted with EDTA.

FIG. 26 shows results relating to the possible effects of propylene glycol (at 50%) on the retention of human FIX on the Mapt-1 aptamers immobilized on the affinity support. A 50 mM Tris, 10 mM $CaCl_2$, 50% propylene glycol buffer, pH 7.5, was tested.

The results in FIG. 26 show that the use of propylene glycol in the washing step does not cause a modification of the binding of human FIX to the Mapt-1 aptamers.

The invention claimed is:

1. A method for purifying biologically active GLA-domain coagulation proteins, comprising the following steps:
   a) bringing a sample which contains one or more biologically active GLA-domain coagulation proteins, and which contains biologically inactive molecules of one or more GLA-domain protein(s), into contact with an affinity support having thereon immobilized nucleic aptamers which bind specifically to at least one biologically active GLA-domain coagulation protein, but not to biologically inactive molecules of said at least one GLA-domain coagulation protein, in order to form complexes between (i) said nucleic aptamers and (ii) said biologically active GLA-domain coagulation protein(s),
   b) releasing the biologically active GLA-domain coagulation protein(s) from the complexes formed in step a), and
   c) recovering said biologically active GLA-domain coagulation protein(s) in a purified form.

2. The method as claimed in claim 1, wherein said nucleic aptamers consist of deoxyribonucleic aptamers.

3. The method as claimed in claim 2, wherein said nucleic aptamers are included in the structure of a compound of formula (I) below:

[IMM]$_x$-[SPAC]$_y$-[APT]    (I)

wherein:
   [IMM] is a compound for immobilization on a support,
   [SPAC] is a spacer chain,
   [APT] is a nucleic acid which binds specifically to at least one biologically active GLA-domain coagulation protein, but not to biologically inactive molecules of said at least one GLA-domain coagulation protein,
   x is 1, and
   y is 0 or 1.

4. The method as claimed in claim 1, wherein said nucleic aptamers are included in the structure of a compound of formula (I) below:

[IMM]$_x$-[SPAC]$_y$-[APT]    (I)

wherein:
   [IMM] is a compound for immobilization on a support,
   [SPAC] is a spacer chain,
   [APT] is a nucleic acid which binds specifically to at least one biologically active GLA-domain coagulation protein, but not to biologically inactive molecules of said at least one GLA-domain coagulation protein,
   x is 1, and
   y is 0 or 1.

5. The method as claimed in claim 1, wherein said biologically active GLA-domain coagulation protein is a vitamin K-dependent coagulation factor.

6. The method as claimed in claim 1, wherein said biologically active GLA-domain coagulation protein is Factor II, Factor VII, Factor IX, Factor X, protein C, or protein S.

7. The method as claimed in claim 1, for simultaneously purifying at least two biologically active GLA-domain proteins selected from Factor II, Factor VII, Factor IX, Factor X, protein C, and protein S.

8. The method as claimed in claim 1, for simultaneously purifying at least three biologically active GLA-domain proteins selected from Factor II, Factor VII, Factor IX, Factor X, protein C and protein S.

9. The method as claimed in claim 1, for simultaneously purifying biologically active Factor II, Factor VII, Factor IX and Factor X.

10. The method as claimed in claim 1, wherein said nucleic aptamers consist of aptamers having a sequence chosen from the sequences SEQ ID NOs: 3, 4, and 6 to 39.

11. The method of claim 1 wherein the sample is selected from the group consisting of blood, blood derivatives, milk and milk derivatives.

12. The method of claim 11, wherein the sample is a plasma, a plasma cryoprecipitate or a derivative thereof.

13. The method of claim 11 wherein the sample is a milk or a milk derivative obtained from a non-human animal which is transgenic for said biologically active Gla-domain coagulation protein.

* * * * *

UNITED STATES PATENT AND TRADEMARK OFFICE
CERTIFICATE OF CORRECTION

PATENT NO.       : 9,850,477 B2  
APPLICATION NO.  : 14/936896  
DATED            : December 26, 2017  
INVENTOR(S)      : Gerald Perret et al.

Page 1 of 1

It is certified that error appears in the above-identified patent and that said Letters Patent is hereby corrected as shown below:

On the Title Page

Item (72) Inventors: please replace "Gerard Perret, Choisy le Roi (FR)" with -- Gerald Perret, Choisy le Roi (FR) --.

Signed and Sealed this  
Seventeenth Day of April, 2018

Andrei Iancu  
*Director of the United States Patent and Trademark Office*

SEQUENCE LISTING

<160> NUMBER OF SEQ ID NOS: 39

<210> SEQ ID NO 1
<211> LENGTH: 18
<212> TYPE: DNA
<213> ORGANISM: artificial sequence
<220> FEATURE:
<223> OTHER INFORMATION: 5' part of aptamer

<400> SEQUENCE: 1
gggagatagc cacgacct                                                 18

<210> SEQ ID NO 2
<211> LENGTH: 18
<212> TYPE: DNA
<213> ORGANISM: artificial sequence
<220> FEATURE:
<223> OTHER INFORMATION: 3' part of aptamer

<400> SEQUENCE: 2
tccaggctgt gcgaaagc                                                 18

<210> SEQ ID NO 3
<211> LENGTH: 44
<212> TYPE: DNA
<213> ORGANISM: artificial sequence
<220> FEATURE:
<223> OTHER INFORMATION: central part of aptamer

<400> SEQUENCE: 3
cgcacatgac ttgaagttaa acgcgaatta caaacccagc cccc                    44

<210> SEQ ID NO 4
<211> LENGTH: 80
<212> TYPE: DNA
<213> ORGANISM: artificial sequence
<220> FEATURE:
<223> OTHER INFORMATION: aptamer

<400> SEQUENCE: 4
gggagatagc cacgacctcg cacatgactt gaagttaaac gcgaattaca aacccagccc   60
cctccaggct gtgcgaaagc                                               80

<210> SEQ ID NO 5
<211> LENGTH: 79
<212> TYPE: DNA
<213> ORGANISM: artificial sequence
<220> FEATURE:
<223> OTHER INFORMATION: aptamer

<400> SEQUENCE: 5
gctttcgcac agcctggaca cttcccatta ggggcattc agctaaatac gcagcggctt    60
gaggtcgtgg ctatctccc                                                79

<210> SEQ ID NO 6
<211> LENGTH: 43
<212> TYPE: DNA
<213> ORGANISM: artificial sequence
<220> FEATURE:
<223> OTHER INFORMATION: aptamer

<400> SEQUENCE: 6
cgcacacgac ttgaagttaa acgcgaatta cagaccatgc cca                     43

<210> SEQ ID NO 7
<211> LENGTH: 43
<212> TYPE: DNA
<213> ORGANISM: artificial sequence
<220> FEATURE:
<223> OTHER INFORMATION: aptamer

<400> SEQUENCE: 7
cgcacacgac ttgaagttaa acgcgaatta cggaccaatc cca                43

<210> SEQ ID NO 8
<211> LENGTH: 43
<212> TYPE: DNA
<213> ORGANISM: artificial sequence
<220> FEATURE:
<223> OTHER INFORMATION: aptamer

<400> SEQUENCE: 8
cgcacacgac ttgaagttaa acgcgaacta cagaccaagc cca                43

<210> SEQ ID NO 9
<211> LENGTH: 43
<212> TYPE: DNA
<213> ORGANISM: artificial sequence
<220> FEATURE:
<223> OTHER INFORMATION: aptamer

<400> SEQUENCE: 9
cgcacatgac ttgaagttaa acgcgaacta cataccaagc cca                43

<210> SEQ ID NO 10
<211> LENGTH: 44
<212> TYPE: DNA
<213> ORGANISM: artificial sequence
<220> FEATURE:
<223> OTHER INFORMATION: aptamer

<400> SEQUENCE: 10
cgcacatgac ttgaagttaa acgcgaatta caaacccagc cccc               44

<210> SEQ ID NO 11
<211> LENGTH: 44
<212> TYPE: DNA
<213> ORGANISM: artificial sequence
<220> FEATURE:
<223> OTHER INFORMATION: aptamer

<400> SEQUENCE: 11
cgcacaagac ttgaagttaa acgcgaatta caaacccagc cccc               44

<210> SEQ ID NO 12
<211> LENGTH: 45
<212> TYPE: DNA
<213> ORGANISM: artificial sequence
<220> FEATURE:
<223> OTHER INFORMATION: aptamer

<400> SEQUENCE: 12
tcgcacatga catgaagtta aacgcgaatt acaaacccag ccccc              45

<210> SEQ ID NO 13
<211> LENGTH: 43
<212> TYPE: DNA
<213> ORGANISM: artificial sequence
<220> FEATURE:

<223> OTHER INFORMATION: aptamer

<400> SEQUENCE: 13
cgcacatgac tcgaaataaa cgcgaattac aaacccagcc ccc          43

<210> SEQ ID NO 14
<211> LENGTH: 43
<212> TYPE: DNA
<213> ORGANISM: artificial sequence
<220> FEATURE:
<223> OTHER INFORMATION: aptamer

<400> SEQUENCE: 14
cgcacatgac tcgaagttaa acgcgaatta caaaccaagc cca          43

<210> SEQ ID NO 15
<211> LENGTH: 43
<212> TYPE: DNA
<213> ORGANISM: artificial sequence
<220> FEATURE:
<223> OTHER INFORMATION: aptamer

<400> SEQUENCE: 15
cgcacatgac ttgaagttaa acgcgaatta caaacctagc cca          43

<210> SEQ ID NO 16
<211> LENGTH: 42
<212> TYPE: DNA
<213> ORGANISM: artificial sequence
<220> FEATURE:
<223> OTHER INFORMATION: aptamer

<400> SEQUENCE: 16
cgcacacgac ttgaagttaa cgcgaattac atcccagacc cg           42

<210> SEQ ID NO 17
<211> LENGTH: 42
<212> TYPE: DNA
<213> ORGANISM: artificial sequence
<220> FEATURE:
<223> OTHER INFORMATION: aptamer

<400> SEQUENCE: 17
cgcacatgac ttgaagttaa cgcgaattac aacccagacc cg           42

<210> SEQ ID NO 18
<211> LENGTH: 41
<212> TYPE: DNA
<213> ORGANISM: artificial sequence
<220> FEATURE:
<223> OTHER INFORMATION: aptamer

<400> SEQUENCE: 18
cgcacatgac ttgaagttaa cgcgaattac aacccagacc c            41

<210> SEQ ID NO 19
<211> LENGTH: 43
<212> TYPE: DNA
<213> ORGANISM: artificial sequence
<220> FEATURE:
<223> OTHER INFORMATION: aptamer

<400> SEQUENCE: 19
cgcacacgac ttgaagttaa acgcgaatta caaaccagac ccc          43

<210> SEQ ID NO 20
<211> LENGTH: 43
<212> TYPE: DNA
<213> ORGANISM: artificial sequence
<220> FEATURE:
<223> OTHER INFORMATION: aptamer

<400> SEQUENCE: 20
cgcacatgac ttgaagttaa acgcgaatta caaaccagac ccc          43

<210> SEQ ID NO 21
<211> LENGTH: 43
<212> TYPE: DNA
<213> ORGANISM: artificial sequence
<220> FEATURE:
<223> OTHER INFORMATION: aptamer

<400> SEQUENCE: 21
cgcacatgac ttgaagttaa acgcgaatta cgaaccagac ccc          43

<210> SEQ ID NO 22
<211> LENGTH: 42
<212> TYPE: DNA
<213> ORGANISM: artificial sequence
<220> FEATURE:
<223> OTHER INFORMATION: aptamer

<400> SEQUENCE: 22
cgcacatgac ttgaagttaa cgcgaattac gaaccagacc ca           42

<210> SEQ ID NO 23
<211> LENGTH: 43
<212> TYPE: DNA
<213> ORGANISM: artificial sequence
<220> FEATURE:
<223> OTHER INFORMATION: aptamer

<400> SEQUENCE: 23
cgcacatgac ttgaagttaa acgcgaatta caaaccagac cca          43

<210> SEQ ID NO 24
<211> LENGTH: 43
<212> TYPE: DNA
<213> ORGANISM: artificial sequence
<220> FEATURE:
<223> OTHER INFORMATION: aptamer

<400> SEQUENCE: 24
cgcacatgac ttgaagttaa acgcgaatta caaaccaaac cca          43

<210> SEQ ID NO 25
<211> LENGTH: 43
<212> TYPE: DNA
<213> ORGANISM: artificial sequence
<220> FEATURE:
<223> OTHER INFORMATION: aptamer

<400> SEQUENCE: 25
cgcacatgac ttgaagttaa acgcgaatta caaaccaaac ccg          43

<210> SEQ ID NO 26
<211> LENGTH: 42
<212> TYPE: DNA
<213> ORGANISM: artificial sequence
<220> FEATURE:

<223> OTHER INFORMATION: aptamer

<400> SEQUENCE: 26
cgcacatgac ttgaagttaa cgcgaattac aaaccaaccc cc    42

<210> SEQ ID NO 27
<211> LENGTH: 43
<212> TYPE: DNA
<213> ORGANISM: artificial sequence
<220> FEATURE:
<223> OTHER INFORMATION: aptamer

<400> SEQUENCE: 27
cgcacatgac ttgaagttaa cgcgaataac aacccatccc ccc    43

<210> SEQ ID NO 28
<211> LENGTH: 44
<212> TYPE: DNA
<213> ORGANISM: artificial sequence
<220> FEATURE:
<223> OTHER INFORMATION: aptamer

<400> SEQUENCE: 28
cgcacaatga cttgaagtga aacgcgaata acaaaccagg cccc    44

<210> SEQ ID NO 29
<211> LENGTH: 43
<212> TYPE: DNA
<213> ORGANISM: artificial sequence
<220> FEATURE:
<223> OTHER INFORMATION: aptamer

<400> SEQUENCE: 29
cgcacatgac ttgaagttaa acgcgaatta cagaccaaac cca    43

<210> SEQ ID NO 30
<211> LENGTH: 43
<212> TYPE: DNA
<213> ORGANISM: artificial sequence
<220> FEATURE:
<223> OTHER INFORMATION: aptamer

<400> SEQUENCE: 30
cgcacatgac ttgaagttaa acgcgaatta cagaccaaac ccc    43

<210> SEQ ID NO 31
<211> LENGTH: 43
<212> TYPE: DNA
<213> ORGANISM: artificial sequence
<220> FEATURE:
<223> OTHER INFORMATION: aptamer

<400> SEQUENCE: 31
cgcacatgac ttgaagtaaa acgcgaatta cagaccaaac ccg    43

<210> SEQ ID NO 32
<211> LENGTH: 43
<212> TYPE: DNA
<213> ORGANISM: artificial sequence
<220> FEATURE:
<223> OTHER INFORMATION: aptamer

<400> SEQUENCE: 32
cgcacacgac ttgaagttaa ccgcgaatta caaaccaaac cca    43

<210> SEQ ID NO 33
<211> LENGTH: 42
<212> TYPE: DNA
<213> ORGANISM: artificial sequence
<220> FEATURE:
<223> OTHER INFORMATION: aptamer

<400> SEQUENCE: 33
cgcacacgac gtgaagttaa cgcgaatcac aaaccaaacc cg        42

<210> SEQ ID NO 34
<211> LENGTH: 43
<212> TYPE: DNA
<213> ORGANISM: artificial sequence
<220> FEATURE:
<223> OTHER INFORMATION: aptamer

<400> SEQUENCE: 34
cgcacacagc tcgaagttaa acgcgaatta caaaccaggc ccc        43

<210> SEQ ID NO 35
<211> LENGTH: 43
<212> TYPE: DNA
<213> ORGANISM: artificial sequence
<220> FEATURE:
<223> OTHER INFORMATION: aptamer

<400> SEQUENCE: 35
cgcacatgac ttgaagtaaa acgcgaatta cagaccaaac ccg        43

<210> SEQ ID NO 36
<211> LENGTH: 40
<212> TYPE: DNA
<213> ORGANISM: artificial sequence
<220> FEATURE:
<223> OTHER INFORMATION: aptamer

<400> SEQUENCE: 36
ccacgacctc gcacatgact tgaagtaaaa cgcgaattac        40

<210> SEQ ID NO 37
<211> LENGTH: 44
<212> TYPE: DNA
<213> ORGANISM: artificial sequence
<220> FEATURE:
<223> OTHER INFORMATION: aptamer

<400> SEQUENCE: 37
ccgcacacca cgcgcatgac cccgcgcaca cgacttgaag tagc        44

<210> SEQ ID NO 38
<211> LENGTH: 44
<212> TYPE: DNA
<213> ORGANISM: artificial sequence
<220> FEATURE:
<223> OTHER INFORMATION: aptamer

<400> SEQUENCE: 38
ccgcacgcta cgcgcatgaa cccgcgcaca cgacttgaag tagc        44

<210> SEQ ID NO 39
<211> LENGTH: 80
<212> TYPE: DNA
<213> ORGANISM: artificial sequence
<220> FEATURE:

```
<223> OTHER INFORMATION: aptamer

<400> SEQUENCE: 39
gggagatagc cacgacctcc gcacaccacg cgcatgaccc cgcgcacacg acttgaagta    60
gctccaggct gtgcgaaagc                                                80
```